(12) United States Patent
Matsumoto et al.

(10) Patent No.: US 8,167,794 B2
(45) Date of Patent: May 1, 2012

(54) ENDOSCOPE SYSTEM FOR FLUORESCENT OBSERVATION

(75) Inventors: Shinya Matsumoto, Machida (JP); Akira Hasegawa, Musashino (JP)

(73) Assignee: Olympus Corporation, Tokyo (JP)

( * ) Notice: Subject to any disclaimer, the term of this patent is extended or adjusted under 35 U.S.C. 154(b) by 3 days.

(21) Appl. No.: 12/721,604

(22) Filed: Mar. 11, 2010

(65) Prior Publication Data

US 2010/0168588 A1    Jul. 1, 2010

Related U.S. Application Data

(62) Division of application No. 10/867,739, filed on Jun. 16, 2004, now abandoned.

(30) Foreign Application Priority Data

Jun. 17, 2003 (JP) ................................. 2003-172361
Jun. 14, 2004 (JP) ................................. 2004-176198

(51) Int. Cl.
  *A61B 1/06* (2006.01)
  *A61B 6/00* (2006.01)
(52) U.S. Cl. ....................................... 600/160; 600/476
(58) Field of Classification Search .................. 362/574; 600/160, 178, 181; 359/260
See application file for complete search history.

(56) References Cited

U.S. PATENT DOCUMENTS

| 4,821,117 | A * | 4/1989 | Sekiguchi | 348/68 |
| 5,749,830 | A * | 5/1998 | Kaneko et al. | 600/160 |
| 5,982,488 | A * | 11/1999 | Shirasaki | 356/519 |
| 6,293,911 | B1 * | 9/2001 | Imaizumi et al. | 600/160 |
| 6,829,053 | B1 * | 12/2004 | Mitamura et al. | 356/519 |
| 2002/0013512 | A1 * | 1/2002 | Sendai et al. | 600/160 |
| 2002/0038074 | A1 * | 3/2002 | Hakamata | 600/178 |
| 2003/0229270 | A1 * | 12/2003 | Suzuki et al. | 600/178 |
| 2003/0231690 | A1 * | 12/2003 | McDonald | 372/97 |

FOREIGN PATENT DOCUMENTS

| JP | 63-271308 | 11/1988 |
| JP | 10-201707 | 8/1998 |

* cited by examiner

*Primary Examiner* — Philip R Smith
(74) *Attorney, Agent, or Firm* — Arnold International; Bruce Y. Arnold

(57) ABSTRACT

An endoscope system is disclosed for detecting fluorescent light emitted in the near-infrared region by a plurality of fluorescent labeling materials introduced into a living tissue. An illumination system generates illumination light in the wavelength range 600 nm-2000 nm which serves as excitation light for the plurality of fluorescent labeling materials, and a detection system that can separately detect different ones of the plurality of fluorescent light emissions that are emitted at different wavelengths from among the plurality of fluorescent labeling materials is provided. The endoscope system may include a conventional-type endoscope having an insertion section, or a capsule endoscope that wirelessly transmits image data. By superimposing the image data obtained using reflected light in the visible region and fluorescent light emitted by the fluorescent labeling materials, improved diagnostic capabilities are provided.

2 Claims, 57 Drawing Sheets

| Turret Trans. Range | Visible (27a) | | | Infrared (27b) | | | Infrared (27b) | | |
|---|---|---|---|---|---|---|---|---|---|
| Rot. Disk Trans. Range | B (29a) | G (29b) | R (29c) | Open (28a) | Open (28b) | Open (28c) | Open (28a) | Open (28b) | Open (28c) |
| Tunable Filter — Driving Voltage | $V_0$ (=Const) | | | $V_1$ | $V_2$ | $V_3$ | $V_4$ | $V_5$ | $V_6$ |
| Tunable Filter — Air Gap | $d=d(V_0)$ | | | $d=d(V_1)$ | $d=d(V_2)$ | $d=d(V_3)$ | $d=d(V_4)$ | $d=d(V_5)$ | $d=d(V_6)$ |
| Tunable Filter — Trans. Range (950-1050nm) | $IR_{(V_0)}$ | | | $IR_{(V_1)}$ | $IR_{(V_2)}$ | $IR_{(V_3)}$ | $IR_{(V_4)}$ | $IR_{(V_5)}$ | $IR_{(V_6)}$ |
| CCD Light Rec. Part | $RF_B + F_{IR(V_0)}$ | $RF_G + F_{IR(V_0)}$ | $RF_R + F_{IR(V_0)}$ | $F_{IR(V_1)}$ | $F_{IR(V_2)}$ | $F_{IR(V_3)}$ | $F_{IR(V_4)}$ | $F_{IR(V_5)}$ | $F_{IR(V_6)}$ |

Where:
$$V_0 \neq V_1 \neq V_2 \neq V_3 \neq V_4 \neq V_5 \neq V_6 \text{ and}$$
$$F_{IR(V0)} \neq F_{IR(V1)} \neq F_{IR(V2)} \neq F_{IR(V3)} \neq F_{IR(V4)} \neq F_{IR(V5)} \neq F_{IR(V6)}$$

Fig. 24

| Turret Transmission Range | Visible (27a) | | | Infrared (27b) | | |
|---|---|---|---|---|---|---|
| Rot. Disk Transmission Range | B (29a) | G (29b) | R (29c) | Open (28a) | Open (28b) | Open (28c) |
| Tunable Filter — Driving Voltage | | $V_0$ (=Const) | | $V_1$ | $V_2$ | $V_3$ |
| Tunable Filter — Air Gap | | $d_1 = d_1(V_0)$ $d_2 = d_2(V_0)$ where $d_1 \neq d_2$ | | $d_1 = d_1(V_1)$ $d_2 = d_2(V_1)$ where $d_1 = d_2$ | $d_1 = d_1(V_2)$ $d_2 = d_2(V_2)$ where $d_1 = d_2$ | $d_1 = d_1(V_3)$ $d_2 = d_2(V_3)$ where $d_1 = d_2$ |
| Tunable Filter — Trans. Range (950-1050nm) | | | | $IR_{(V1)}$ | $IR_{(V2)}$ | $IR_{(V3)}$ |
| CCD Light Receiving Part | $RF_B$ | $RF_G$ | $RF_R$ | $F_{IR(V1)}$ | $F_{IR(V2)}$ | $F_{IR(V3)}$ |

Fig. 25

ENDOSCOPE SYSTEM FOR FLUORESCENT OBSERVATION

This application is a divisional application of U.S. Application Ser. No. 10/867,739 that was filed on Jun. 16, 2004 (now abandoned) as well as under 35 U.S.C. 119 of JP 2003-172361, filed in Japan on Jun. 17, 2003, and of JP 2004-176198, filed in Japan on Jun. 14, 2004, the subject matters of which are hereby incorporated by reference.

BACKGROUND OF THE INVENTION

Prior art endoscopes have conventionally been used in diagnosis and treatment where a fluorescent substance having an affinity to a lesion, such as cancer, has been previously administered into a subject's body and excitation light that excites the fluorescent substance is then irradiated onto tissue of the subject so that fluorescent emissions from the fluorescent substance that deposits at the lesion can be detected.

For example, Japanese Laid-Open Patent Application H10-201707 describes a prior art endoscope wherein indocyanine green derivative labeled antibodies have been previously introduced into the living tissue. The lesions then emit fluorescent light when excited by infrared light, with the infrared light being readily transmitted by living tissue without damaging the living tissue. This enables the lesions to be observed by detecting the fluorescent light emissions while the light caused by self-fluorescence (autofluorescence) of the living tissues is blocked in order to aid in preventing lesions that are deep inside the living tissue from being overlooked.

Indocyanine green derivative labeled antibodies attach to human IgG as a fluorescent agent and are excited by excitation light having a peak wavelength of approximately 770 nm. Such labeled antibodies produce fluorescence having a peak wavelength of approximately 810 nm. Japanese Laid-Open Patent Application H10-201707 illuminates living tissue of interest that has previously been administered such a fluorescent agent with light from a light source having wavelengths in the range of approximately 770-780 nm, and then detects light wavelengths that are emitted from the living tissue in the wavelength range of approximately 810-820 nm so as to determine the presence of a lesion.

It is a well known fact that the earlier cancer is detected in a patient the less invasive the treatment; moreover, the treatment is generally more effective so as to provide improved survivability. Early detection of cancer in patients is a goal embraced by workers in the life science/medical field as well as by the population as a whole. However, cancer cells in the earliest stage show only meager morphologic changes from normal cells, and thus, conventional techniques that focus primary on morphologic changes in cells for determining the presence of cancer are not applicable for detecting cancer in the earliest stage.

Furthermore, cancer in the earliest stage typically develops several millimeters deep within the surface of living tissue. In addition, living tissue scatters light in a sufficiently intense manner that the living tissue layer above the cancerous region blocks observation of the cancer. This becomes a remarkably adverse factor in solving the problem of detecting cancer in the earliest stage. Of course, the fact that the tissues to be observed are within a living body is also an adverse factor.

Attempts have been made to develop a technique that combines using infrared light, which can reach deep inside living tissue with the infrared light being minimally scattered or absorbed, with a technology that introduces a plurality of different fluorescent labels into a plurality of different specific proteins. The proteins appear as cancer develops within living cells, and such a technique would enable the detection of cancer in its earliest stage and should enable a diagnosis to be made of whether the cancer has become malignant. In addition to endoscopes, diagnosis systems for cancer include CT, MRI, and PET scanning devices. Each of these devices uses a sensor that is externally provided in order to depict in three dimensions the interior regions of a human body and each is a non-invasive organ examination tool. Such devices can detect cancer once the cancerous region has grown to a size of approximately 1 cm or larger. However, the resolution of these devices is not yet sufficient to enable cancer to be detected in its earliest stage or to enable a diagnosis to be made of whether the cancer has become malignant.

Research in life science such as genomics and proteomics has determined that cancer develops as a pre-cancerous lesion and the lesion gradually grows and transforms into metastatic, infiltrative cancer cells. Cancer is a genetic disease, and it is believed that a succession of genetic mutations causes the cells to become malignant. Gene defects are triggered by the expression (i.e., the presence) of specific proteins in the cell. A diagnosis of malignancy concerning a tumor or cancer can be made only when specific proteins for plural types of cancers are present, or when genes that cause defects are detected.

According to recent reports, tumors can be diagnosed as being either benign or malignant when several types of proteins that are specifically expressed in cancer cells are detected. The diagnosis of the malignancy of a tumor is assured with improved accuracy if various additional types of proteins are detected. Theoretically, plural cancer-specific proteins in a living body can be labeled with different fluorescent light producing substances. Then, the different fluorescent light producing substances can be detected so as to determine the presence of cancer-specific proteins in order to verify a malignancy.

Living tissue scatters light in a sufficiently intense manner that illuminated living tissue is difficult to see through. However, living tissue rarely scatters or absorbs significant amounts of light in the near-infrared to infrared range. For this reason, near-infrared and infrared wavelengths of light are often used in lesion diagnosis techniques. Light of this wavelength range is used as the excitation light for the fluorescent labels so that fluorescent labels that are distributed deep inside a living tissue will emit fluorescence, thereby aiding in the detection of cancer at an early stage.

In the present invention, plural cancer-specific proteins are labeled with different fluorescent light producing substances that fluoresce in the near-infrared to infrared range, and these wavelengths are then detected using an endoscope so as to reveal the presence of cancer-specific proteins in cells that may be several millimeters deep within a living body. It is desirable that the respective fluorescent labels have narrow fluorescent wavelength emissions so that plural fluorescent labels can be introduced and detected, thus increasing the number of types of cancer-specific proteins that can be detected and thereby improving the accuracy of such an endoscopic diagnosis.

Fluorescent labels that bind to cancer-specific proteins are introduced into living tissues, and plural fluorescent wavelengths are detected so that cancer-specific proteins that correspond to the fluorescent wavelengths can be detected. Thus, plural fluorescent labels can be used for fluorescence detection so that cancer in a patient can be diagnosed as being either benign or malignant at an earlier stage.

In prior art endoscopes, the wavelength used can be varied only by varying the wavelength of the light source, and thus a technique for separating plural wavelengths in the near-infrared range is not available in the detection component. Therefore, in prior art endoscopes, plural fluorescent wavelengths that emit fluorescence in the near-infrared range when excited by illumination cannot be detected even when such labels have been previously introduced into living tissue that is to be observed.

BRIEF SUMMARY OF THE INVENTION

The present invention relates to an endoscope system for endoscopic diagnosis of a subject who has been administered, for example, multiple fluorescent labels that emit fluorescence of the near-infrared wavelength range. More specifically, the present invention provides an endoscope system wherein plural fluorescent labels that have been previously introduced into living tissue can be separately detected using wavelengths in the near-infrared range.

BRIEF DESCRIPTION OF THE DRAWINGS

The present invention will become more fully understood from the detailed description given below and the accompanying drawings, which are given by way of illustration only and thus are not limitative of the present invention, wherein:

FIG. 24 shows a timing chart wherein more than three different fluorescent light emitting substances are to be separately detected;

FIG. 25 is a timing chart for use in explaining the operation of the endoscope of the present invention for fluorescence detection and color image observation based on another operation principle;

DETAILED DESCRIPTION

The endoscope system according to the present invention may be used for endoscopic diagnosis of a subject who has been administered plural known fluorescent labels that produce fluorescent light in the near-infrared range, and is characterized by having: an illumination system that includes multiple wavelengths λ in the wavelength range 600 nm≦λ≦2000 nm so as to excite different fluorescent labels; a detection system that includes a wavelength separation element for separating fluorescent wavelengths produced by the fluorescent labels; and a controller that controls the wavelength separation element so as to scan for peak wavelengths of the fluorescence produced by the fluorescent labels.

Figure 1:
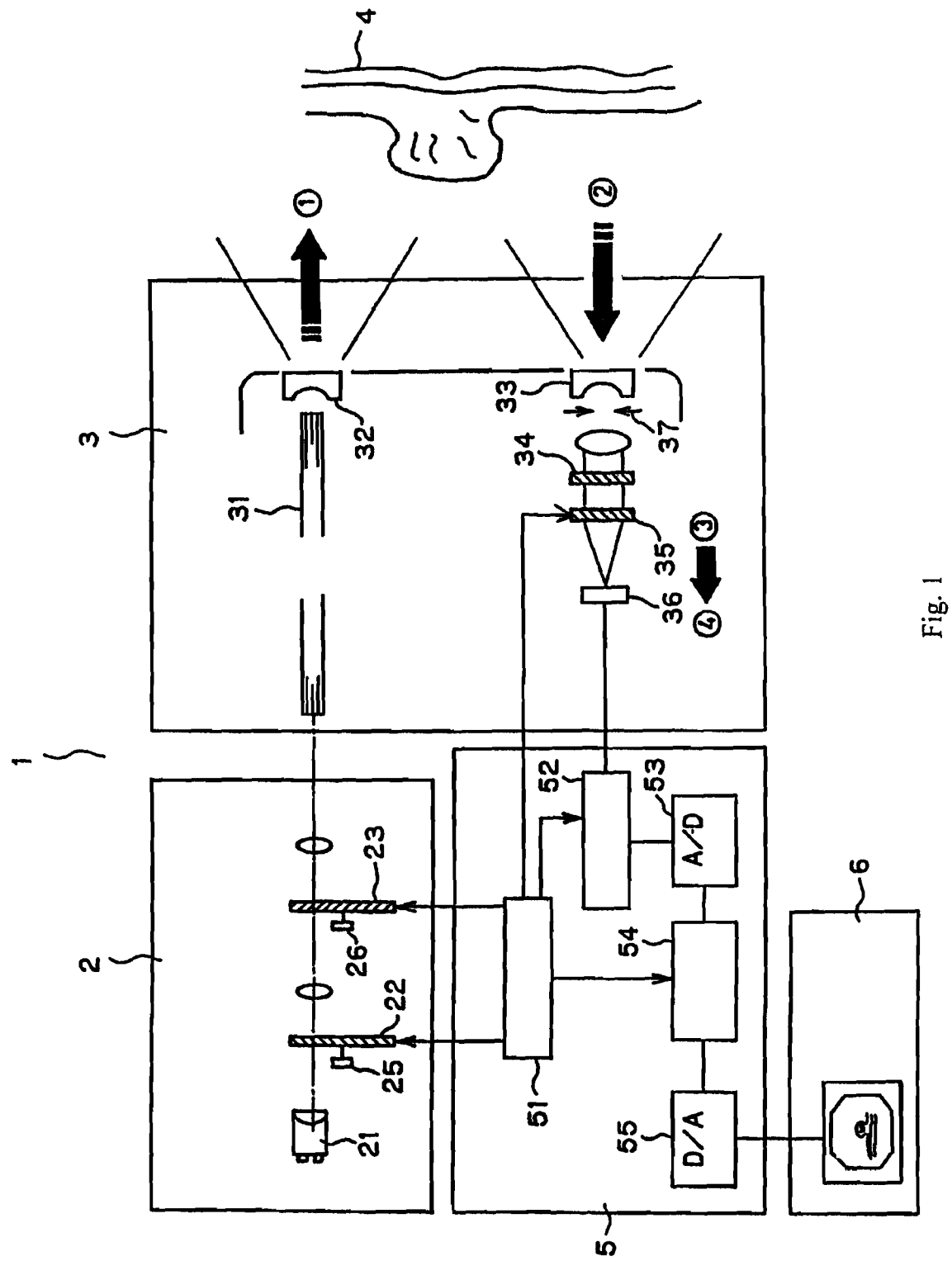
FIG. 1 shows the overall structure of an embodiment of an endoscope system according to the present invention, characterized by having the components that separate and detect plural fluorescent wavelengths positioned within the endoscope tip section of an endoscope that uses an image pickup device (such a combination is sometimes termed an 'electronic endoscope' or a 'video endoscope')
Figure 2:
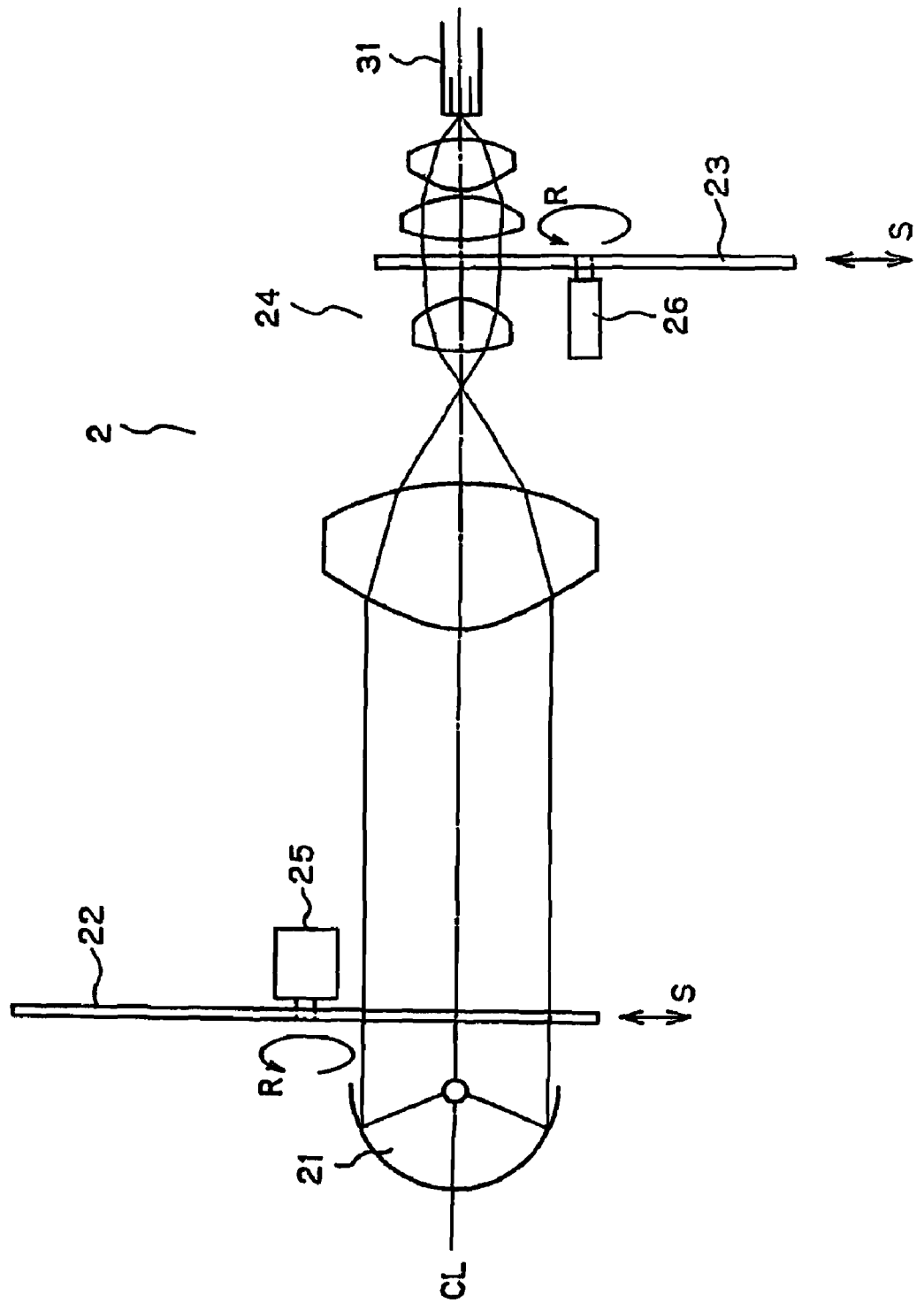
FIG. 2 shows in greater detail the structure of the light source optical system 2 shown in FIG. 1.

The endoscope system shown in FIG. 1 is characterized in that it provides components within the endoscope tip for separating and transmitting plural fluorescent wavelengths so as to enable observations and diagnoses of lesions, such as cancers, using light in the near-infrared range. The wavelength range used is approximately 600-2000 nm, as these wavelengths are not significantly scattered or absorbed when living tissue is illuminated with such wavelengths, and thus these wavelengths reach deep into living tissue and enable a more effective diagnosis of cancer within a living body. A wavelength separation element is controlled so as to scan for the fluorescent emission peaks produced by the fluorescent labels. Such a technique enables high speed separation of fluorescent peak emission wavelengths in the near-infrared range. FIG. 2 shows in greater detail the structure of the light source optical system 2 shown in FIG. 1.

According to a second type of the endoscope system of the present invention, an endoscope system is provided for endoscopic diagnosis of a subject who has previously been administered plural, known fluorescent light emitting labels that produce different fluorescent light emissions in the near-infrared range. The endoscope includes an illumination system for illuminating the subject with wavelengths that include wavelengths in the range 600-2000 nm so as to provide excitation light for the fluorescent labels, a detection system that includes a wavelength separation element for separating the fluorescent light emissions by the different fluorescent substances that comprise the labels, and a controller that controls the wavelength separation element so as to scan for the peak wavelengths of the fluorescent emissions produced by the fluorescent labels, with the detection system and controller being provided in an ocular portion (i.e., the eyepiece portion) of the endoscope.

In the first and second types of the endoscope system of the present invention discussed above, the illumination system includes a light source that is detachably provided with plural wavelength selective filters that are switched into and out of the light path in order to select at least the following two illumination modes:

illumination mode 1—wherein light is emitted only in the visible wavelength range, and illumination mode 2—wherein light is emitted having a wavelength component λ in the range 600≦λ≦2000 nm.

It is desirable that the voltage for driving the wavelength separation element is changed only during the illumination mode 2.

In the first and second types of the endoscope system of the present invention as discussed above, it is desirable that a voltage for driving the wavelength separation element is changed n times for n different fluorescent labels. In this way, at least two fluorescent wavelengths can be separated for observation.

The third type of the endoscope system of the present invention is an endoscope system for endoscopic diagnosis of a subject who has been administered plural known fluorescent labels that, when excited, produce fluorescence in the near-infrared range, characterized by the following: an illumination system for illuminating the subject with at least part of the wavelength range 600-2000 nm including at least part of the excitation wavelengths of the fluorescent labels, a detection system including a wavelength separation element for separating fluorescent wavelengths produced by the plural fluorescent labels, and plural detection elements for detecting individual fluorescent wavelengths separated by the wavelength separation element, wherein the detection system and the plural detection elements are provided at the tip of the endoscope.

The third type of the endoscope system of the present invention separates fluorescent wavelengths without any control of the wavelength separation element, which simplifies the structure of the endoscope system.

The fourth type of the endoscope system of the present invention is for endoscopic diagnosis of a subject administered plural known fluorescent labels producing fluorescence in the near-infrared range, characterized by the following: an illumination system for illuminating the subject with at least part of the wavelength range 600-2000 nm including at least part of the excitation light wavelengths of the fluorescent labels, a detection system and including a wavelength separation element for separating fluorescent wavelengths produced by the plural fluorescent labels, and plural detection elements for detecting individual fluorescent wavelengths separated by the wavelength separation element wherein the detection system and the plural detection elements are provided in the eyepiece of the endoscope.

The fourth type of the endoscope system of the present invention positions the detection system and plural detection elements at the endoscope eyepiece, which enables the distal end of the endoscope to be thin.

It is desirable in the second and fourth types of the endoscope system of the present invention that an objective optical system be provided at the endoscope tip, that the objective optical system has at least one filter, and a cut-off filter that blocks the excitation light wavelengths of the fluorescent labels. In such a case, visible and infrared components can be transmitted.

In the third and fourth types of the endoscope system of the present invention, the illumination system includes a light source. The light source is detachably provided with a filter that selectively transmits or reflects at least part of the wavelength range 600-2000 nm. The wavelength separation element separates plural fluorescent wavelengths individually when the filter is inserted. Furthermore, it is desirable in the third and fourth types of the endoscope system of the present invention that the wavelength separation element has an ability to separate at least three fluorescent wavelengths.

In the first through fourth types of the endoscope system of the present invention, the detection system is further provided with at least one filter which cuts off the wavelengths that excite the fluorescent labels but enables visible and infrared wavelengths of interest to be transmitted.

The first through fourth types of the endoscope system of the present invention further include an image processing device for merging a fluorescent image and a visible light observation image of the subject, and a monitor for displaying the merged image. The display of a merged fluorescent and visible light observation image allows the simultaneous observation of a fluorescent image and an ordinary observation image. Hence, the fluorescent image and ordinary observation image are obtained with no time lag, enabling the locating of the lesion in a simple and highly accurate manner.

It is desirable in the first and second types of the endoscope system of the present invention that the fluorescent labels be substances containing InAs nanocrystal. The wavelength separation element of the first through fourth embodiments of the endoscope system of the present invention is preferably an etalon. Using an etalon as a variable spectral transmittance element ensures that the fluorescent wavelengths produced by fluorescent labels are detected even if they have a Gaussian distribution in a narrow wavelength region.

It is desirable that the wavelength separation element consists of a tunable Fabry-Perot etalon filter comprising three or more aligned translucent substrates. Using three or more aligned translucent substrates enables the separation of fluorescent emissions having at least two wavelength peaks. However, the tunable Fabry-Perot etalon filter may be composed of only two aligned translucent substrates.

The present invention provides an endoscope system for observation and diagnosis of living tissue within a subject who has previously been administered plural fluorescent labels that emit different fluorescent wavelengths as a result, for example, of being formed of different materials.

It is desirable that the respective fluorescent labels have narrow fluorescent wavelength properties so that plural fluorescent labels can be introduced so as to increase the number of types of cancer-specific proteins detected for improved accuracy of diagnosis. Quantum dots (Q dots) can be used as the labels described above.

Figure 37:
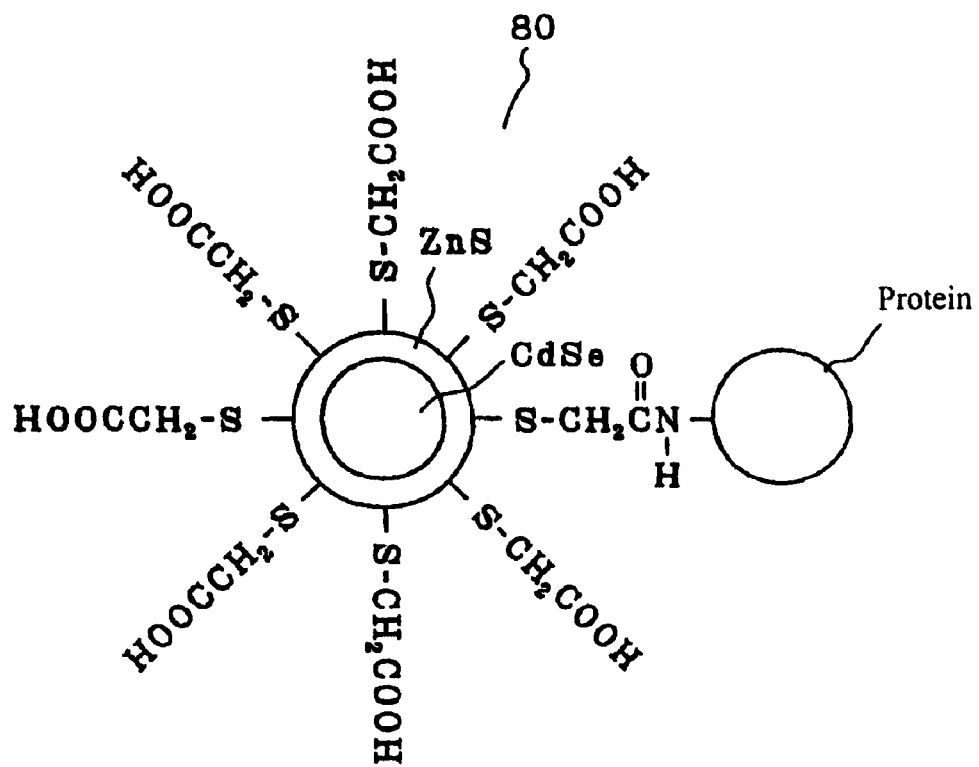
FIG. 37 is a prior art illustration to show an example of a quantum dot.

FIG. 37 is an illustration to show an example of a quantum dot. In FIG. 37, a quantum dot 80 has, for example, a semiconductor micro sphere formed of CdSe having a diameter of 2-5 nm as a nucleus, which is coated with ZnS in order to form a shell layer. Hydroxyl groups are attached to the shell layer via a sulfur molecule and thus proteins that target part of the hydroxyl group become bonded to the quantum dot.

Figure 38:
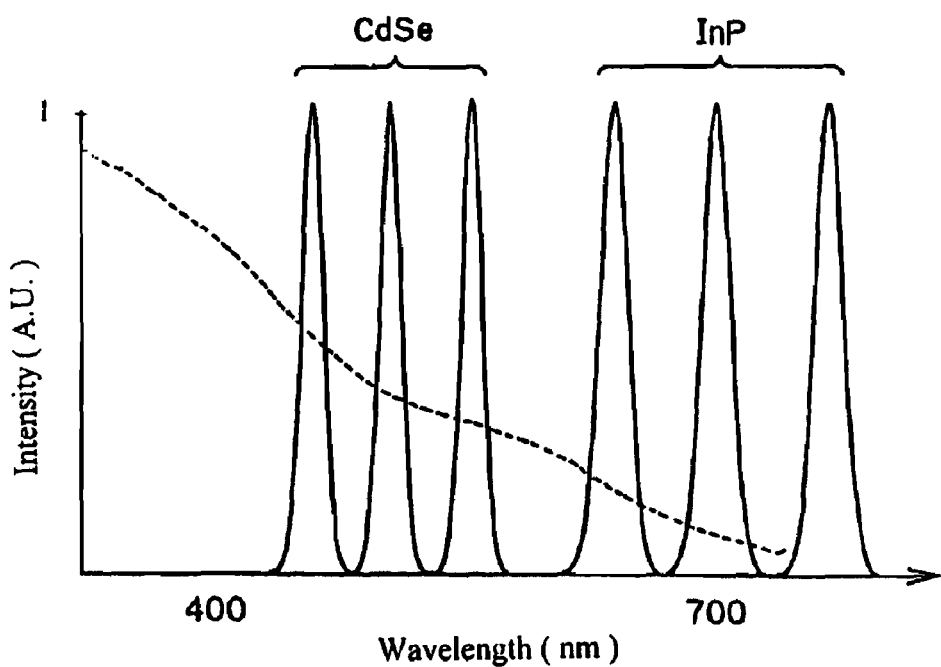
FIG. 38 is a graphical representation to show the excitation and emission spectra of the quantum dot shown in FIG. 37.

FIG. 38 shows the excitation light spectrum and the emission spectrum of a quantum dot. In FIG. 38, the broken line is the spectral distribution of the excitation light for a quantum dot and the solid line is the spectral distribution of the light emitted by a quantum dot that is formed of CdSe and InP. In order to distinguish different types of quantum dots, the quantum dots may have different particle sizes. As shown in FIG. 38, the excitation light wavelength distribution reaches to 700 nm. The quantum dot emits fluorescence in the near-infrared wavelength range. Quantum dots have the following characteristic fluorescent wavelength emission characteristics as compared to the prior art fluorescent dyes:

(1) the full band width of the emission spectrum profile of a quantum dot as measured at 50% of the peak intensity is about $1/200^{th}$ of the central wavelength of the spectrum (typically 20-30 nm) and is only about one-third that of a fluorescent dye;

(2) the peak wavelengths of the emission spectrum can be relatively flexibly selected in the range of approximately 400-2000 nm depending on the size (diameter) and material of the quantum dot, so as to create different, narrow-wavelength, Gaussian distributions; and (3) the excitation light spectrum is intensified at the shorter wavelengths within the visible to ultraviolet range regardless of the center wavelength of the emission spectrum.

When used for the detection of a single molecule, the quantum dots have the following advantages over conventional fluorescent dyes:

(1) they are very small in size and do not interfere with the movement of target molecules;

(2) their emission efficiency is much higher than that of conventional fluorescent dyes and thus, they allow highly sensitive detection of a single molecule; and (3) they are rarely discolored after an extended period of excitation.

According to these advantages, it is suitable to use fluorescent labels having the properties provided by quantum dots when conducting a single molecule detection analysis.

The quantum dots characteristically allow for relative flexibility in the selection of plural emission center wavelengths, depending on their particle size and the material used, and they have a narrow half band width emission spectrum. Thus, more types of molecules can be identified in a given usable wavelength range as compared with using conventional fluorescent dyes. Furthermore, quantum dots have a wider excitation light spectrum. Hence, plural different quantum dots can be excited at once using light in the visible and infrared range.

FIG. 1 shows the entire structure of a first embodiment of the endoscope system according to the present invention. In FIG. 1, an endoscope system 1 is formed of a light source system 2, an endoscope 3, a processor 5, and a monitor 6. This embodiment is characterized by having a structure that separates and detects plural fluorescent wavelengths within the endoscope tip.

FIG. 2 is an illustration that shows the structure of the light source optical system in the light source system 2 which can be used to detect fluorescent labels such as quantum dots (having, for example, emission spectra as shown in FIG. 38) that have previously been introduced into living tissue 4 to be examined with the endoscope system of the present invention. The light source optical system 2 is formed of a light source 21, a turret 22 provided with plural optical filters, and a rotational disk 23 provided with plural optical filters that are arranged concentrically. The light source 21 can be a Xenon lamp that includes light wavelengths in the visible range as well as in the excitation light wavelength range of the fluorescent labels.

Figure 3:
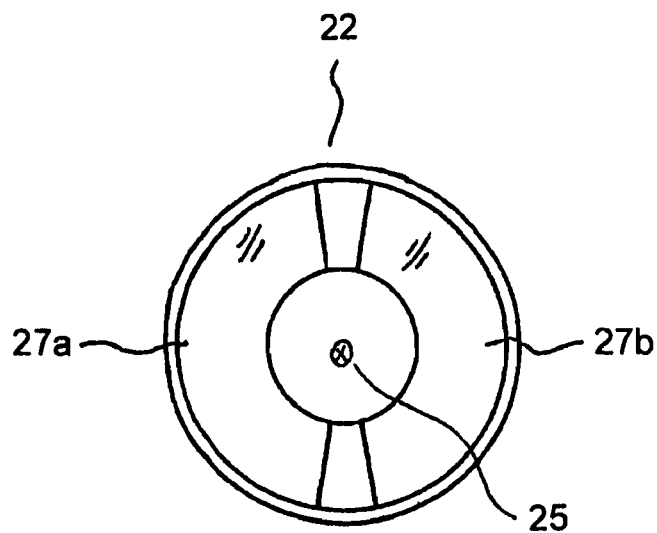
FIG. 3 is an end view of a turret 22 (also shown in FIG. 2) that is provided with two different band pass filters.

FIG. 3 is an end view of the turret 22 shown in FIG. 2. The turret is provided with two different band pass filters. The respective band pass filters have, for example, the spectral transmittances shown in FIG. 4.

Figure 4:
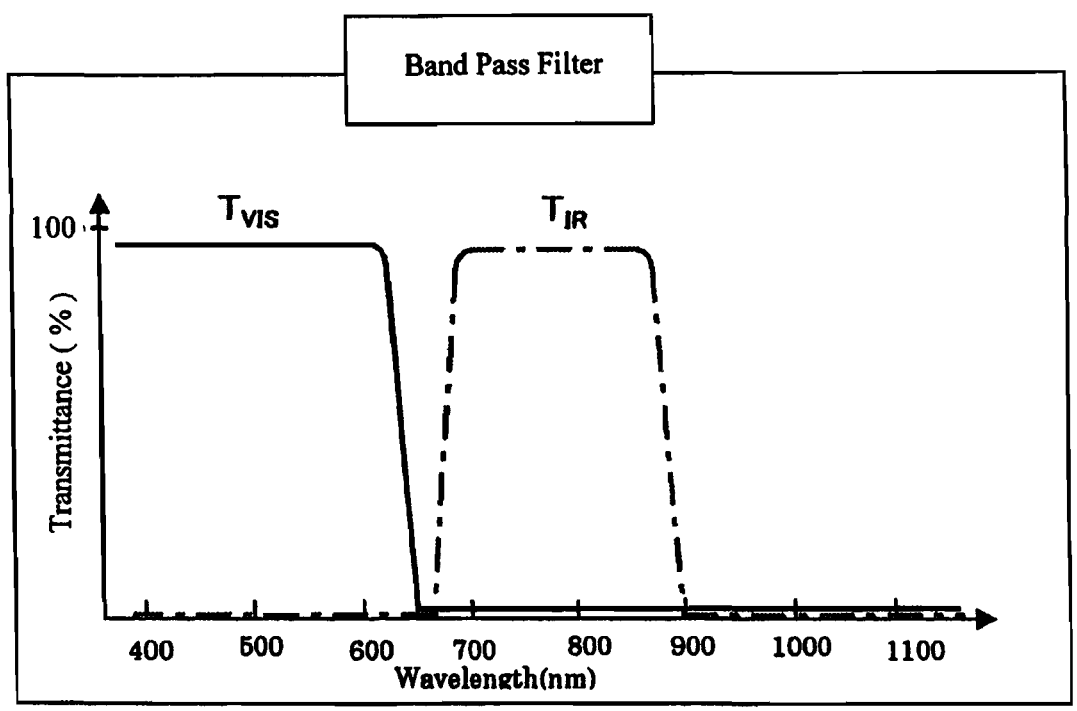
FIG. 4 shows the spectral transmittance of the band pass filter 27a of FIG. 3 that transmits primarily visible light (solid line) and of the band pass filter 27b of FIG. 3 that transmits primarily near-infrared light (dot-dash line)

FIG. 4 shows the spectral transmittance of a band pass filter 27a that transmits primarily visible light (solid line) and of a band pass filter 27b that transmits primarily near-infrared light (the dot-dash line). The turret 22 is rotated (as shown by the curved arrow R in FIG. 2) around the rotation axis 25 so as to insert one of the band pass filters into the optical path. The turret 22 is further provided with a mechanism (not shown) that moves the turret 22 in a direction orthogonal to the optical axis CL of the light source optical system.

Figure 5:
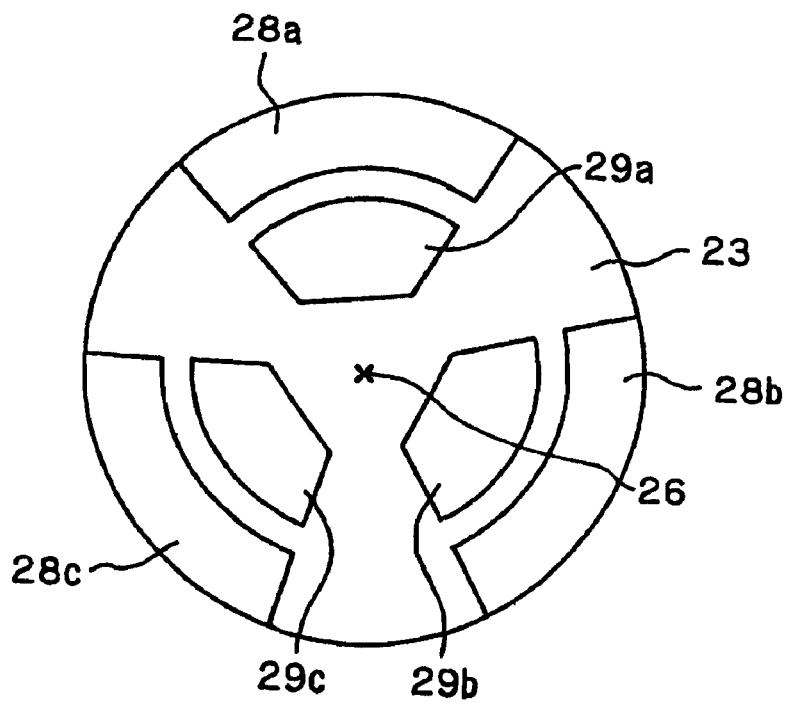
FIG. 5 shows a layout of windows that are provided on a rotational disk 23 of FIG. 2.

FIG. 5 shows a layout of windows that are provided on the rotational disk 23 around the rotation axis 26. The windows are provided concentrically spaced on the outer and inner regions of the disk. Optical filters are bonded and fixed to inner region windows 29a, 29b, and 29c, respectively. The rotational disk 23 is rotated around the rotation axis 26 at a fixed rotation speed. The rotational disk 23 is also moved by a rotational disk moving mechanism (not shown) so as to move the rotational disk 23 in a direction that is orthogonal to the optical axis CL of the light source optical system 2 (as shown by the double-headed arrow S).

After being moved by the rotational disk moving mechanism to a proper position, the rotational disk 23 can selectively create plural illumination modes. Table 1 below lists the illumination modes available using the light source optical system of this embodiment. A mode selection mechanism (not shown) is used to automatically select a given combination of the optical filter in the turret 22 and the window region formed in the rotational disk 23, as detailed in Table 1 below.

TABLE 1

| | Turret 22 | Rotational Disk 23 | illumination light |
|---|---|---|---|
| visible light mode: | 27a | 29a, 29b, 29c | visible light (B, G, R) |
| infrared mode: | 27b | 28a, 28b, 28c | infrared (excitation light) |

Figure 6:
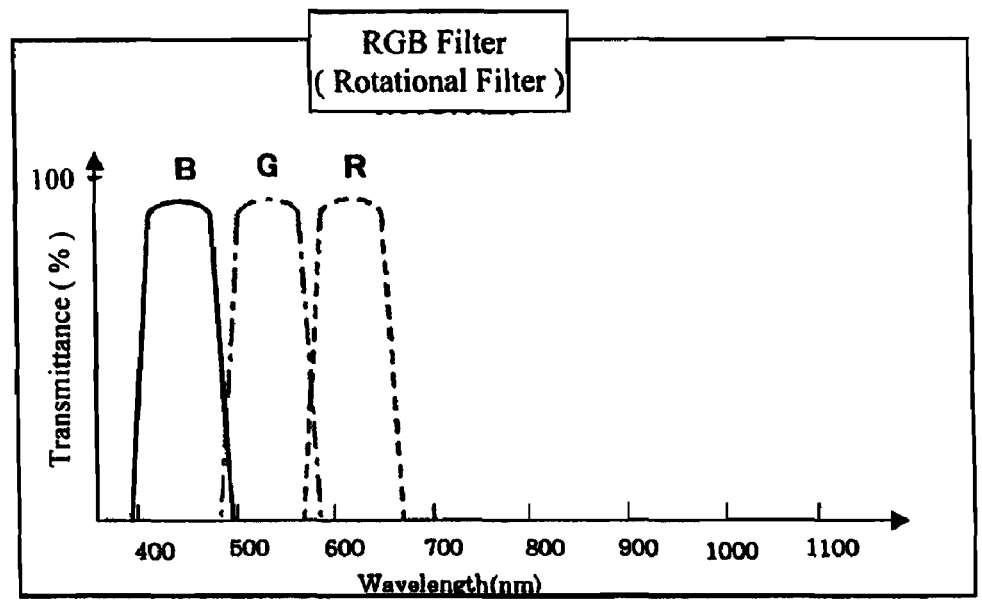
FIG. 6 shows exemplary spectral transmittances of optical filters that are attached to the inner windows of the rotational disk shown in FIG. 5.

FIG. 6 shows exemplary spectral transmittances of the optical filters attached to the inner windows of the rotational disk 23, with the band pass filter for transmitting blue light (B) being illustrated by a solid line, the band pass filter for transmitting green light (G) being illustrated by a dot-dash line, and the band pass filter for transmitting red light (R) being illustrated by a dash-dash line. When the turret 22 is rotated so as to insert the band pass filter 27a into the optical path, the rotational disk 23 is operated to sequentially insert the inner windows 29a, 29b, and 29c into the optical path so as to realize field sequential color illumination suitable for the endoscope system.

Figure 7:
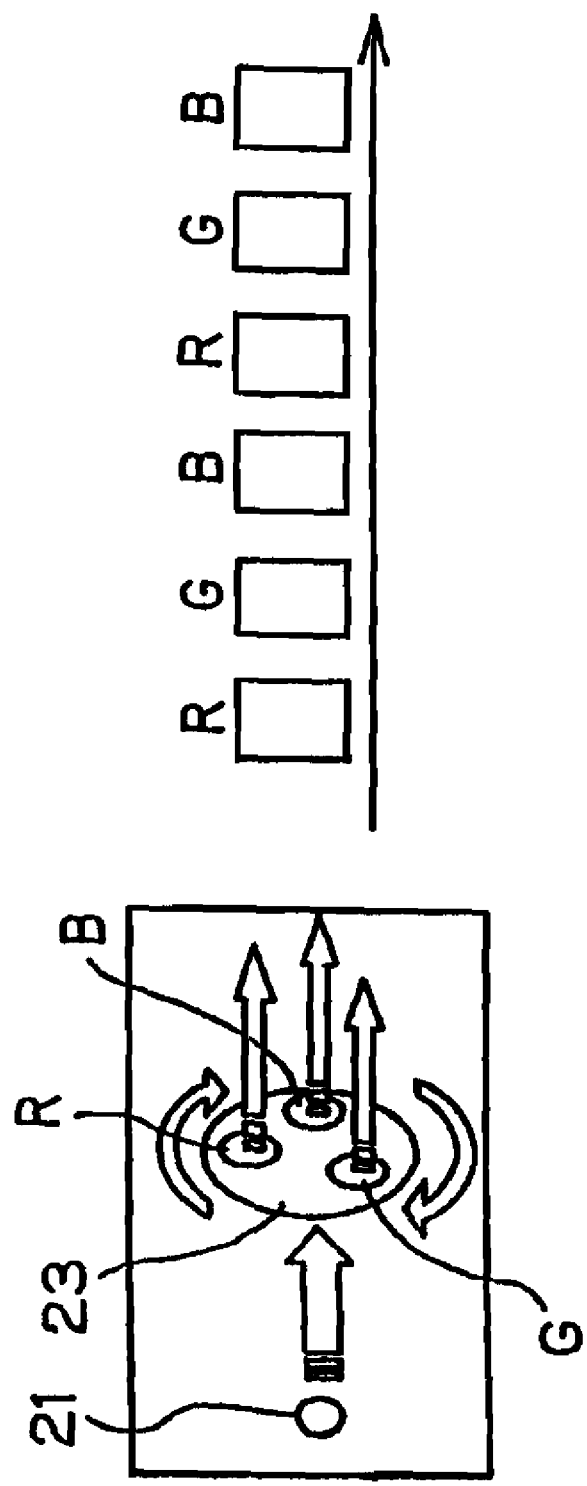
FIG. 7 is a schematic illustration that shows the illumination system.

FIG. 7 shows a manner of illumination by the illumination system. Among the light emitted from the light source 21, light mainly in the visible region having wavelengths λ in the range 400≦λ≦650 nm is selectively transmitted through the band pass filter 27a (not shown) and separated by the rotational disk into light of the blue B wavelength range, light of the green G wavelength range, and light of the red R wavelength range. Consequently, the three light colors R, G, and B are repeatedly and intermittently emitted. When the turret 22 is rotated so as to insert the band pass filter 27b into the optical path, the rotational disk 23 is operated so as to sequentially insert the outer windows 28a, 28b, and 28c into the optical path.

In this case, among the light emitted from the light source 21, light mainly in the near-infrared range is selectively transmitted through the band pass filter 27b, and then is repeatedly and intermittently transmitted by the rotational disk 23. Other, non-intermittent, illumination can be achieved by stopping the rotation of the rotational disk so as to keep any single window 28a, 28b, or 28c in the optical path, or by retracting the rotational disk from the optical path. As shown in FIG. 1, the illumination lens 32, the light guide fiber 31 as well as the reflected light receiving optics may be provided within the endoscope tip. Light produced by the light source 21 is transferred by the light guide fiber 31 so as to illuminate the living tissue 4 through the illumination lens 32.

Figure 8A:
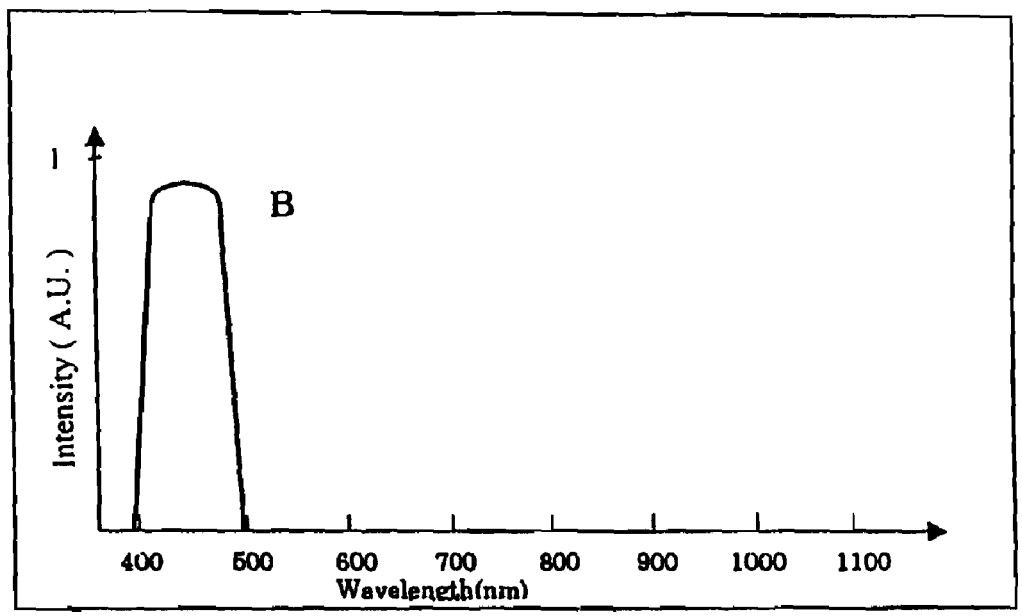
FIGS. 8(a)-8(d) show exemplary spectral intensity profiles of light for sequentially illuminating the living tissue 4 (illustrated in FIG. 1)
Figure 8B:
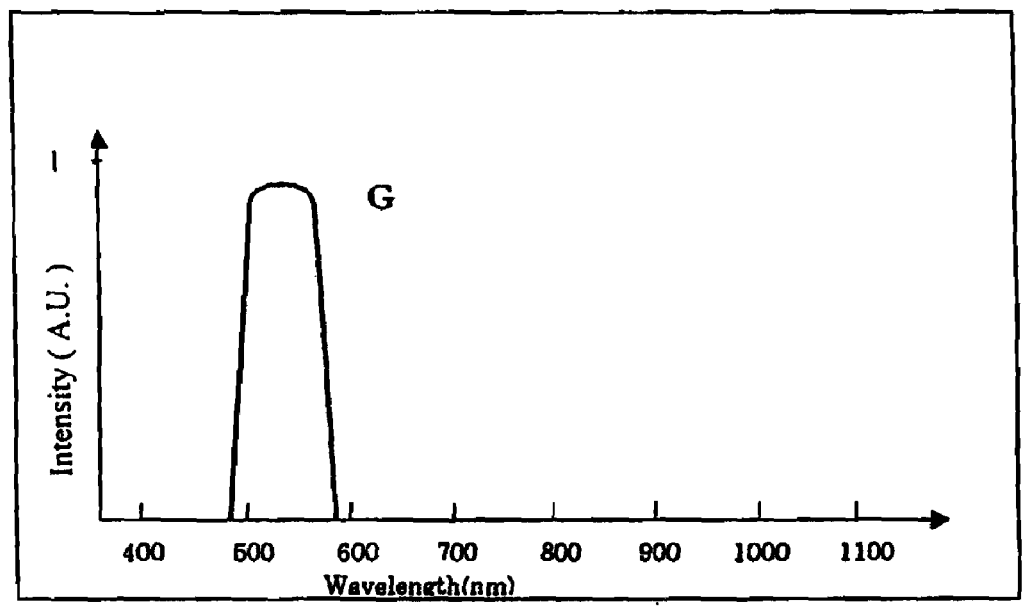
Figure 8C:
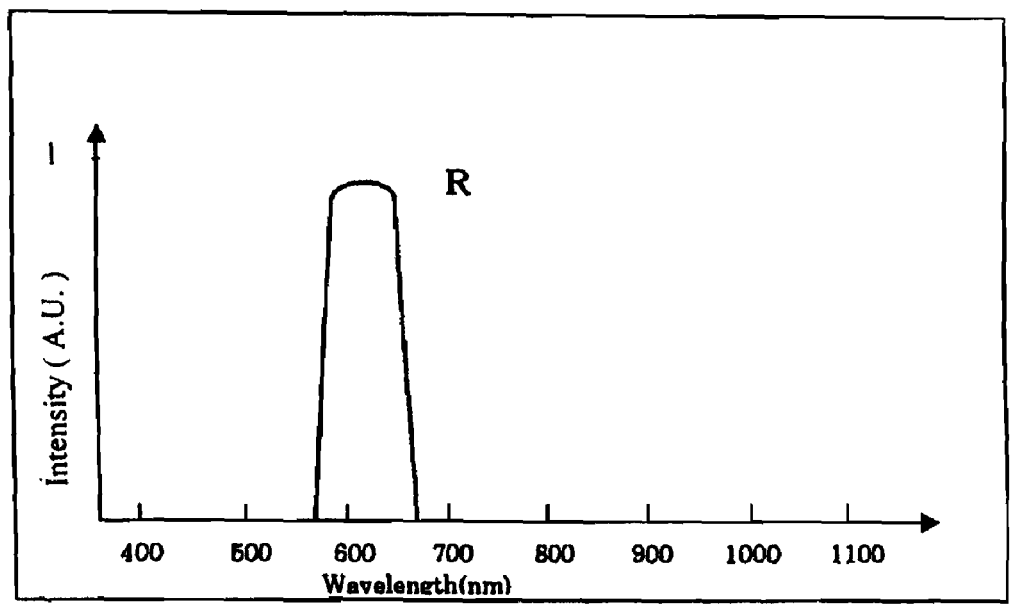
Figure 8D:
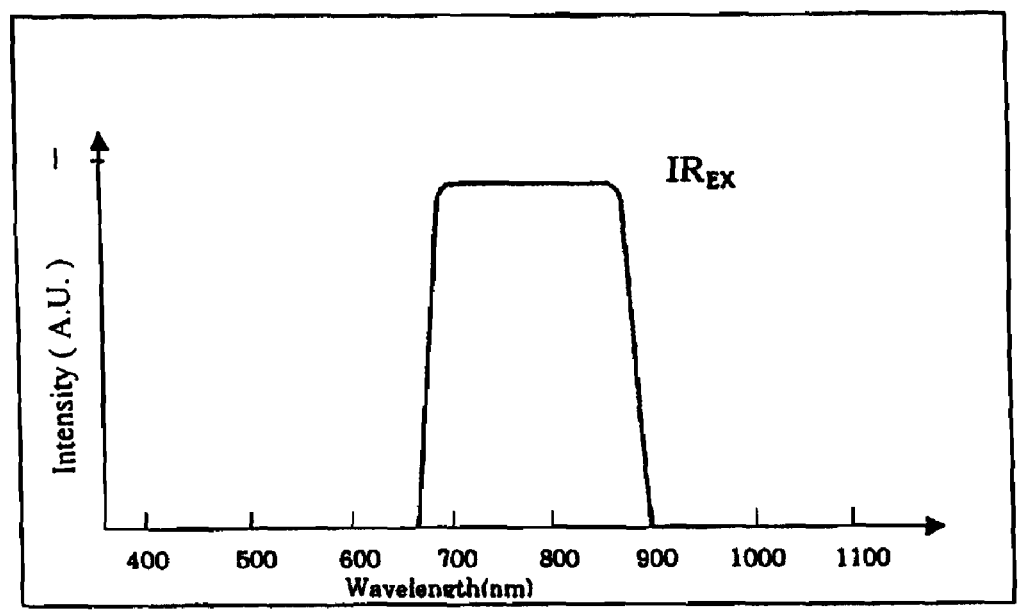

FIGS. 8(a)-8(d) show exemplary spectral intensity distributions of light illuminating the living tissue 4. More specifically, FIGS. 8(a)-8(c) show the spectral intensities in arbitrary units (A.U.) of light that sequentially illuminates the living tissue while the visible light mode is selected, and FIG. 8(d) shows the spectral intensity in arbitrary units (A.U.) of light that illuminates the living tissue while the infrared mode is selected.

Figure 9:
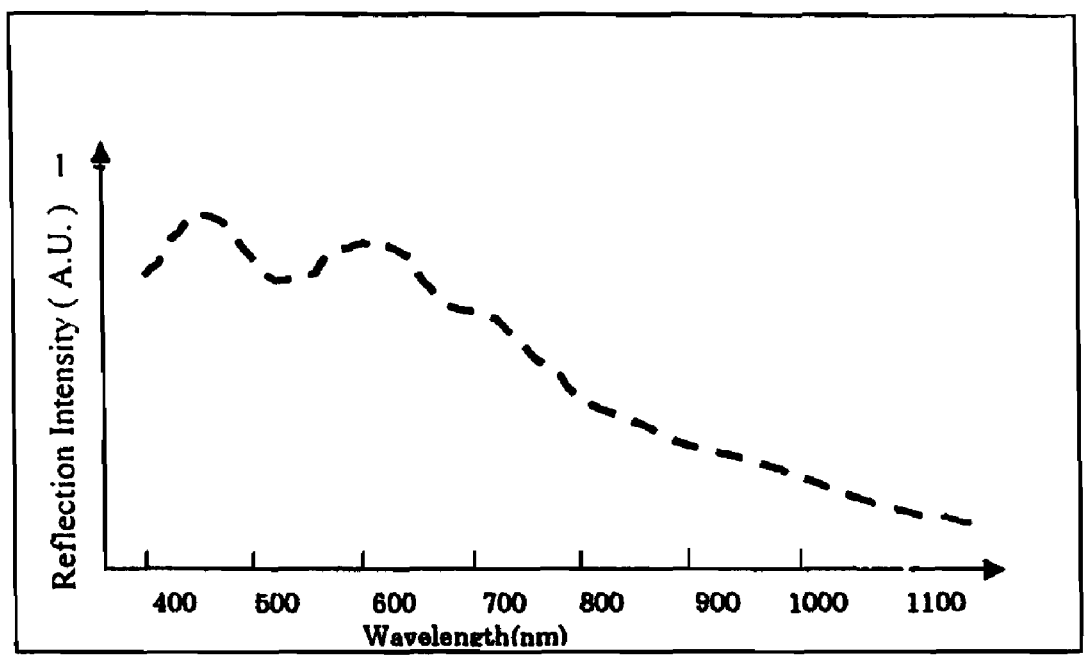
FIG. 9 illustrates the spectral reflectance of normal living tissue.

FIG. 9 shows the spectral reflectance for normal living tissue. In FIG. 9 the reflection intensity is plotted on the ordinate in arbitrary units (A.U.) and the wavelength (in nm) is plotted on the abscissa. Light in the red and infrared ranges is reflected and/or absorbed less by living tissue and thus reaches deep inside the living tissue as compared with the other visible light. Thus, light in the red and infrared ranges can excite the fluorescent labels wherever they are located within the living tissue, (i.e., on the surface or deep inside) and thus makes a proper excitation light. Taking into account the properties of the fluorescent labels, the excitation light can have a wavelength λ anywhere in the range 600≦λ≦2000 nm.

As shown in FIG. 1, an objective lens 33 is provided at the endoscope tip, adjacent to the illumination lens 32. The light receiving surface of a detector 36, such as a CCD, CMOS or another highly sensitive image pickup element, is provided at the image plane of the objective lens 33. An excitation light cut-off filter 34 having a fixed transmittance and a tunable filter 35 having a variable transmittance are provided between the objective lens 33 and the detector 36. A stop 37 is provided immediately following the objective lens 33.

Figure 10:
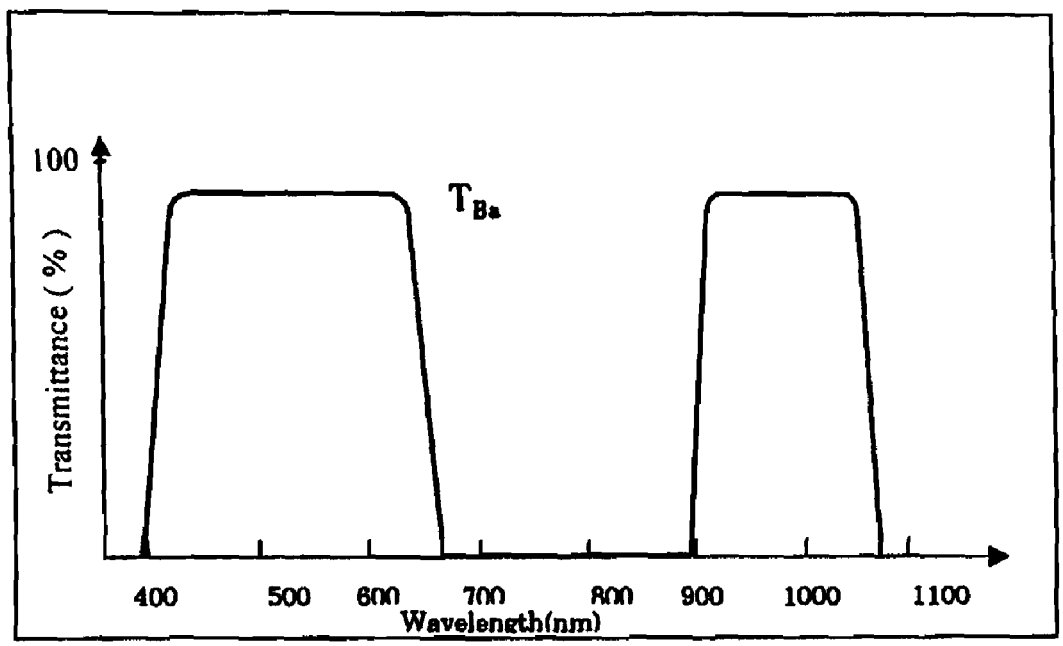
FIG. 10 shows the spectral transmittance of the excitation cut-off filter 34 (shown in FIG. 1)

FIG. 10 shows the percentage spectral transmittance of the excitation light cut-off filter 34. The excitation light cut-off filter 34 transmits visible light and the light in the fluorescent wavelength range of the fluorescent labels, and cuts off the light in the near-infrared range that excites the fluorescent labels. In most cases, the intensity of the fluorescence produced by the fluorescent labels is significantly low, less than $\frac{1}{1000}$, in comparison with the intensity of the excitation light. Thus, it is desirable that the excitation light cut-off filter 34 has a cut-off performance of OD4 or more, where OD stands for Optical Density and "OD4 or more" means that $\log_{10}(I/I') \geq 4$, where I is the intensity of light entering the filter, and I' is the intensity of light transmitted by the filter.

Providing a filter having such a cut-off performance prevents the excitation light from reaching the light receiving surface of the detector, and thus allows the detection of only the fluorescence so as to provide good contrast. It is desirable that the excitation light cut-off filter 34 be provided on the object side of the tunable filter 35. In this way, the excitation light that is reflected by the living tissue 4 is prevented from causing the tunable filter 35 to produce self-fluorescence, which can be a source of noise in the detection operation.

Figure 11A:
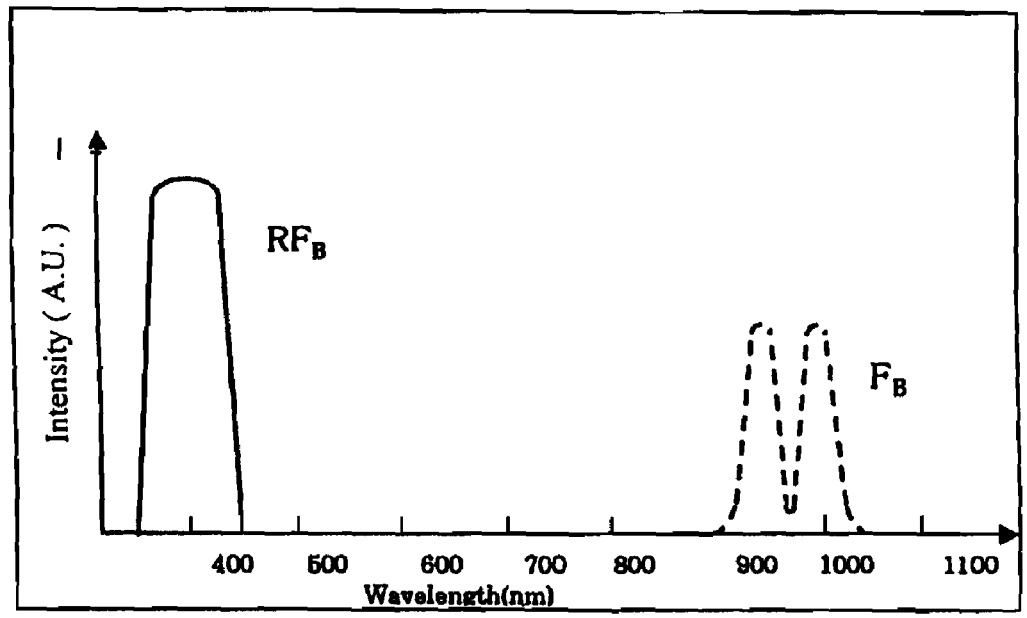
FIGS. 11(a)-11(d) show the spectral intensities of light entering the objective lens 33 (FIG. 1) from living tissue when illumination light as shown in FIGS. 8(a)-8(d) is irradiated onto the living tissue after fluorescent labels have been introduced into the living tissue.
Figure 11B:
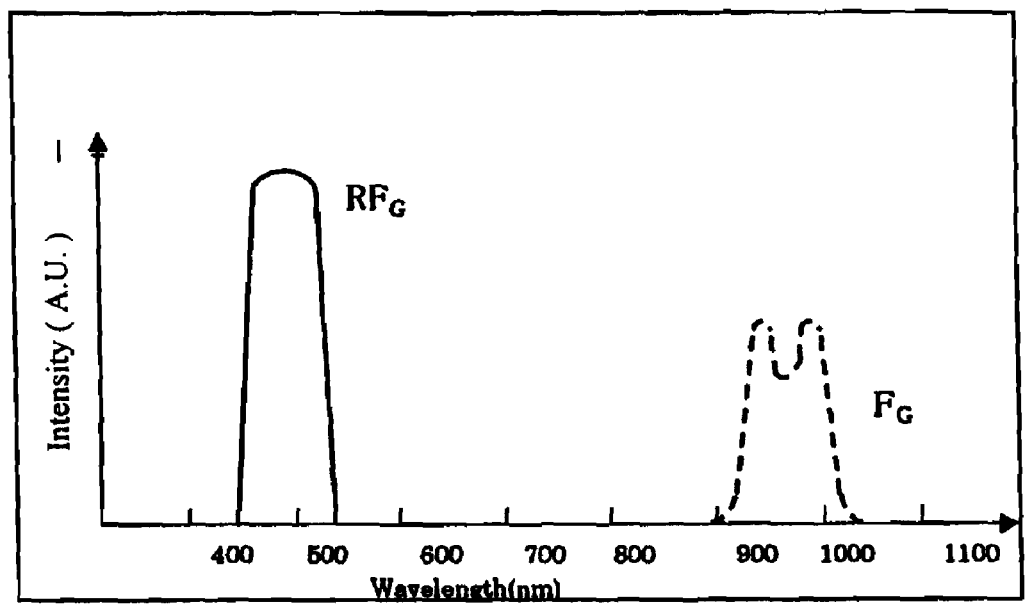
Figure 11C:
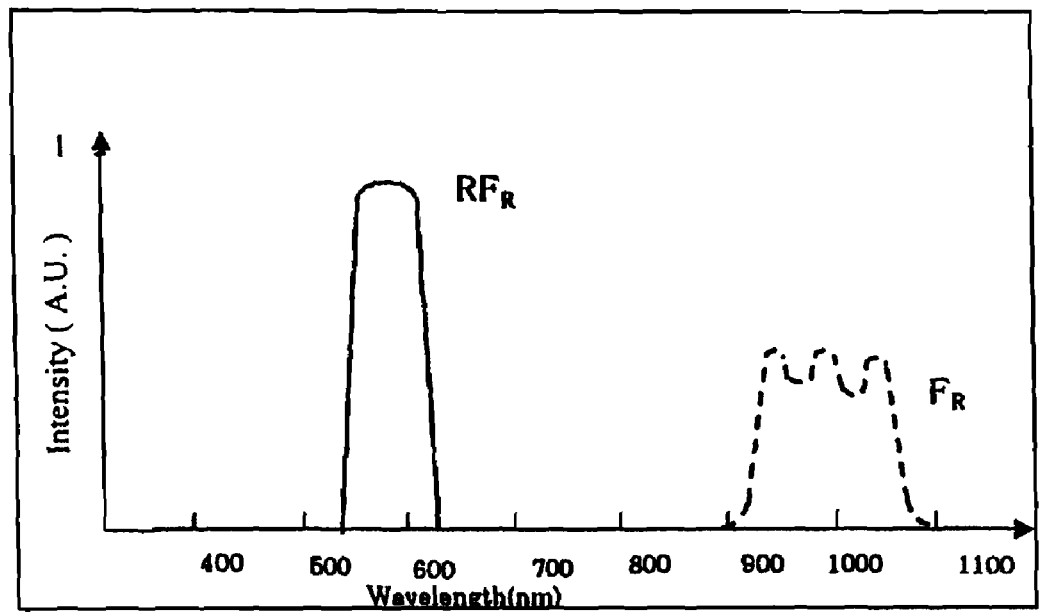

FIGS. 11(a)-11(d) show the spectral intensities in arbitrary units (A.U.) of light entering the objective lens 33 from the living tissue when the illumination light shown in FIGS. 8(a)-8(d) is irradiated onto living tissue that has had fluorescent labels introduced. The light entering the objective lens 33 includes two different components, namely, the light reflected by the living tissue (hereafter simply termed "reflected light", the intensity of which is shown by solid lines) and the fluorescence produced by the fluorescent labels (shown using dash-dash lines). In FIGS. 11(a)-11(d), although the spectral intensity curves of the reflected light and of the fluorescence are both shown in each figure, the intensity of the fluorescence has been greatly exaggerated for convenience of illustration. More particularly, FIGS. 11(a)-11(c) show the spectral intensities of light entering the objective lens 33 from the living tissue while the visible light mode is selected. The fluorescent labels can be excited by light in the visible range. Thus, in addition to the reflected light, fluorescence enters the objective lens 33. For example, when the blue illumination light is irradiated, as shown in FIG. 11(a), the reflected light carrying information from on and near the surface of the living tissue and the fluorescence from the fluorescent labels distributed on and near the surface layer of the living tissue enter the objective lens 33. Likewise, when green illumination light is irradiated, as shown in FIG. 11(b), the reflected light carrying information from the surface to a middle layer of the living tissue and the fluorescence from the fluorescent labels distributed from the surface to the middle layer of the living tissue enter the objective lens 33.

In addition to the fluorescence shown, the blue and green light induces self-fluorescence of the living tissue and the green to red light enters the objective lens 33. These light components are not shown in the figures. When the red illumination light is irradiated, as shown in FIG. 11(c), the reflected light carrying information from the surface to a relatively deep layer of the living tissue and the fluorescence from the fluorescent labels distributed from the surface to a relatively deep layer of the living tissue enter the objective lens 33.

Figure 11D:
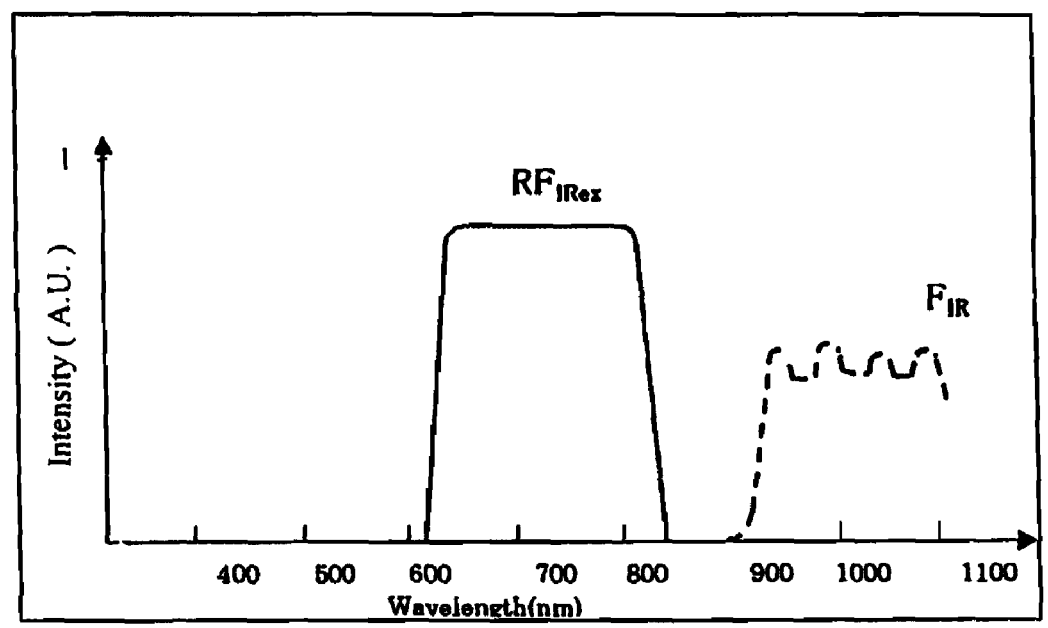

FIG. 11(d) shows the spectral intensity of light entering the objective lens 33 from the living tissue while the infrared mode is selected. When the illumination light in the red and near-infrared range having a relatively wide range of wavelengths $\lambda$ in the range $620 \leq \lambda \leq 830$ nm is irradiated, the reflected light carrying information on the deep layer of the living tissue and the fluorescence from the fluorescent labels distributed from the surface to a relatively deep layer of the living tissue all enter the objective lens 33.

Figure 12:
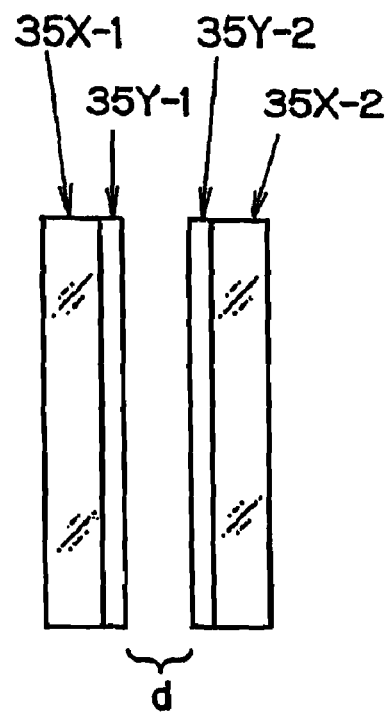
FIG. 12 shows the structure of a two-layer, tunable Fabry-Perot etalon filter.
Figure 13:
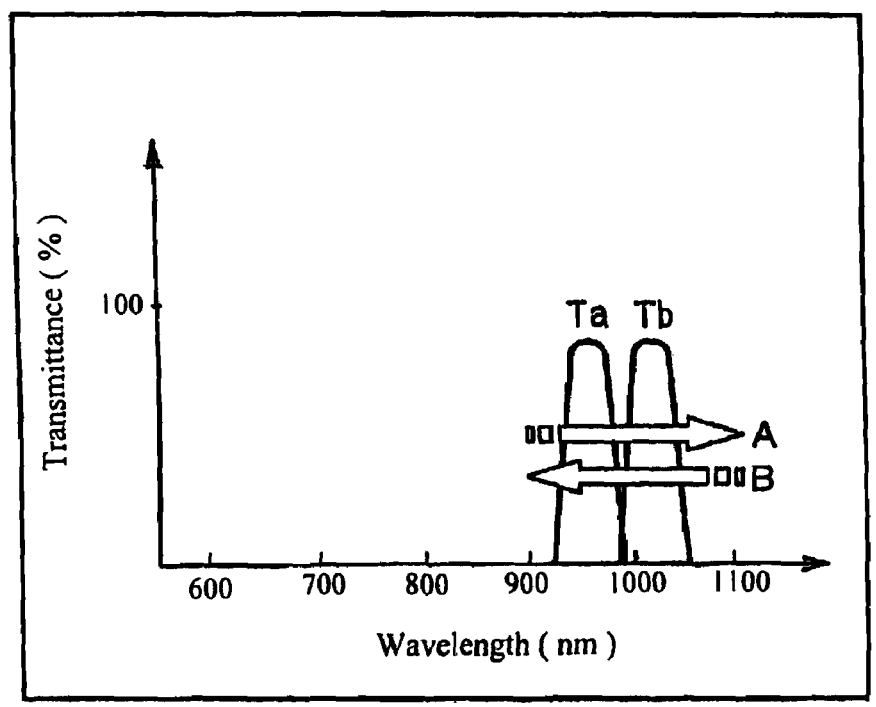
FIG. 13 shows the spectral transmittance of the tunable filter structure shown in FIG. 12.

The tunable filter that is used in this embodiment is a band pass filter of the tunable Fabry-Perot etalon type and has a transmittance wavelength range that may be varied. For example, the operation and structure of a two-layer, tunable Fabry-Perot etalon filter will now be described. FIG. 12 shows the structure of such a tunable filter and FIG. 13 shows the spectral transmittance of such a tunable filter.

As shown in FIG. 12, the tunable band pass filter is formed of two substrates 35X-1 and 35X-2, on the facing surfaces of which reflective coatings 35Y-1 and 35Y-2 are formed with an air gap d in-between. Light entering the substrate 35X-1 is subject to multiple reflections. The air gap distance d is changed so as to modify the peak wavelength transmittance that emerges from the substrate 35X-2. In other words, when the air gap distance d shown in FIG. 12 is changed, the wavelength of the maximum transmittance is changed from Ta to Tb, as shown in FIG. 13. The air gap distance d can be changed using a Piezo-electric element. The substrates can be made of transparent film and each has the same reflective property as either of the reflective coatings 35Y-1 and 35Y-2.

The term 'reflective coating' as used herein means a coating that exhibits a high reflectance (and thus low transmittance) to a range of wavelengths that includes the near-infrared range. Such a reflective coating can be formed of multiple laminated metal coatings (such as deposited silver) or from several to a score or more of laminated dielectric coatings. The tunable filter 35 that is provided between the objective lens 33 and detector 36 can distinguish among the different fluorescent labels by detecting specific ranges of wavelengths. The air gap distance is controlled in order to scan for the peak wavelengths of light transmitted through the tunable filter so that plural wavelengths in the near-infrared range can be separated for detection.

Figure 14:
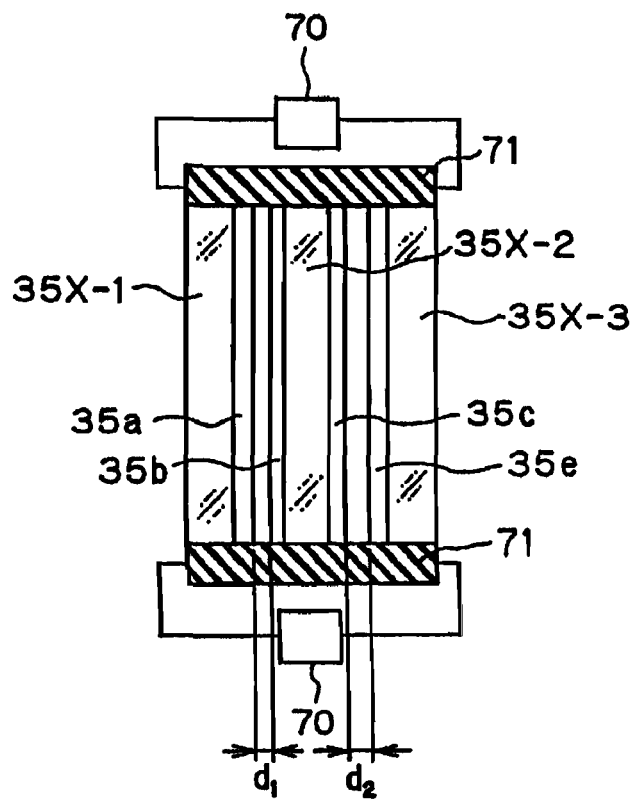
FIG. 14 is a cross-sectional view of a three-layer, tunable Fabry-Perot etalon filter.

The operation and structure of a three-layer, tunable Fabry-Perot etalon filter 35 will now be described. FIG. 14 shows a cross section of such a tunable band pass filter. In FIG. 14, glass substrates 35X-1, 35X-2, and 35X-3 have reflective coatings 35a, 35b, 35c, and 35e deposited on their facing surfaces. The reflective coatings 35a, 35b, 35c, and 35e are each formed of laminated metal coatings of, for example, deposited silver, or they may each be formed of several to as many as a score or more of laminated dielectric coatings.

FIG. 14 further shows air gaps $d_1$ and $d_2$, cylindrical laminated piezoelectric actuator elements 71, 71 fixed to the peripheries of the glass substrates 35X-1, 35X-2 and 35X-3, reflective coatings 35a, 35b, 35c, and 35e, and variable voltage power sources 70, 70 for applying voltage to the laminated piezoelectric actuator elements 71, 71. The laminated piezoelectric actuator elements 71,71 expand or contract in their axial direction (i.e., the horizontal direction of FIG. 14) in inverse proportion to the applied voltage so as to change the air gap distances $d_1$ and $d_2$ in a known manner. The top and bottom actuator elements 71, 71 in FIG. 14 independently control the air gaps $d_1$ and $d_2$.

The excitation light blocking property of the excitation light cut-off filter 34 can also be applied to the tunable filter 35. For example, an excitation light blocking (i.e., cut-off) coating can be applied to the substrate 35X-1 on the surface that is opposite the reflective coating 35a so that the excitation light cut-off filter 34 can be eliminated, thus saving space between the objective lens 33 and the detector 36.

Figure 15:
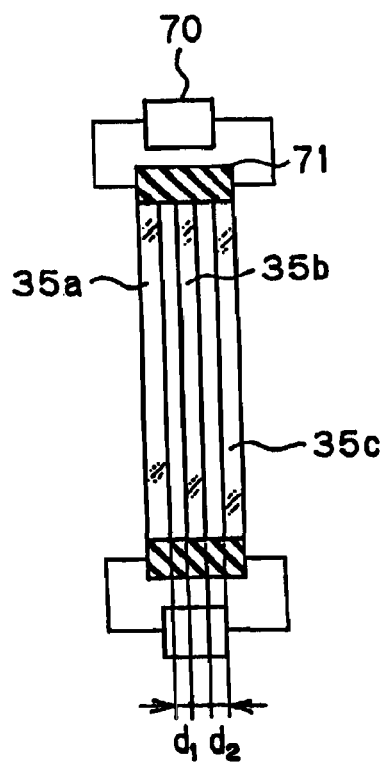
FIG. 15 is a cross-sectional view of another three-layer, tunable Fabry-Perot etalon filter.

FIG. 15 shows a cross section of another three-layer, tunable Fabry-Perot etalon filter in which the substrates are made of translucent film. This leads to reducing the weight, thus reducing the load of the air gap control devices such as the piezoelectric elements. This also contributes to higher response speeds and in saving power. The tunable Fabry-Perot etalon filter may be formed of plural layers that are constructed of substrates and reflective coatings, formed of only translucent films, or formed of a combination of these components so as to achieve a desired effect.

The endoscope system of the present invention guides the endoscope tip to a subject (living tissue) and enables color image observation of the subject using illumination light in the visible range. Thus, the tunable filter has to transmit the light in the visible range and scan for the fluorescence produced by the plural fluorescent labels in the near-infrared range.

The spectral transmittance required of a three-layer tunable filter that may be used in the endoscope system of the present invention will now be described with reference to FIGS. 16(a)-16(c). It is assumed here that the wavelengths of fluorescence from the fluorescent labels is in the range 900-1100 nm.

Figure 16A:
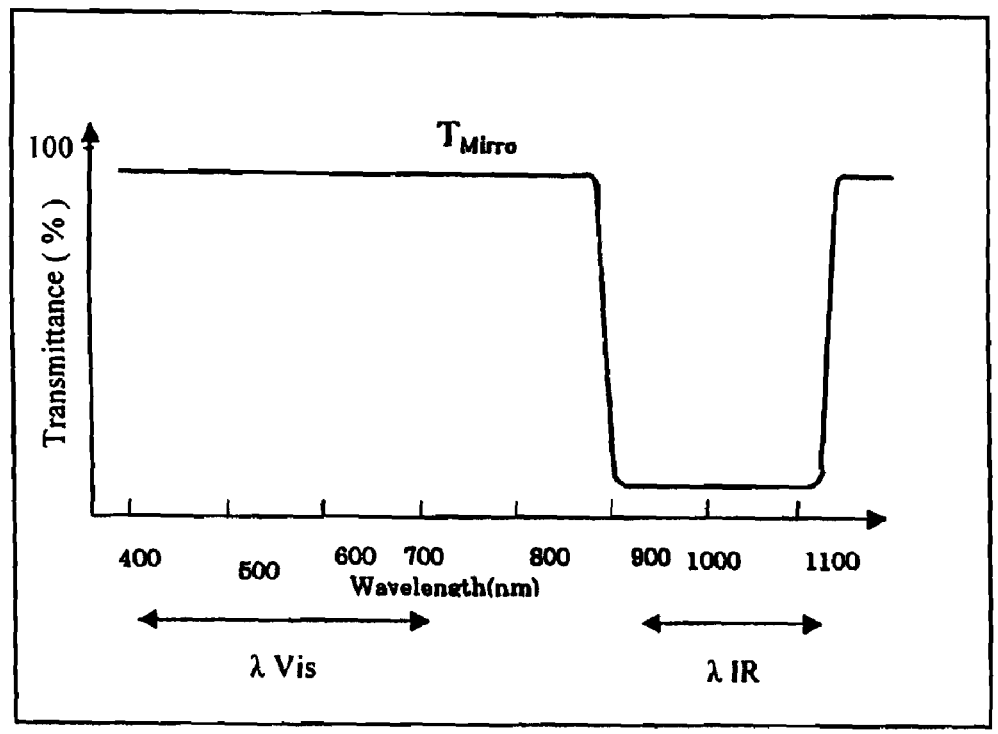
FIGS. 16(a)-16(c) show different spectral transmittances of a tunable filter 35 (shown in FIG. 1) that may be used in the endoscope system of the present invention.

FIG. 16(a) shows an exemplary spectral transmittance of the semi-transmitting coating deposited on the substrate forming an air gap. In this example, the coating exhibits a much reduced transmittance to the wavelengths λ in the range 900 nm≦λ≦1100 nm than to other wavelengths.

Figure 16B:
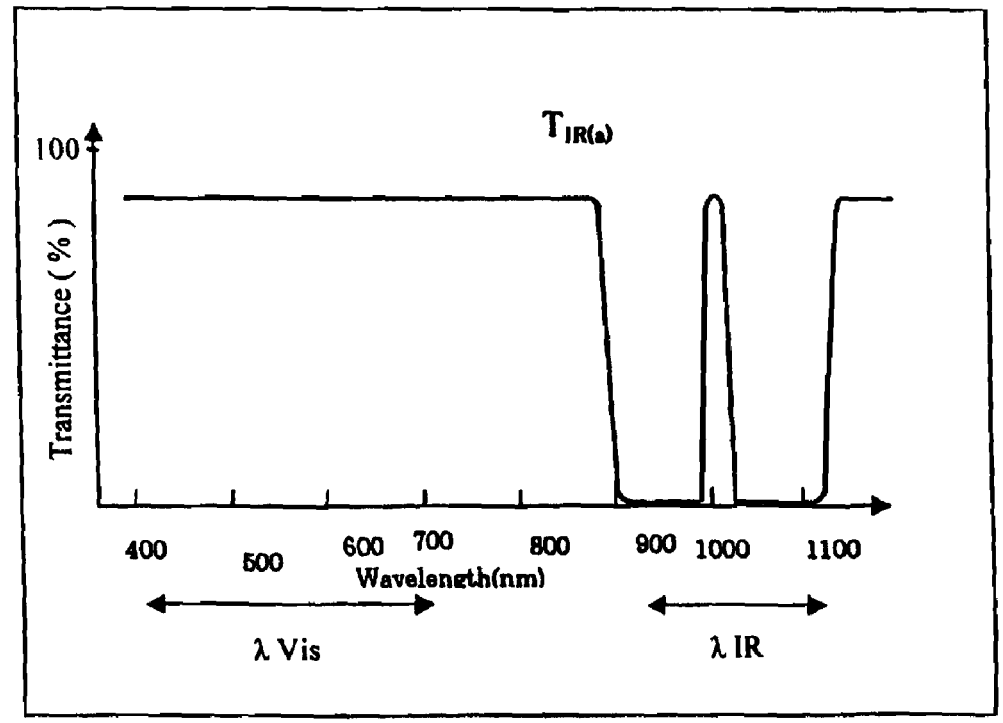

FIG. 16(b) shows the spectral transmittance of a tunable filter having an air gap distance A, with the light being subject to multiple interferences. As a result of multiple interferences of the light rays in the air gap, significantly narrow band pass regions occur in the range 900-1100 nm so as to enable the discerning of fluorescent emissions from the plural fluorescent labels. On the other hand, being scarcely subject to multiple interferences, light in the visible range is transmitted.

Figure 16C:
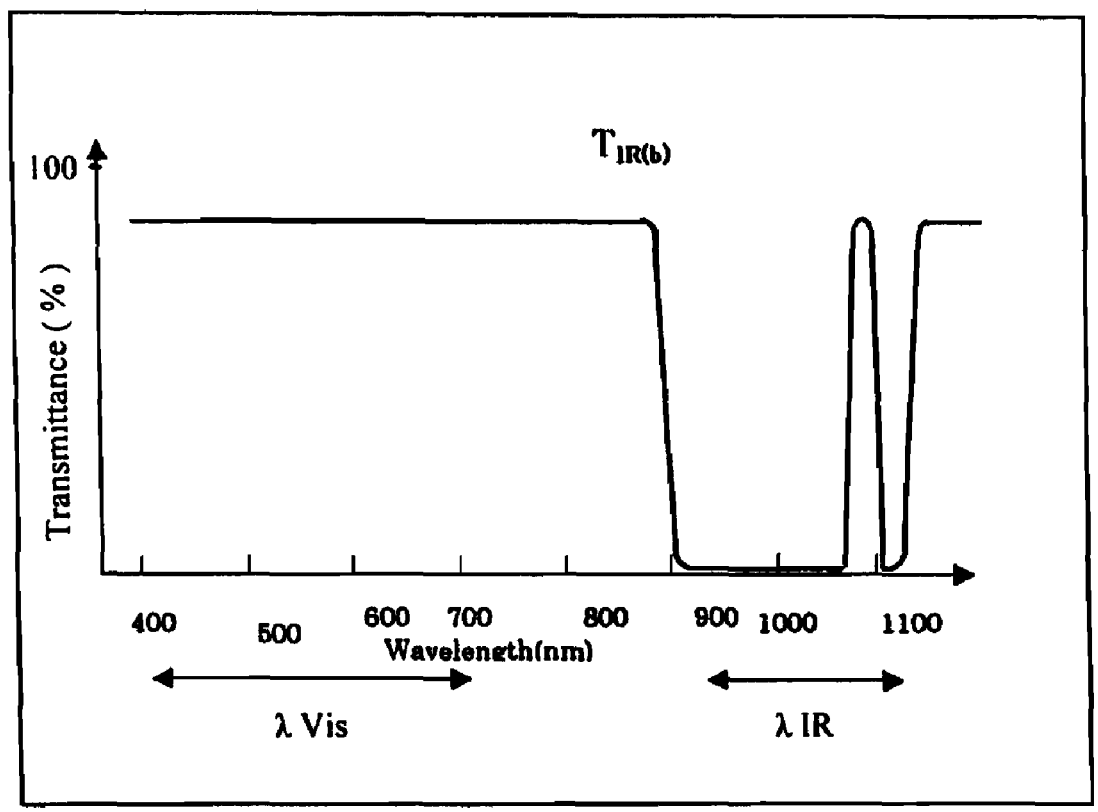

FIG. 16(c) shows the spectral transmittance of a tunable filter having an air gap distance B. Light is also subject to multiple interferences when the air gap distance is the distance B. The transmittance range is shifted according to the air gap distance within the range 900-1100 nm. However, no transmittance changes are observed for light in the visible range. The air gap distance can be changed to modify the transmittance of a desired range of wavelength and to maintain the transmittance of other wavelengths. To this end, the spectral transmittance of the semi-transmitting coating deposited on the substrate forming an air gap should be properly defined. It is desirable to use semi-transmitting coatings made of dielectric multi-layered coatings for obtaining the spectral transmittance described above.

FIGS. 17(a)-17(d) show the spectral intensities of the reflected light from the living tissue and the fluorescence from the fluorescent labels shown in FIGS. 11(a)-11(d) after the light has reached the light receiving surface of the detector 36 (i.e., after having been transmitted through the tunable filter 35 with a spectral transmittance as shown in FIGS. 16(a)-16(c)). In FIGS. 17(a)-17(d), the intensity is plotted on the ordinate in arbitrary units (A.U.) and the wavelength is plotted on the abscissa in units of nm. Once again, in FIGS. 17(a)-17(d), although the spectral intensity curves of the reflected light and of the fluorescence are both shown in each figure, the intensity of the fluorescence has been greatly exaggerated for convenience of illustration.

Figure 17A:
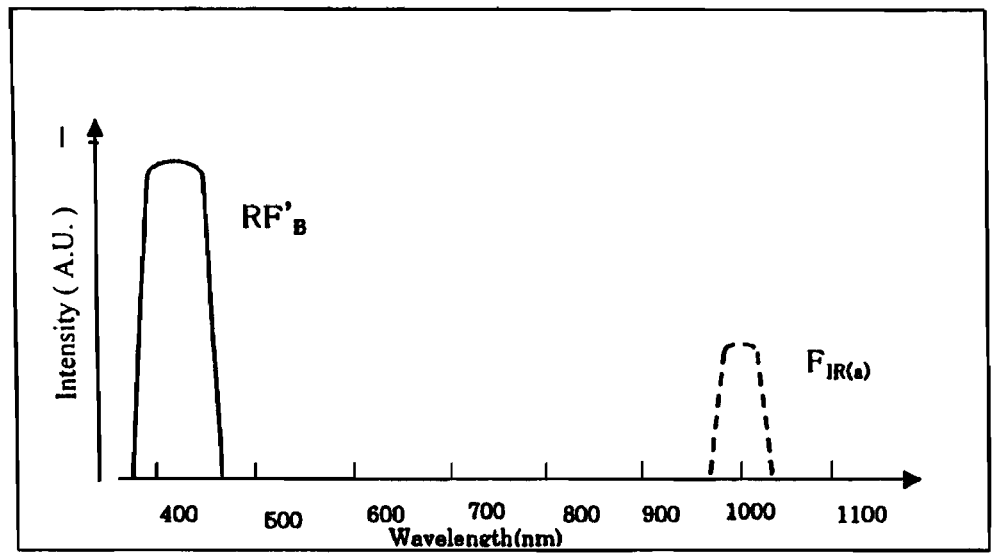
FIGS. 17(a)-17(c) show the spectral intensities of the blue, green, and red light, respectively, that has been reflected from living tissue and the fluorescent light emitted by the fluorescent labels (shown in FIGS. 11(a)-11(d)) when the light reaches the light receiving surface of the detector 36 (FIG. 1) after having been transmitted through the tunable filter 35.
Figure 17B:
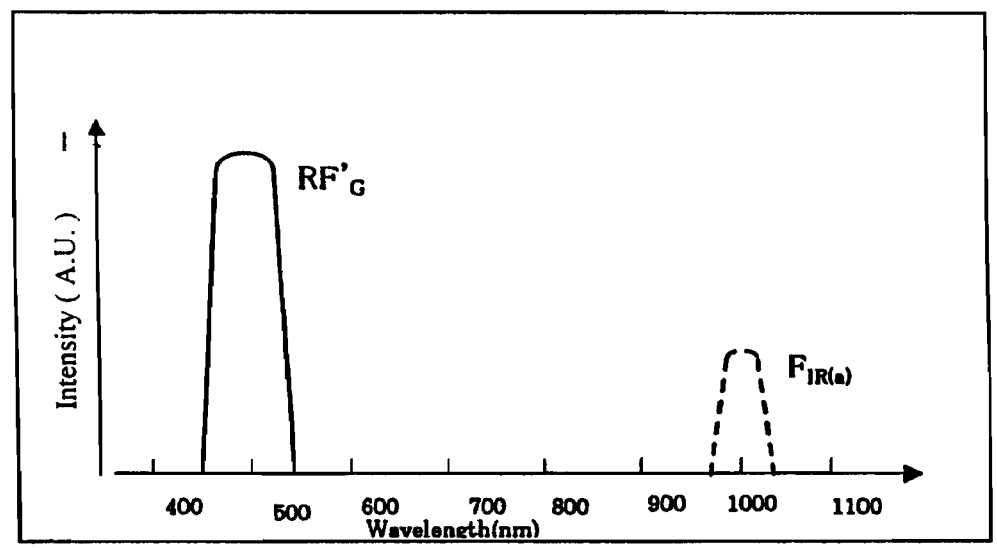
Figure 17C:
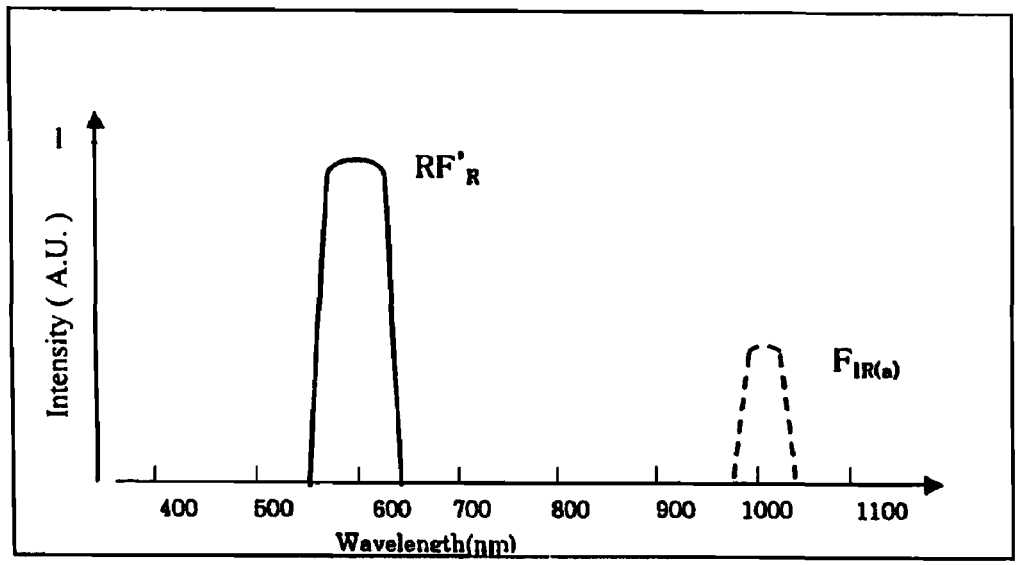

The tunable filter 35 transmits light in the visible range regardless of the air gap distance. Light in the blue (B), green (G) and red (R) wavelength ranges (as shown in FIGS. 17(a)-17(c), respectively) that is reflected from the living tissue always reaches the light receiving surface of the detector 36. On the other hand, among the light wavelengths in the range 900-1100 nm, light in a wavelength range having a peak near 1000 nm reaches the light receiving surface of the detector 36 when the air gap distance is the distance 'A'.

Figure 17D:
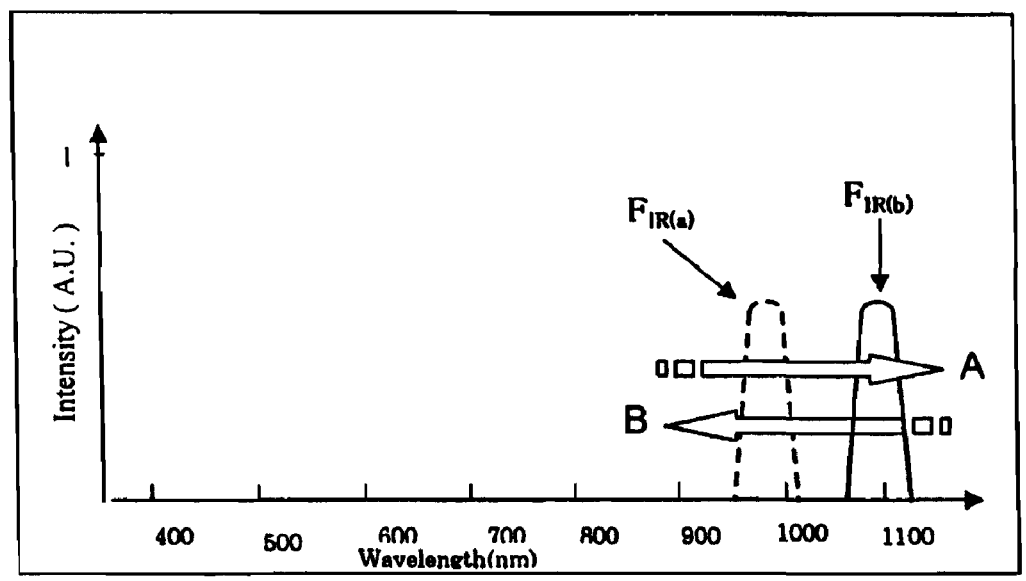
FIG. 17(d) shows the manner that plural fluorescent wavelengths in the infrared range are detected by scanning the transmission band pass wavelength of a tunable filter.

The fluorescence, because it has a significantly lower intensity than the reflected light, can be neglected in the R, G, B color image observation. Among the light entering the objective lens 33 from the living tissue while the infrared mode is selected, light in the near-infrared range that excites the fluorescent labels is cut off by the excitation light cut-off filter 34. As shown in FIG. 17(d), only the fluorescence reaches the light receiving surface of the detector 36. The air gap distance may be varied between the positions 'A' and 'B' so as to repeatedly scan the peak wavelengths in the direction indicated by the arrows. In this way, plural fluorescent wavelengths in the infrared range can be detected.

Figure 18A:
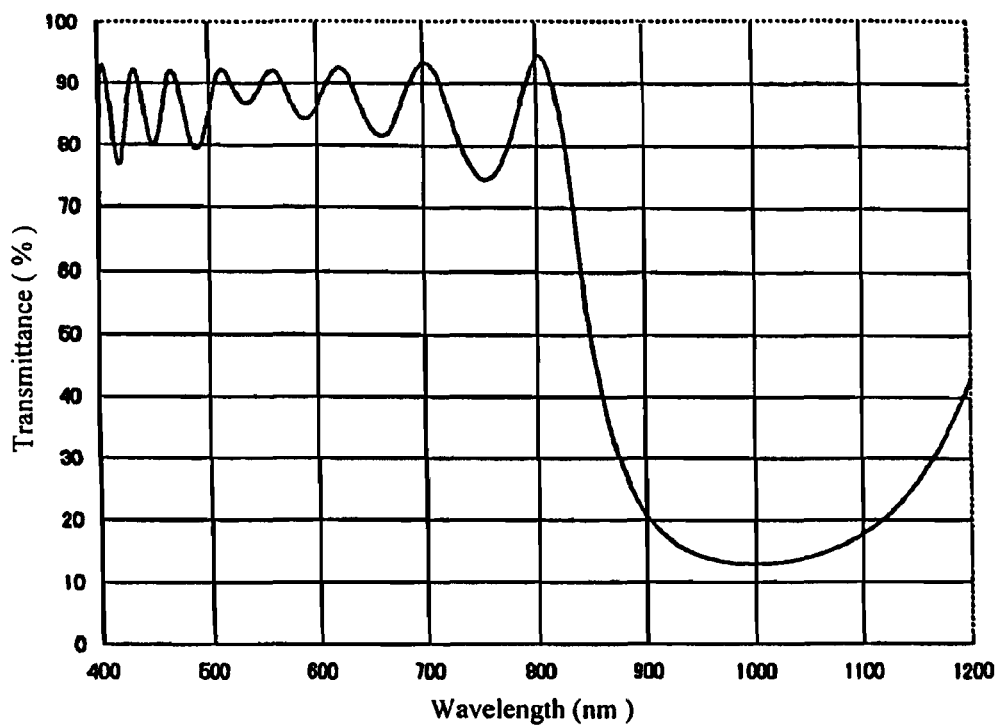
FIGS. 18(a)-18(d) relate to an exemplary design of a two-layer, tunable Fabry-Perot etalon filter, with FIG. 18(a) showing the spectral transmittance of a semi-transmitting coating deposited on the substrate surface that forms an air gap, and FIGS. 18(b)-18(d) showing the spectral transmittances of the tunable filter when the air gap distance d (shown in FIG. 12) is 375 nm, 500 nm, and 625 nm, respectively.

FIGS. 18(a)-18(d) show the spectral transmittances relating to a two-layer, tunable Fabry-Perot etalon filter that is designed for when the fluorescent emission wavelength peaks are in the wavelength range of 950-1050 nm. FIG. 18(a) shows the spectral transmittance of a semi-transmitting coating deposited on the substrate surfaces that form an air gap. In this case, the spectral transmittance of the semi-transmitting coating satisfies the following conditions:

$T1 \geq 80\%$  Condition (1)

$T2 \leq 20\%$  Condition (2)

where

T1 is the average transmittance in the wavelength region of 400 nm≦λ≦650 nm, and T2 is a transmittance in a wavelength band having a lower boundary that is 50 nm shorter than the peak transmittance wavelength of the shortest fluorescence wavelength, and an upper boundary that is 50 nm longer than the peak transmittance wavelength of the longest fluorescence wavelength.

Figure 18B:
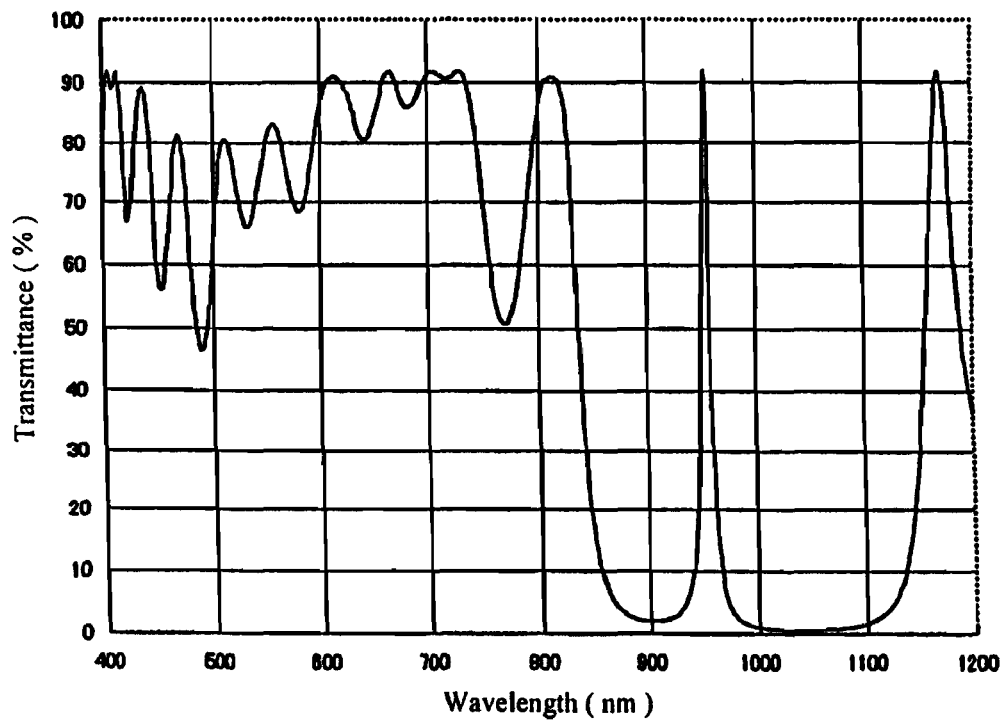
Figure 18C:
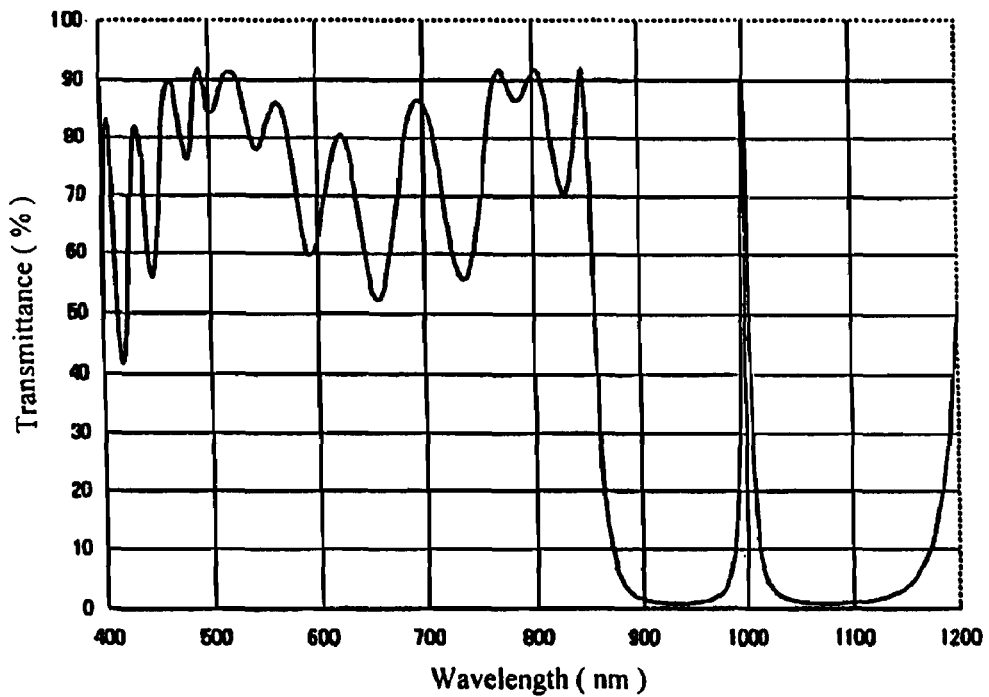
Figure 18D:
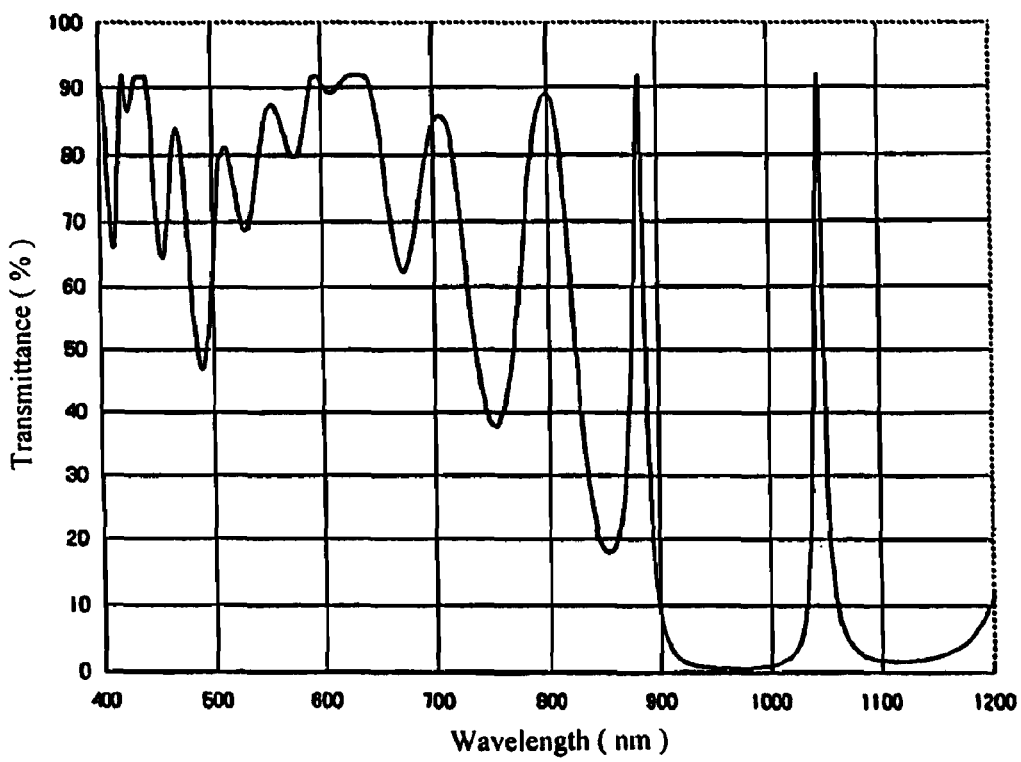

FIGS. 18(b)-18(d) show the spectral transmittances of the tunable filter when the air gap distance d is 375 nm, 500 nm, and 625 nm, respectively. A transmission range having a half band width of only 15 nm is established within the wavelength range 900-1100 nm, and an average transmittance of 70% or more is ensured for the visible range. FIG. 18(b) shows the spectral transmittance of the tunable filter with d=375 nm. In this case, the transmission wavelength peak is at 950 nm, and the transmittance is 3% or less in the approximate ranges 900-930 nm and 970-1100 nm.

FIG. 18(c) shows the spectral transmittance of the tunable filter with d=500 nm. In this case, there is a narrow band width transmission peak at λ=1000 nm. The transmittance is 3% or less in the wavelength ranges 900-980 nm and 1020-1100 nm. FIG. 18(d) shows the spectral transmittance of the tunable filter with d=625 nm. In this case, the transmission wavelengths have a peak at 1050 nm, and the transmittance is 3% or less in the wavelength ranges 900-1030 nm and 1070-1100 nm.

An appropriate spectral transmittance of the tunable filter for separating plural fluorescent wavelengths for detection can be obtained by setting the transmittance of the semi-transmitting coating to be 20% or less in the wavelength range extended by at least 50 nm with respect to the range defined by the shortest fluorescent wavelength peak and the longest fluorescent wavelength peak used. The air gap d is fixed at an appropriate distance for RGB color image observation.

Figure 49A:
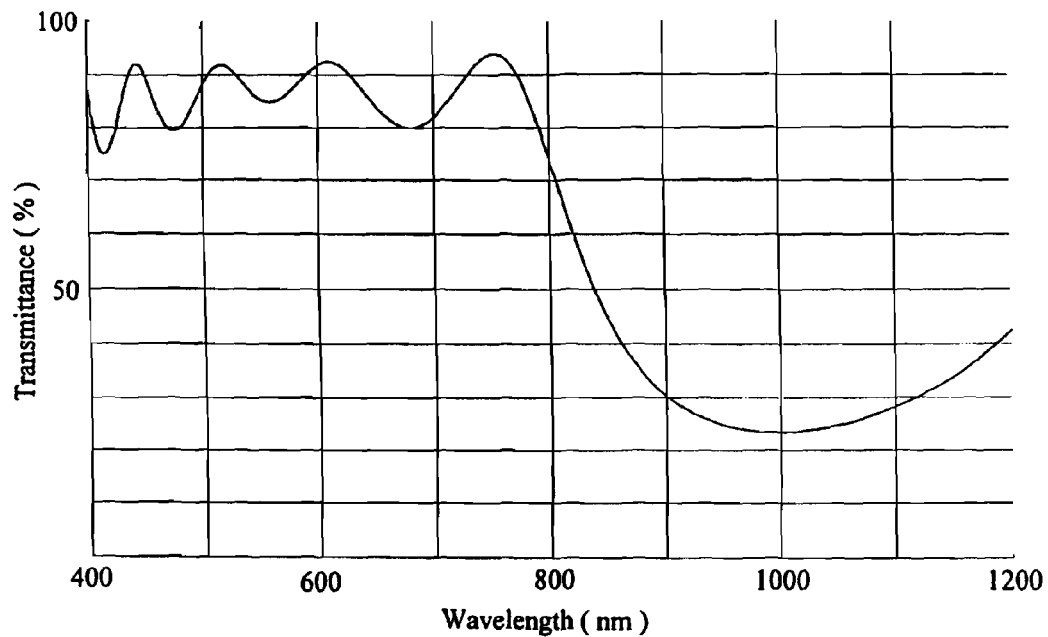
FIGS. 49(a)-49(d) show the spectral transmittances relating to a two-layer, tunable Fabry-Perot etalon filter.

FIGS. 49(a)-49(d) show the spectral transmittances relating to a two-layer, tunable Fabry-Perot etalon filter that is designed for when the fluorescent emission wavelength peaks are in the wavelength range of 950-1050 nm and that has different transmittance properties from those shown in FIGS. 18(a)-18(d). FIG. 49(a) shows the spectral transmittance of a semi-transmitting coating deposited on the substrate surfaces that form an air gap. In this case, the spectral transmittance of the semi-transmitting coating satisfies the following conditions:

$$T1 \geq 80\% \qquad \text{Condition (1)}$$

$$T2 \leq 35\% \qquad \text{Condition (2')}$$

where

T1 is the average transmittance in the wavelength region of 400 nm$\leq \lambda \leq$650 nm, and T2 is a transmittance in the wavelength band having a lower boundary that is 50 nm shorter than the peak transmittance wavelength of the shortest fluorescence wavelength, and an upper boundary that is 50 nm longer than the peak transmittance wavelength of the longest fluorescence wavelength.

Figure 49B:
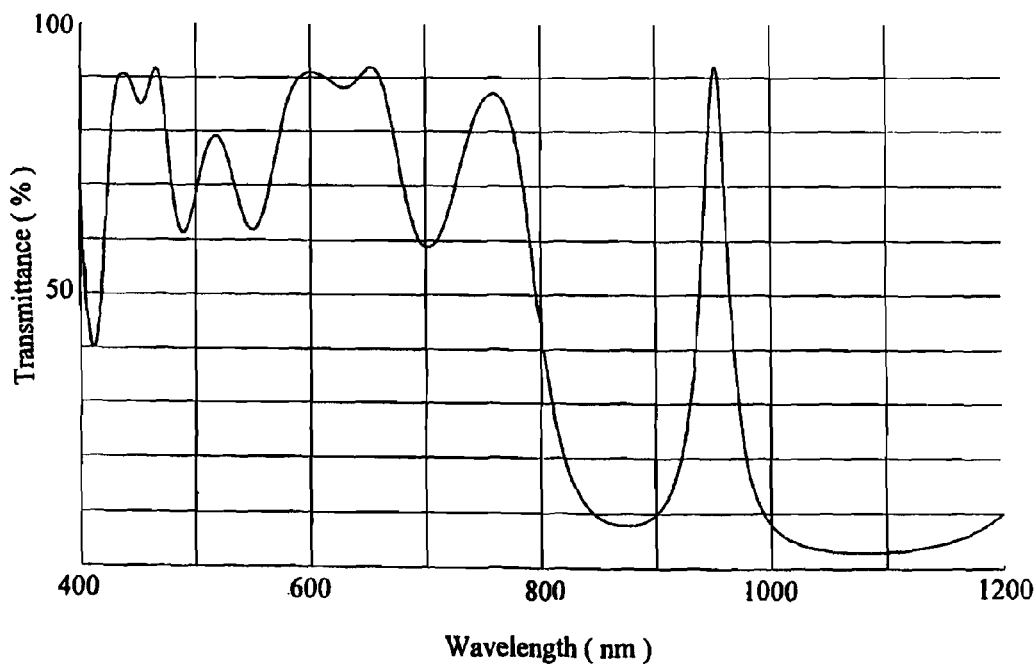
Figure 49C:
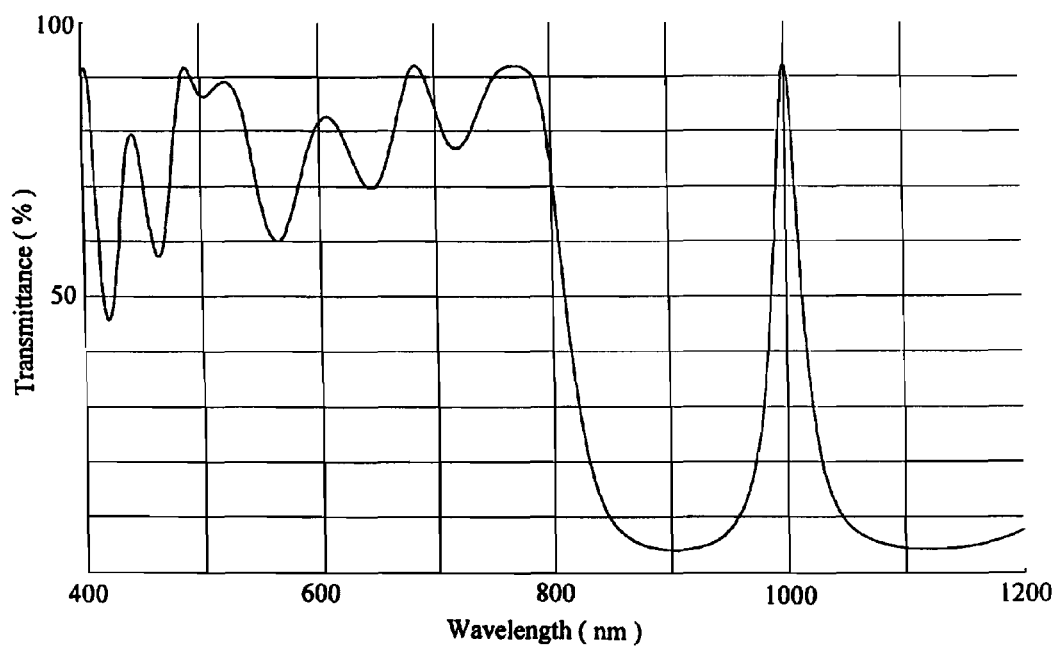
Figure 49D:
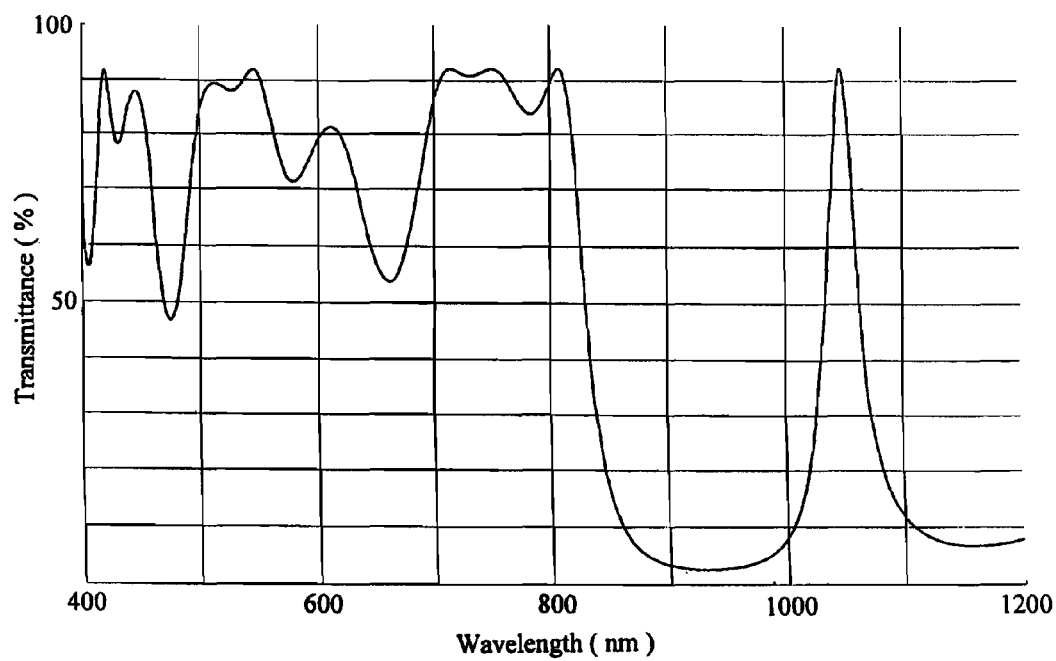

FIGS. 49(b)-49(d) show the spectral transmittances of the tunable filter when the air gap distance d is 925 nm, 1000 nm, and 1075 nm, respectively. A transmission range having a half band width of only 30 nm is established within the wavelength range 900-1100 nm, and an average transmittance of 70% or more is ensured for the visible range. FIG. 49(b) shows the spectral transmittance of the tunable filter with d=925 nm. In this case, the transmission wavelength peak is at 950 nm.

FIG. 49(c) shows the spectral transmittance of the tunable filter with d=1000 nm. In this case, there is a narrow band width transmission peak at λ=1000 nm. FIG. 49(d) shows the spectral transmittance of the tunable filter with d=1075 nm. In this case, the transmission wavelengths have a peak at 1050 nm.

The tunable filter having a transmittance property mentioned above has a wider half band width than the tunable filter having the transmittance property shown in FIGS. 18(a)-18(d), in the wavelength region of 900 nm-1100 nm. This causes the amount of fluorescent light passing through the tunable filter to increase and serves to achieve both separation of the plural fluorescent lights and detection of the brighter fluorescent images.

Figure 48A:
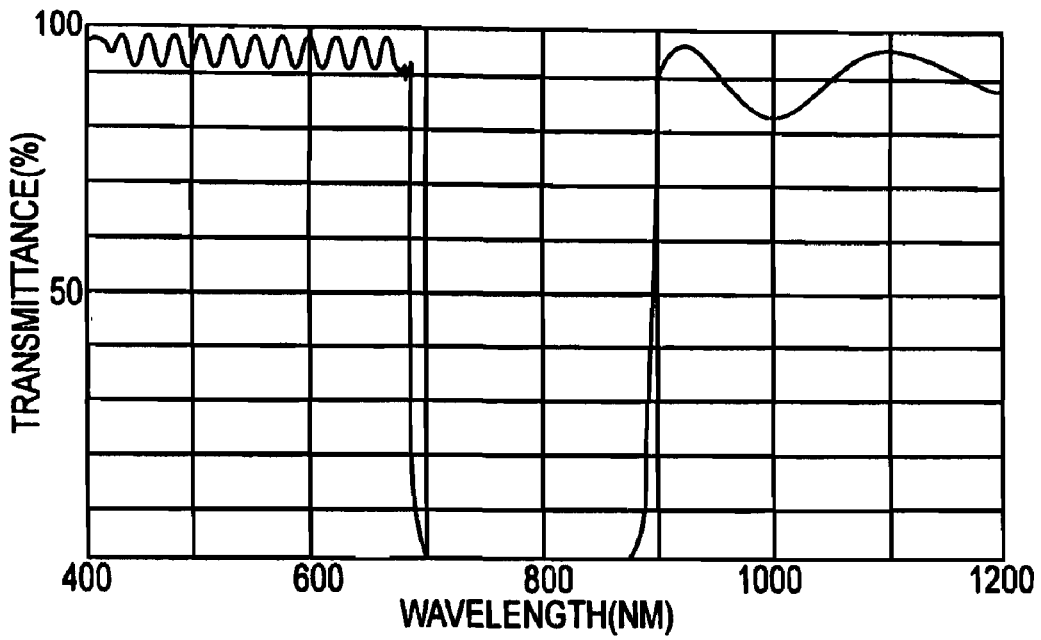
FIG. 48(a) shows the spectral transmittance of an excitation light cut-off filter 34.
Figure 48B:
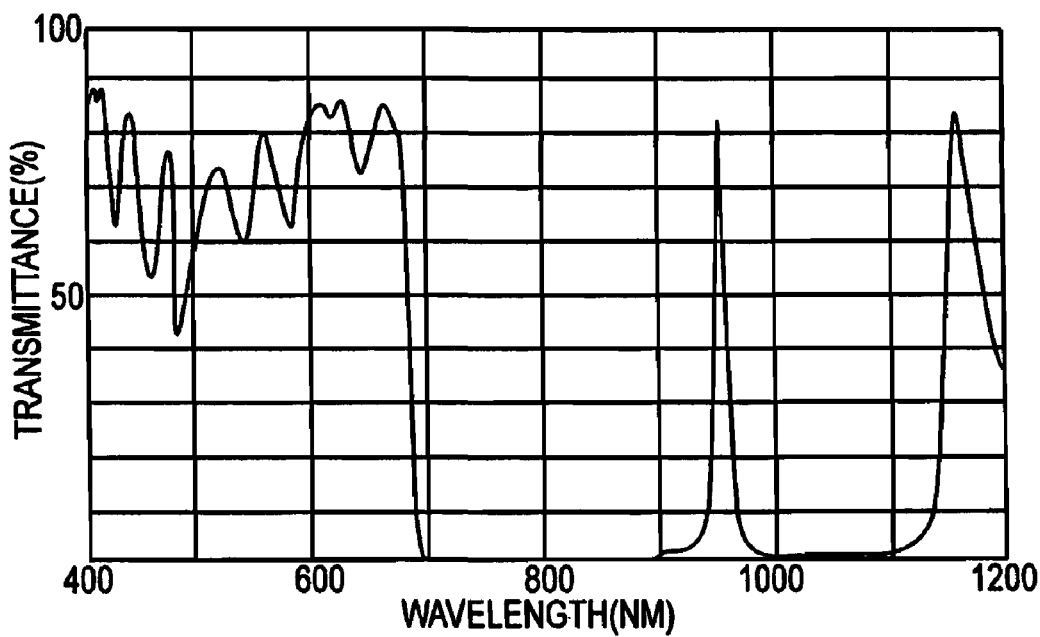
FIGS. 48(b)-48(d) show the overall spectral transmittances of the same excitation light cut-off filter when combined with the tunable filters having individual spectral transmittances as shown in FIGS. 18(b)-18(d)
Figure 48C:
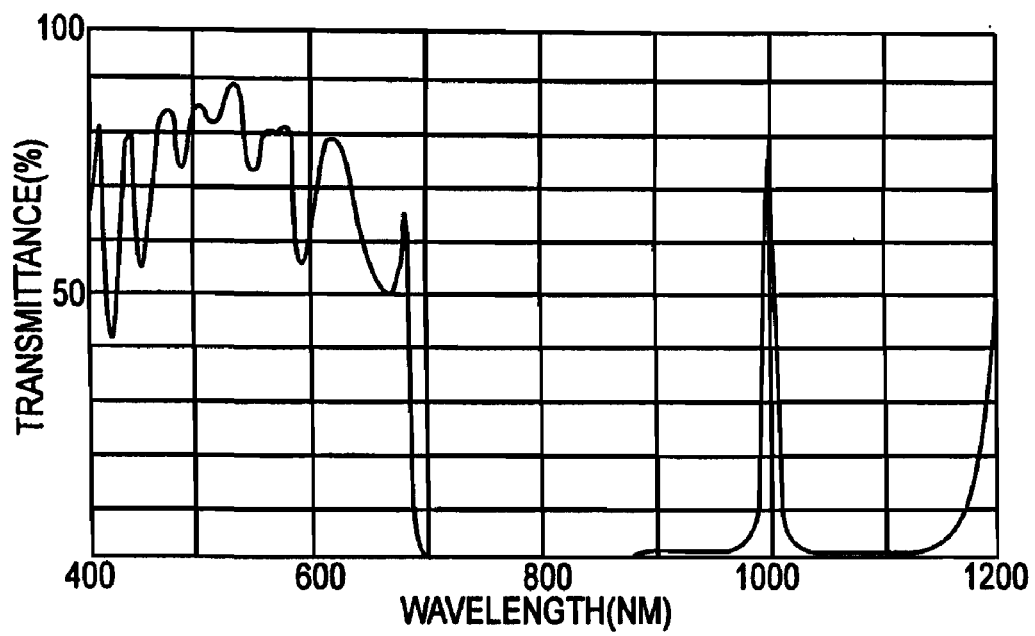
Figure 48D:
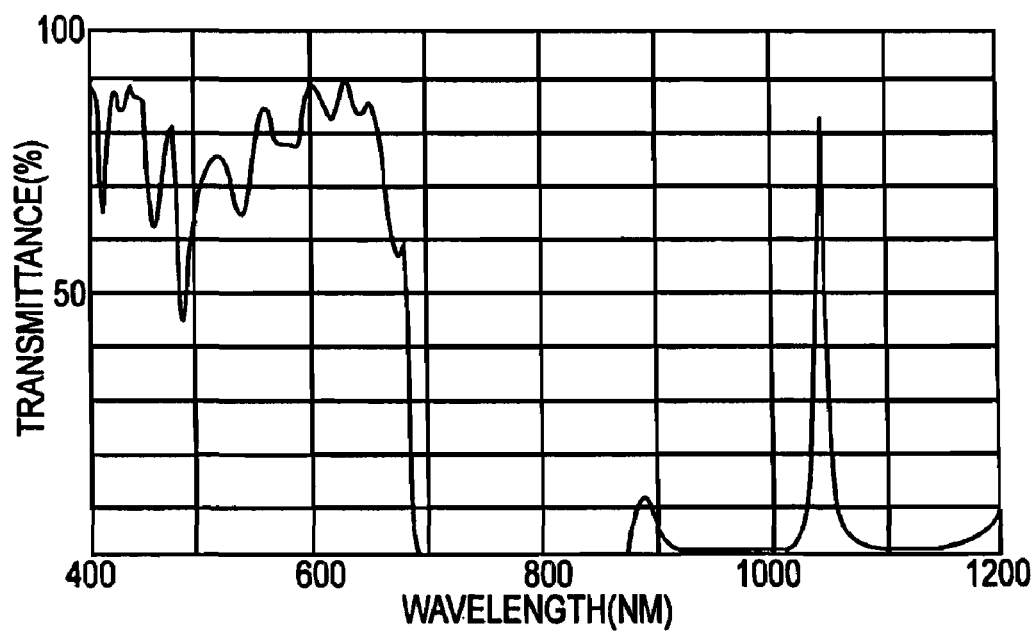

FIG. 48(a) shows the spectral transmittance properties of the excitation light cut-off filter 34. Here the excitation light has a band width ranging from 720 nm to 850 nm which is determined by the half band width of the excitation light used in the light source system. FIG. 48(a) shows the spectral transmittance properties of the excitation light cut-off filter 34. FIGS. 48(b)-48(d) show the total spectral transmittance properties of the excitation light cut-off filter 34 when combined with the tunable filters having individual spectral transmittances as shown in FIGS. 18(b)-18(d).

The excitation light cut-off filter 34 of this embodiment satisfies the following Conditions (3)-(5):

$$T_{Ex1} \geq 90\% \qquad \text{Condition (3)}$$

$$T_{Ex2} < 0.01\% \qquad \text{Condition (4)}$$

$$T_{Ex3} \geq 90\% \qquad \text{Condition (5)}$$

where $T_{Ex1}$ is the average transmittance for 400 nm$\leq \lambda \leq$650 nm, $T_{Ex2}$ is the average transmittance for 700 nm$\leq \lambda \leq$870 nm, $T_{Ex3}$ is the average transmittance for 900 nm$\leq \lambda \leq$1100 nm, and λ, is the wavelength of light incident onto the filter.

The excitation light cut-off filter 34 passes the wavelength band of 400 nm-650 nm (in which the transmittance is $T_{EX1}$) that is used for observing a visible color image composed of R, G and B color components among the light reflected by the living tissue, and cuts off the wavelength band of 700 nm-870 nm (in which the transmittance is $T_{EX2}$) that includes the excitation light of the fluorescent label materials. The wavelength band width for $T_{EX2}$ (700 nm-870 nm) is set to cover the extended wavelength range whose upper limit is 20 nm longer, and whose lower limit is 20 nm shorter, than the wavelength range determined by the filter placed in the light source system. This ensures the blocking of the excitation light that causes noise when detecting the fluorescent light. The excitation light cut-off filter 34 has a transmittance $T_{EX3}$ in the wavelength range that includes the fluorescent lights emitted from the fluorescent label materials.

The excitation light cut-off filter 34 when combined with each of the tunable filters having individual spectral transmittances as shown in FIGS. 18(b)-18(d) satisfy the following Conditions (6)-(9):

$$T3 \geq 60\% \qquad \text{Condition (6)}$$

$$T4 \leq 0.01\% \qquad \text{Condition (7)}$$

$$T5 \geq 65\% \qquad \text{Condition (8) and}$$

$$5 \text{ nm} \leq d5 \leq 35 \text{ nm} \qquad \text{Condition (9)}$$

where

T3 is the average transmittance within the visible wavelength range of 400 nm$\leq \lambda \leq$650 nm of the illumination light, T4 is the transmittance for the wavelengths within a range 20 nm above and 20 nm below the wavelength range of the excitation light generated by the illumination unit, T5 is the transmittance at the peak transmittance wavelength for an infrared passband in the wavelength range of 950 nm$\leq \lambda \leq$1050 nm, d5 is the infrared passband's full width as measured at 50% of the peak transmittance, and λ is the wavelength of light incident onto the filter.

Condition (6) ensures that there is sufficient transmittance of the filter(s) used to observe the sample in the visible region. Condition (7) ensures that the excitation light is not detected as noise during the detection of fluorescence emitted from the fluorescent labels by blocking wavelengths within a range 20 nm above and below the wavelength range of the excitation light. Conditions (8) and (9) ensure that the fluorescence wavelengths will be sufficiently transmitted by the filter(s) used to detect the fluorescence. Thus, Conditions (6)-(9) ensure that a sufficient brightness of observation light within the visible region is obtained while at the same time ensuring that the detected fluorescent light from the fluorescent labels can be separated and detected when the fluorescent labels emit fluorescence in the wavelength range 950 nm$\leq \lambda \leq$1050 nm.

FIGS. 19(a)-19(d) show spectral transmittances that relate to an exemplary design of a three-layer, tunable Fabry-Perot etalon filter when the fluorescent wavelengths of the fluorescent labels lie approximately in the range 950-1050 nm. This exemplary design is intended to improve the resolution obtainable in the infrared region as compared with the spectral transmittances (shown in FIGS. 18(b)-18(d)) exhibited by the two-layer, tunable Fabry-Perot etalon filter discussed above. The semi-transmitting coatings deposited on the substrates forming the air gaps of the three-layer, tunable filter have the same spectral transmittance as shown in FIG. 18(a) for the two-layer, tunable filter.

The air gap distances can be controlled in various ways. One way is to maintain the relationship that $d_1$ is equal to $d_2$, the other way is to maintain the relationship that $d_1$ is not equal to $d_2$.

Figure 19A:
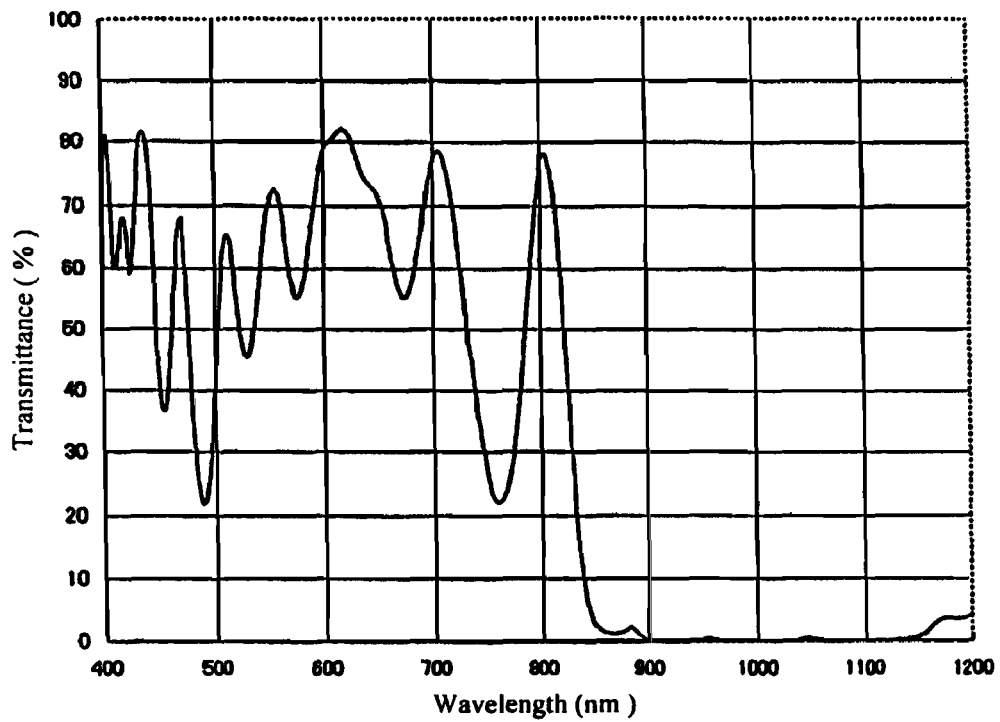
FIGS. 19(a)-19(d) relate to an exemplary design of the three-layer, tunable Fabry-Perot etalon filter wherein the wavelength $\lambda$ of fluorescent light emitted by the fluorescent labels is in the range $950 \leq \lambda \leq 1050$ nm.

FIG. 19(a) shows the spectral transmittance when $d_1$ equals 375 nm and $d_2$ equals 625 nm, which is an example that the air gap distances are controlled by the relation that $d_1$ not be equal to $d_2$. As can be seen in the figure, there is a transmission peak centered at 800 nm, and the transmittance in the wavelength range 900-1100 nm is 0.3% or less. As one would expect, the transmittance shown for any given wavelength in FIG. 19(a) is equal to the product of the transmittances shown in FIGS. 18(b) and 18(d) for that same wavelength.

Figure 19B:
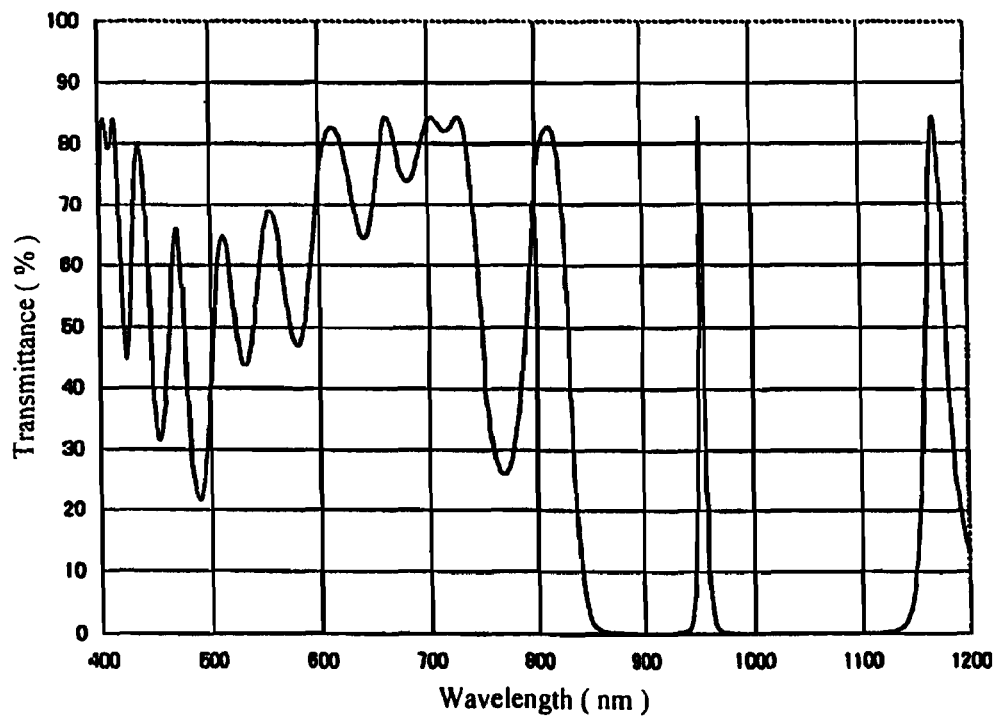

FIG. 19(b) shows the spectral transmittance when both $d_1$ and $d_2$ equal 375 nm. As one would expect in this case, the spectral transmittance at any given wavelength is the square of the transmittance at the same wavelength for the spectral transmittance curve shown in FIG. 18(b). In this situation, there is a transmission peak having roughly the same maximum transmission as in FIG. 19(a), but the peak is now centered at 950 nm in the wavelength range 900-1100 nm, and the half band width is reduced to about 7.5 nm. In addition, the transmittances in the ranges 900-930 nm, and 970-1100 nm are each 0.1% or less.

Figure 19C:
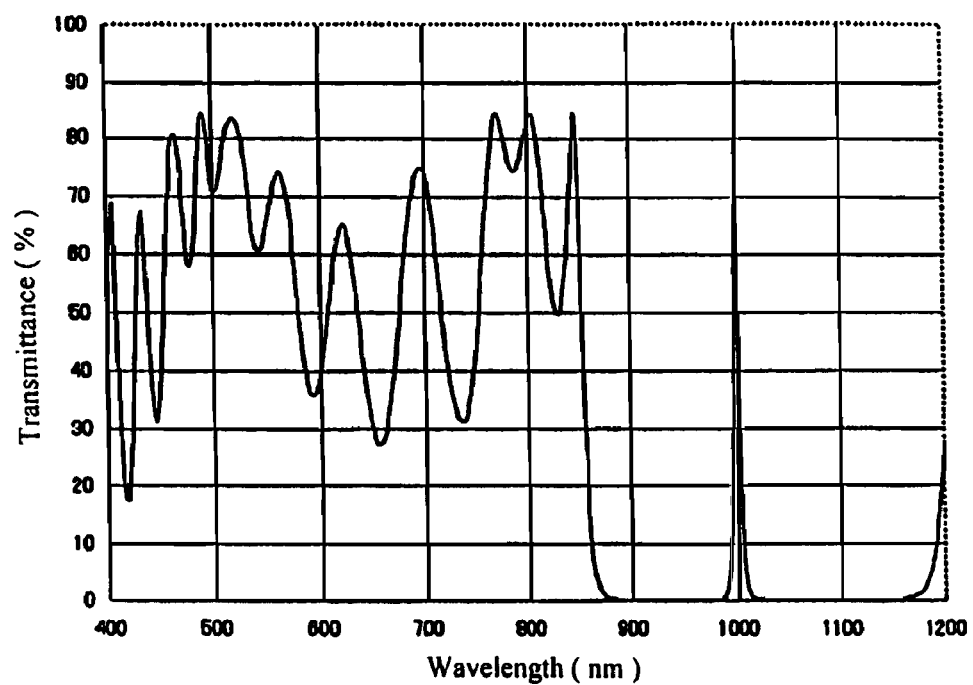
Figure 19D:
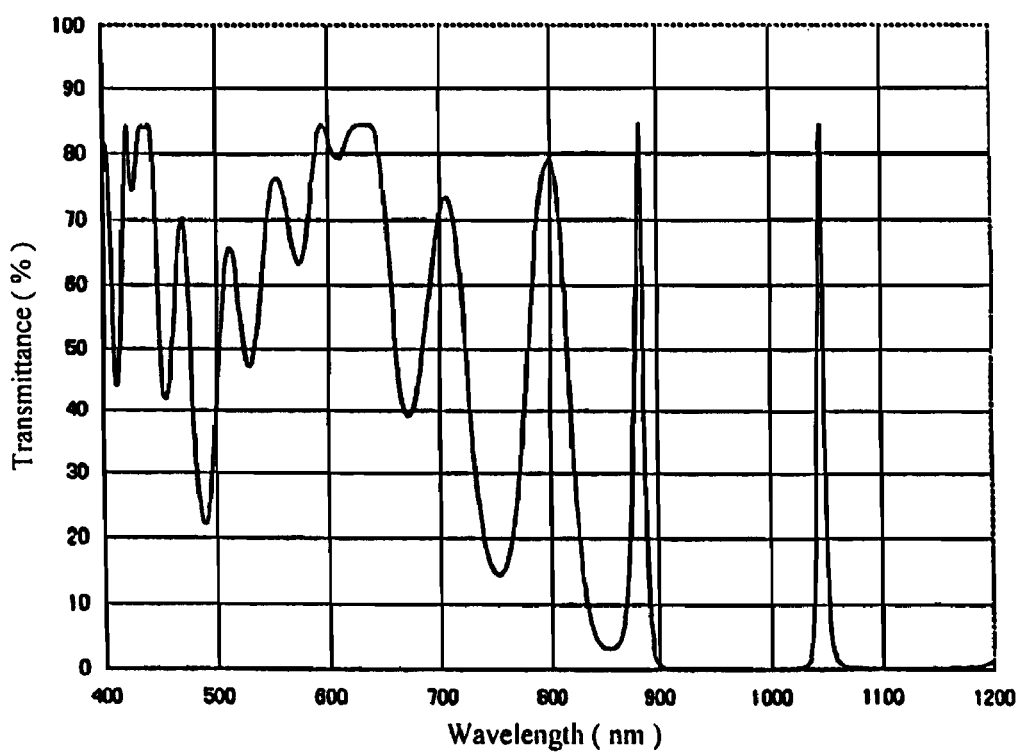

FIG. 19(c) shows the spectral transmittance when $d_1$ equals 500 nm and $d_2$ equals 500 nm. FIG. 19(d) shows the spectral transmittance when $d_1$ equals 625 nm and $d_2$ equals 625 nm. FIGS. 19(b)-19(d) are examples in which the air gap distances are controlled by the relation that $d_1$ equal $d_2$. As can be seen from comparing FIGS. 19(b)-19(d), the transmission peak in the wavelength range 900-1100 nm, is moved to longer wavelengths by changing the value of $d_1$ or $d_2$.

The two air gap distances should not be identical for good R, G, B color image observation. For example, FIG. 19(a) illustrates the spectral transmittance of the tunable filter when $d_1$=375 nm and $d_2$=625 nm.

Figure 20A:
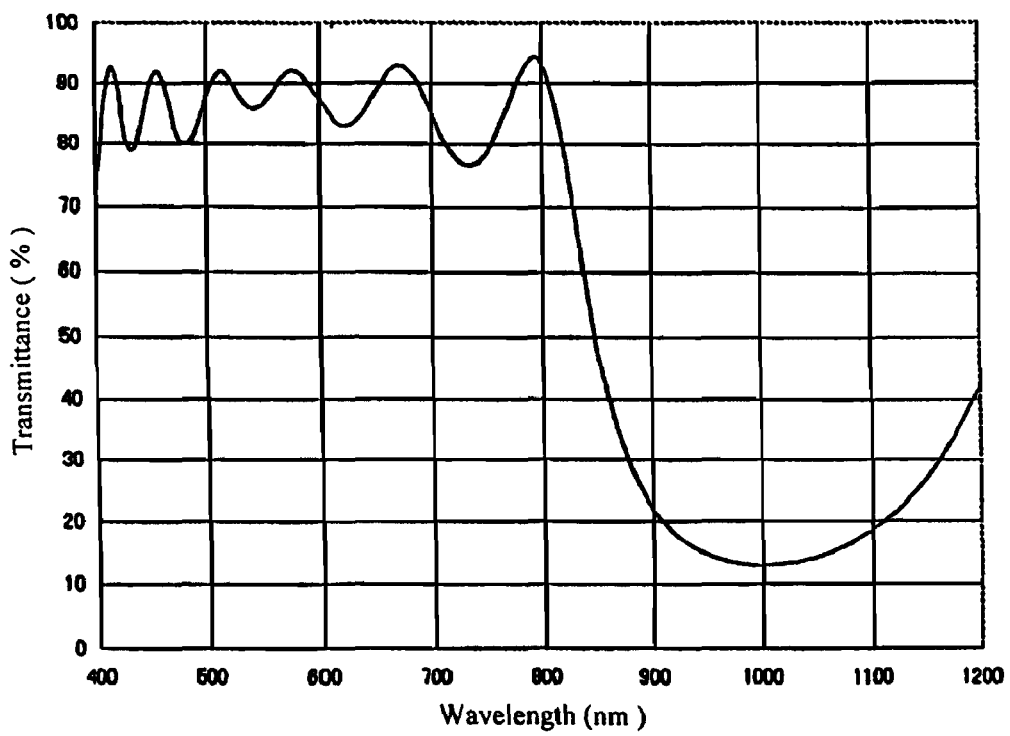
FIGS. 20(a)-20(c) show the spectral transmittances of the translucent coatings on the surfaces of the first through third substrates of an exemplary three-layer, tunable Fabry-Perot etalon filter, respectively, that face the translucent film.
Figure 20B:
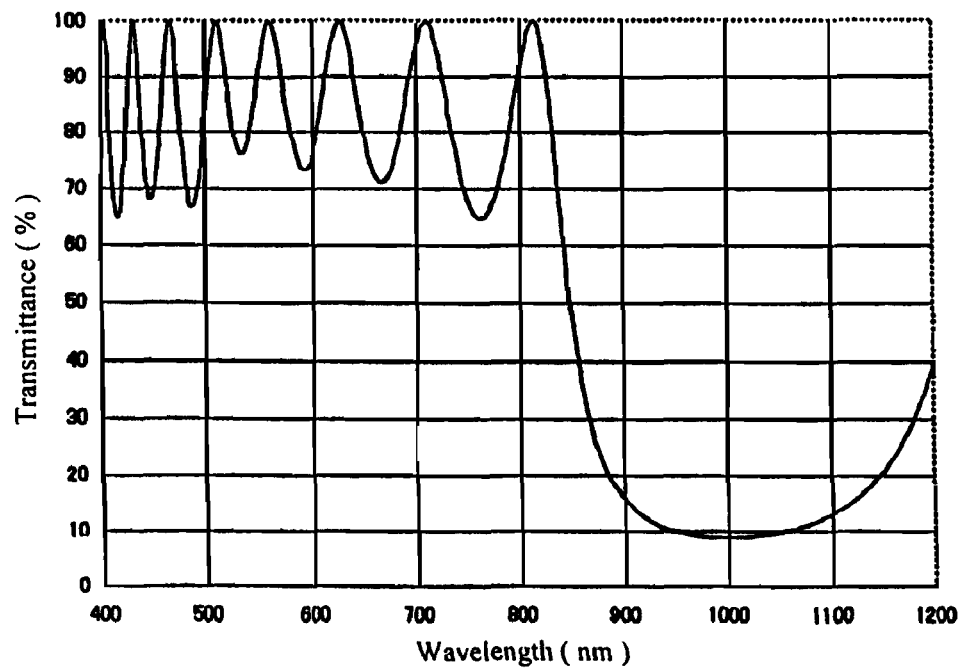
Figure 20C:
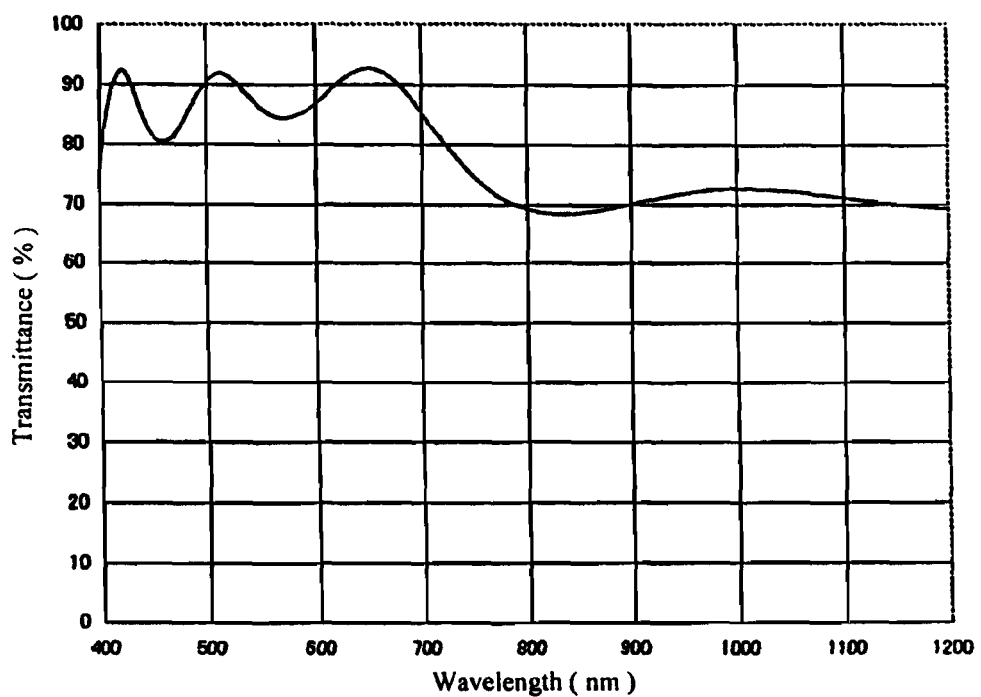

FIGS. 20(a)-20(f) show the spectral transmittances of an exemplary three-layer, tunable Fabry-Perot etalon filter when the fluorescences from the fluorescent labels lie within the approximate range of 950-1050 nm. In this exemplary design, the middle substrate among the three substrates is made of translucent film. FIG. 20(b) shows the spectral transmittance of the translucent film, and FIGS. 20(a) and 20(c) show the spectral transmittances of the translucent coatings on the surfaces of the first and third substrates, respectively, that face the translucent film.

Figure 20D:
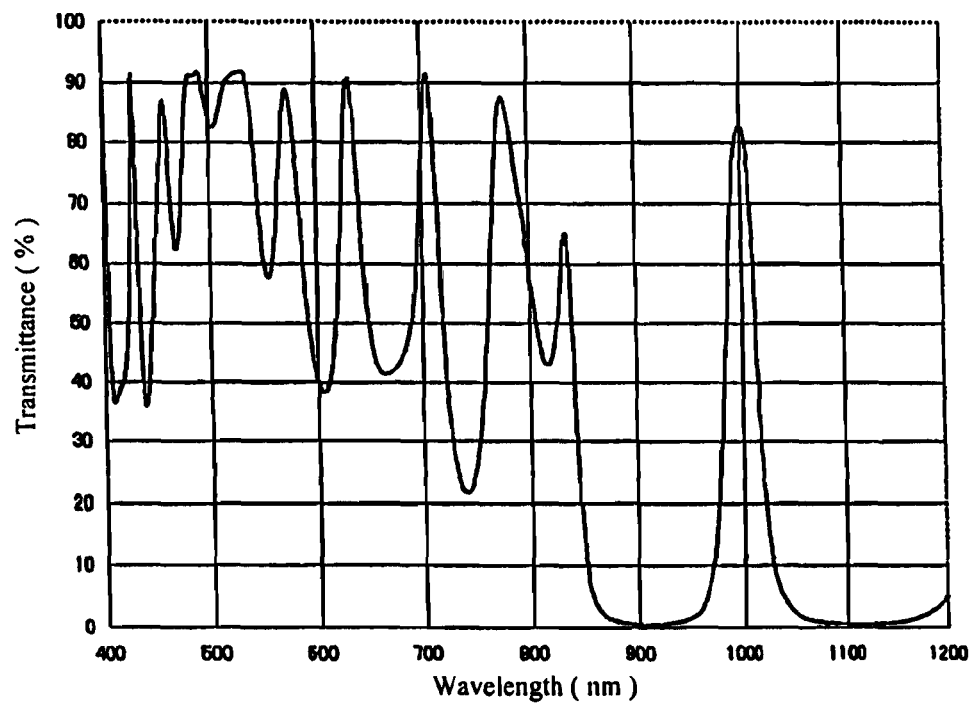
FIGS. 20(d)-20(f) show the spectral transmittances of the three-layer, tunable Fabry-Perot etalon filter when the wavelength $\lambda$ of fluorescent light emitted by the fluorescent labels is in the range $950 \leq \lambda \leq 1050$ nm.
Figure 20E:
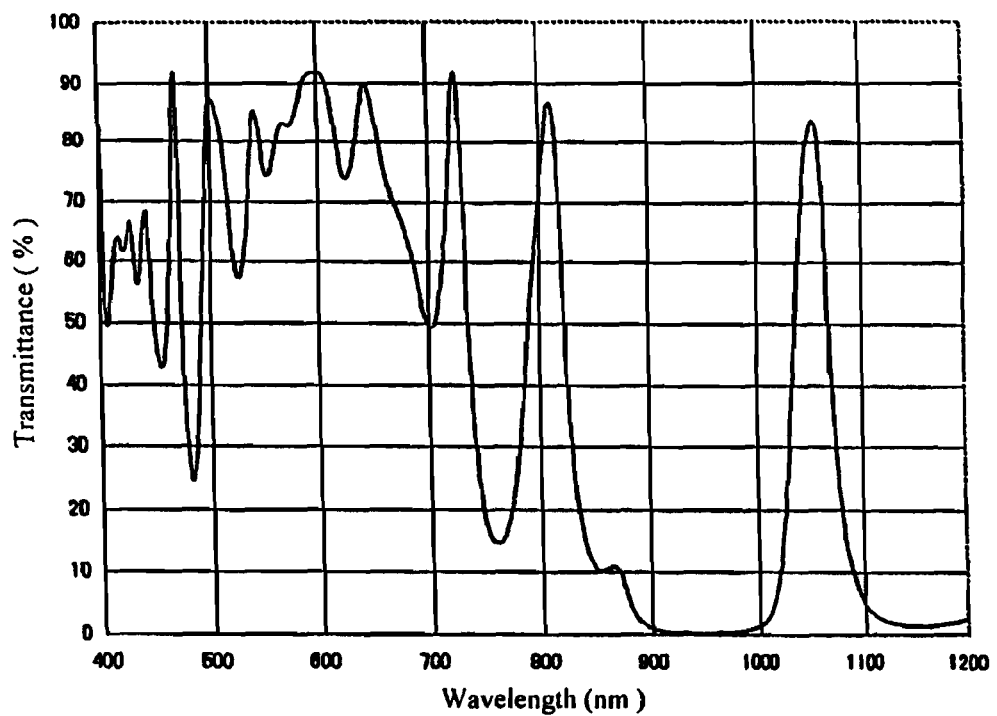
Figure 20F:
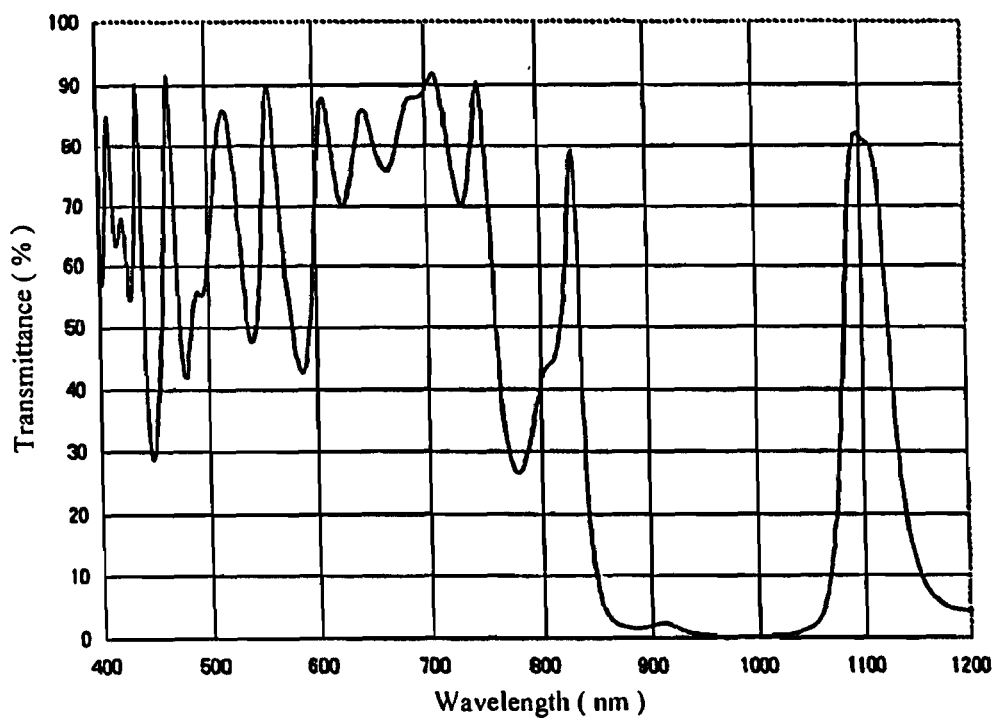

By using different spectral transmittances in the range 900-1100 nm, the resolution of the tunable filter in the near-infrared range can be appropriately defined. FIGS. 20(d)-20(f) show the spectral transmittances of the tunable filter when the two air gaps have the air gap distances $d_1$ and $d_2$ as given in Table 2 below.

TABLE 2

|  | FIG. 20(d) | FIG. 20(e) | FIG. 20(f) |
| --- | --- | --- | --- |
| $d_1$ (nm) | 500 | 562.5 | 625 |
| $d_2$ (nm) | 500 | 625 | 750 |
| peak transmission wavelength (nm) | 1000 | 1056 | 1097 |

In this exemplary design, the etalons having different transmittances are independently controlled so as to realize a low transmittance for the non-transmitting range and a larger half band width for the transmitting wavelength range within the range 900-1100 nm. This results in improving the S/N ratio when fluorescent dyes having low light emission efficiencies but larger light emission spectral width are used as fluorescent labels.

Figure 21A:
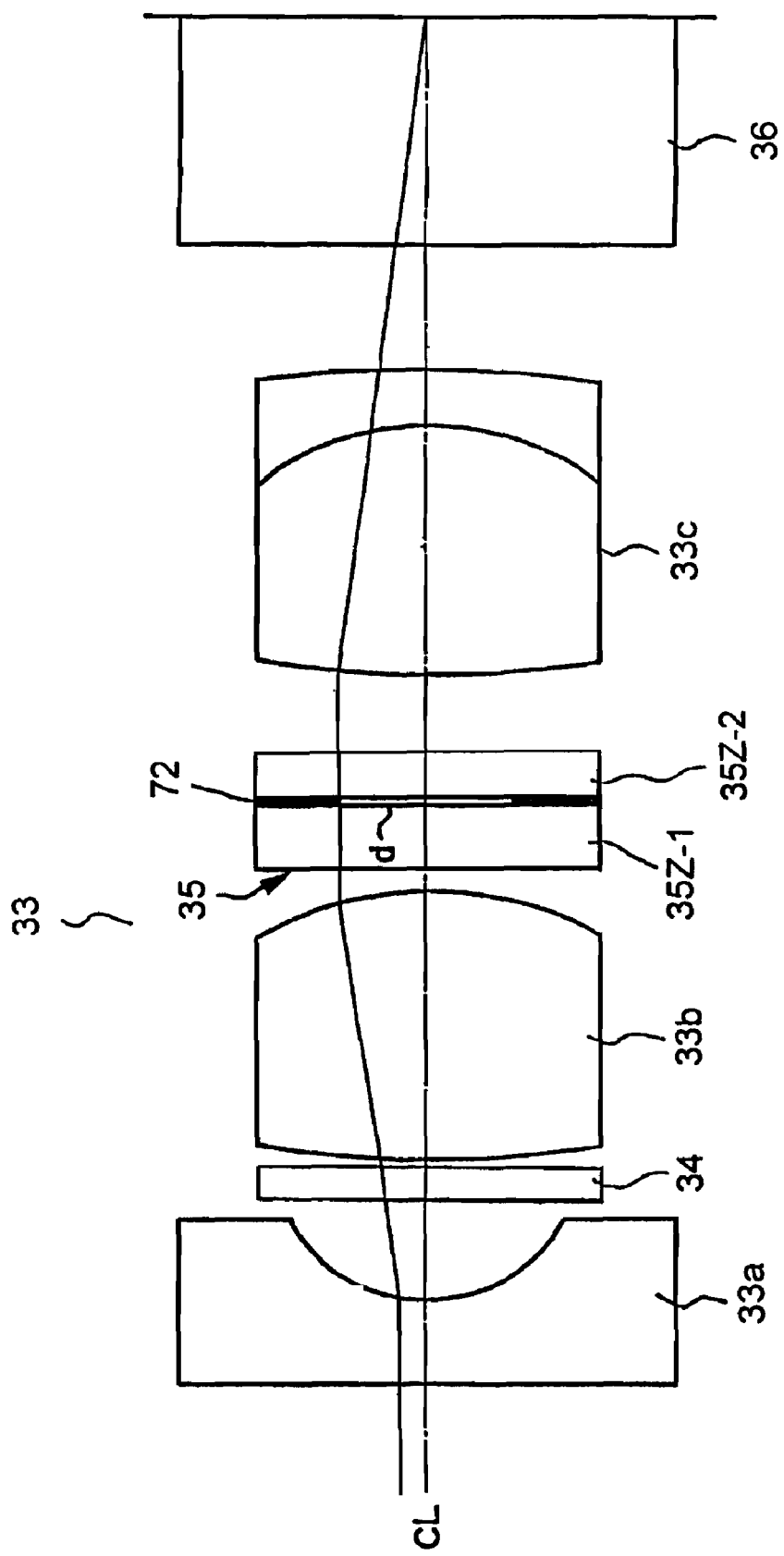
FIGS. 21(a)-21(c) show exemplary structures of tunable filters that may be provided for use with an objective lens 33, with FIG. 21(a) having a two-layer, tunable Fabry-Perot etalon filter, with FIG. 21(b) having a three-layer, tunable Fabry-Perot etalon filter, and with FIG. 21(c) having two, two-layer, tunable Fabry-Perot etalon filters.

Exemplary structures for providing the tunable filter within the endoscope optical system will now be described. FIG. 21(a) shows an exemplary structure in which a two-layer, tunable Fabry-Perot etalon filter is provided within an objective lens 33. In FIG. 21(a), the objective lens 33 is formed of, in order from the object side, a lens 33a, an excitation light cut-off filter 34, a biconvex lens 33b, a tunable filter 35, a doublet 33c, and a detector 36 having a light receiving surface.

The tunable filter 35 includes transparent substrates 35Z-1 and 35Z-2, and translucent coatings are deposited on the surfaces thereof that form an air gap d. A piezoelectric element 72 is provided between the transparent substrates 35Z-1 and 35Z-2. The piezoelectric element 72 also serves as an aperture diaphragm.

Figure 21B:
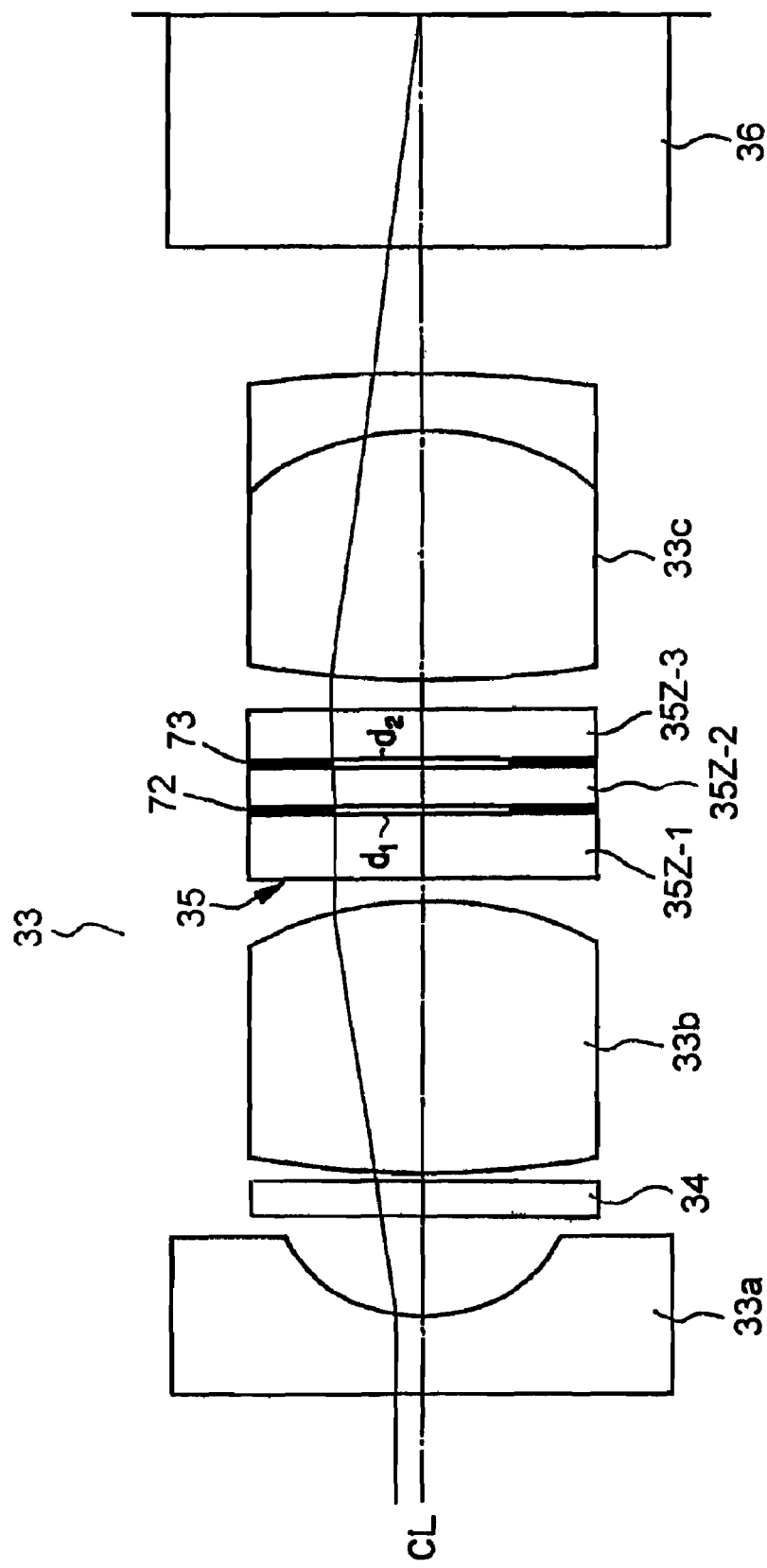

FIG. 21(b) shows an embodiment in which a three-layer, tunable Fabry-Perot etalon filter is provided in the objective lens 33 shown in FIG. 21(a). In this case, the tunable filter 35 comprises transparent substrates 35Z-1, 35Z-2, and 35Z-3, on the surfaces of which that form air gaps $d_1$ and $d_2$ translucent coatings are deposited. Piezoelectric elements 72 and 73 are provided between the transparent substrates 35Z-1 and 35Z-2 and between the transparent substrates 35Z-2 and 35Z-3, respectively.

The piezoelectric elements 72 and 73 are independently controlled. The piezoelectric element 72 also serves as an aperture diaphragm. It is desirable that the angle of incidence of light to the translucent coating (as measured from the surface normal) not be large when the tunable filter is provided in the objective optical system as shown here. In the figure, the angle of incidence of the axial marginal light is less than or equal to 1°.

Figure 21C:
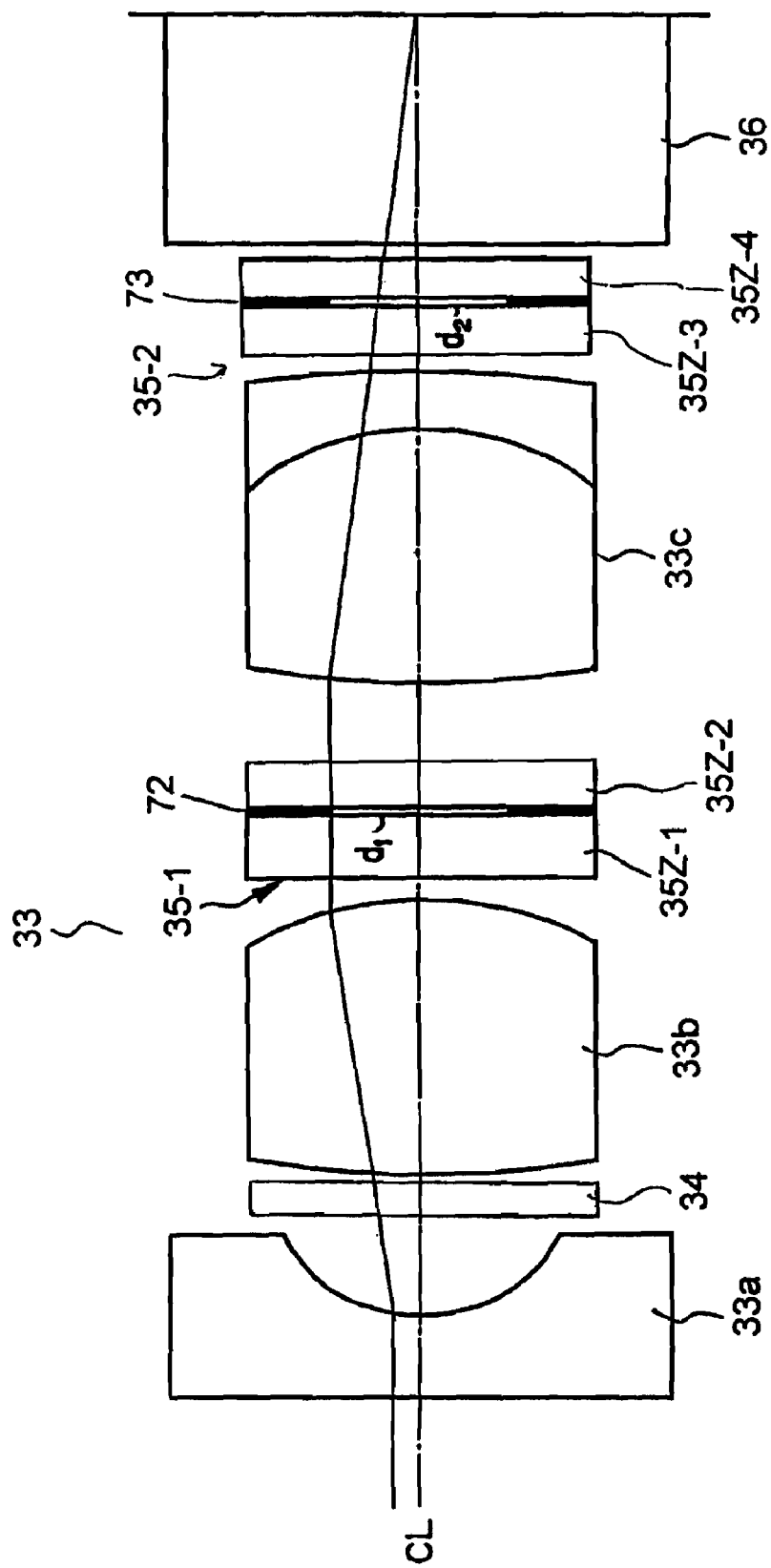

FIG. 21(c) shows an embodiment in which a pair of two-layer, tunable Fabry-Perot etalon filters are provided in the objective lens 33. In FIG. 21(c), the objective lens 33 comprises, in order from the object side, a concave lens 33a, an excitation light cut-off filter 34, a biconvex lens 33b, a tunable filter 35-1, a doublet 33c, a tunable filter 35-2, and a detector 36 with a light receiving surface. The tunable filters 35-1 and 35-2 can have either the same transmittance property or different transmittance properties.

Where there is not enough space to provide a three-layer, tunable Fabry-Perot etalon filter in the objective optical system, a combination of two-layer, tunable Fabry-Perot etalon filters can be used to obtain an equivalent transmittance property and an improved freedom of optical design, as shown in FIG. 21(c). Furthermore, it is not necessary to provide the tunable filter in the objective optical system when the endoscope is a fiberscope. For example, the tunable filter can instead be provided in the eyepiece lens or in a television camera system connected to the eyepiece lens. In addition, the excitation light cut-off filter 34 can be provided immediately before the light receiving surface of the detector 36.

Figure 22:
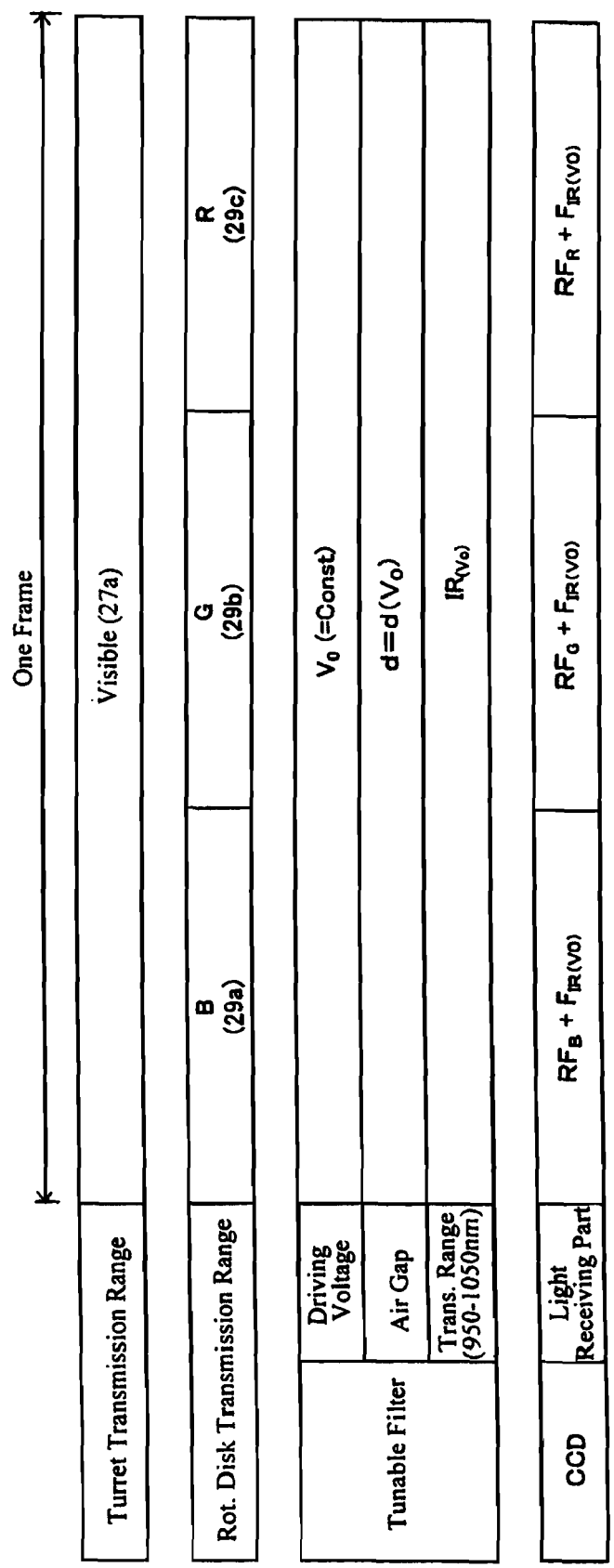
FIG. 22 is a timing chart for use in explaining the operation of the endoscope of the present invention for color image observation.
Figure 23:
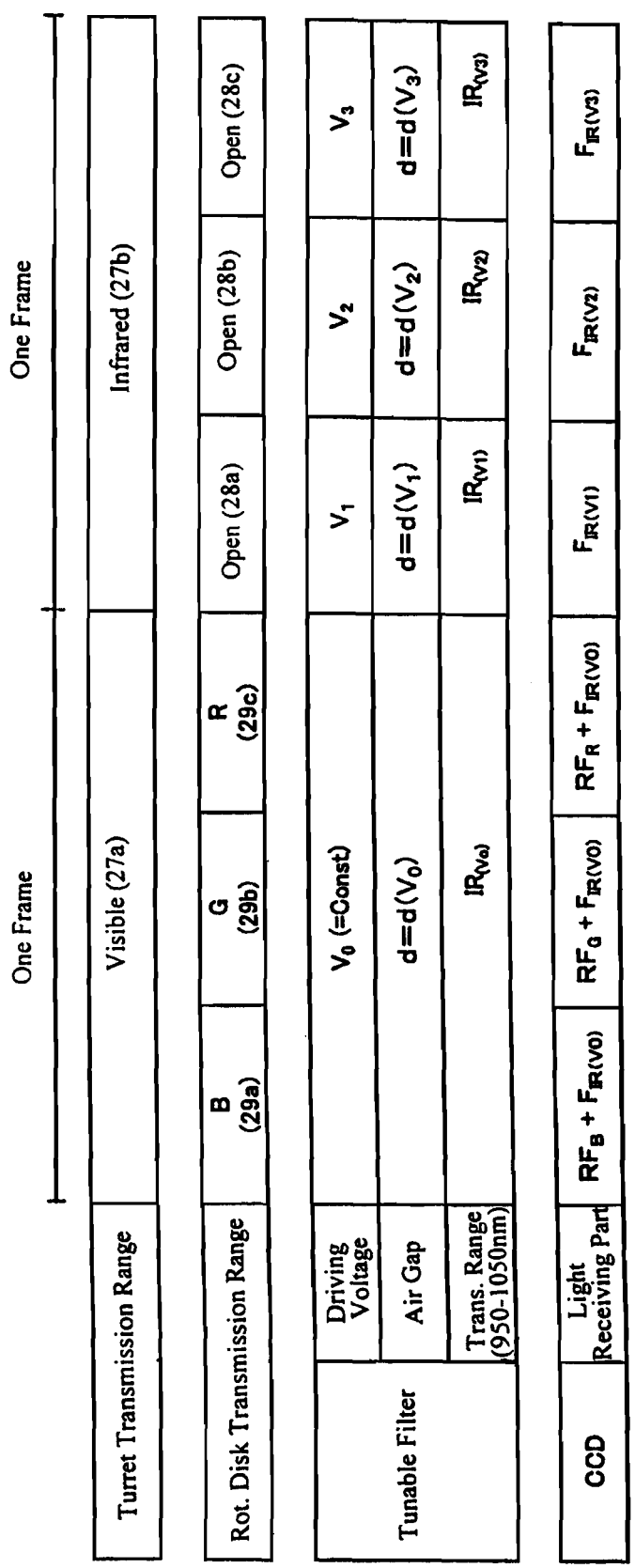
FIG. 23 is a timing chart for use in explaining the operation of the endoscope of the present invention for fluorescence detection and color image observation.

FIGS. 22 and 23 are timing charts for use in explaining the operation of the endoscope of the present invention, with FIG. 22 being the timing chart for color image observation, and FIG. 23 being the timing chart for fluorescence detection and color image observation. FIG. 25 is a timing chart for use in explaining the operation of the endoscope of the present invention for fluorescence detection and color image observation based on another operation principle.

The operation of the endoscope for color image observation shown in FIG. 22 will now be described. In the light source optical system shown in FIG. 1, the band pass filter 27a of the turret 22 (shown in FIG. 3) that primarily transmits the visible light is inserted in the optical path. In this state, the inner windows 29a, 29b, and 29c of the rotational disk 23 shown in FIG. 5 are sequentially inserted in the optical path so as to sequentially transmit B, G, or R light intermittently. Here, a period of time during which the rotational disk 23 rotates one time is termed one frame.

An explanation will now be provided wherein it is assumed that an objective lens 33 as shown in FIG. 21(a) is used as the objective optical system and that a two-layer, tunable Fabry-Perot etalon filter having the spectral transmittance as shown in FIGS. 18(b)-18(d) is provided in the insertion section of an endoscope tip used as the tunable filter 35. It is further assumed that the air gap has a distance $d=d(V_0)$ when a driving voltage $V_0$ is applied to the piezoelectric element 72 of the tunable filter 35, and that the transmission wavelength range of the tunable filter 35 $IR_{(V0)}$ varies in the range 950-1050 nm, depending on the air gap distance $d(V_0)$.

It is unnecessary to scan the tunable filter 35 during color image observation. The driving voltage applied to the piezoelectric element 72 per frame is maintained at $V_0$ and the air gap distance is maintained at $d=d(V_0)$. Thus, the B, G, R light reflected by the living tissue and the fluorescence produced by the fluorescent labels reach the light receiving surface of the detector 36. In the timing chart, the B, G, R light reflected by the living tissue are indicated by $RF_B$, $RF_G$, and $RF_R$ and the fluorescence produced by the fluorescent labels is indicated by $F_{IR(V0)}$.

The control of the endoscope system is simplified for color image observation. $V_0$ can be changed to scan the wavelengths in accordance with the wavelengths of the illumination light B, G, or R and the transmittance of the tunable filter.

Light received by the detector 36 (the image pickup element) is subject to photo-electric conversion to produce image signals for R, G, and B color components, which are then supplied to a processor 5. The processor 5 processes signals and displays color images of the living tissue on a monitor 6. During the operation for color image observation shown in FIG. 22, the detector 36 receives the fluorescence along with the reflected light. However, the intensity of the fluorescence $F_{IR(V0)}$ is significantly low and therefore the influence of the fluorescence on the production of color images can be neglected.

The operation of the endoscope shown in FIG. 23 is described hereafter. The endoscope used has the same structure as the one in FIG. 22. The timing chart in FIG. 23 shows the alternate operation of the fluorescence detection and the color image observation. In this case, the band pass filter 27a of the turret 22 is inserted in the optical path during the first frame and the band pass filter 27b is inserted in the optical path during the following frame.

During the first frame, the rotational disk and tunable filter operate as described with reference to FIG. 22 and the detector 36 sequentially receives $RF_B+F_{IR(V0)}$, $RF_G+F_{IR(V0)}$, $RF_R+F_{IR(V0)}$. On the other hand, during the following frame, the outer windows 28a, 28b, and 28c of the rotational disk 23 are sequentially inserted in the optical path and, thus, the excitation light in the near-infrared range illuminates the living tissue intermittently. A driving voltage $V_1$ is applied to the piezoelectric element 72 and the air gap has a distance $d=d(V_1)$ while the window 28a is inserted in the optical path. Consequently, the detector 36 receives $F_{IR(V1)}$.

A driving voltage $V_2$ is then applied to the piezoelectric element 72 so that the air gap has a distance $d=d(V_2)$ while the window 28b is inserted in the optical path. Consequently, the detector 36 receives $F_{IR(V2)}$. A driving voltage $V_3$ is then applied to the piezoelectric element 72 so that the air gap has a distance $d=d(V_3)$ while the window 28c is inserted in the optical path. Consequently, the detector 36 receives $F_{IR(V3)}$.

In this way, three different fluorescent wavelengths can be detected in a frame. When more than three different fluorescent wavelengths should be detected, the driving voltages applied to the piezoelectric element 72 can be further altered in another frame. FIG. 24 shows a timing chart in such a case. For example, driving voltages $V_1$-$V_3$ can be sequentially applied to the piezoelectric element 72 while the windows 28a-28c are rotated sequentially into the optical path, and driving voltages $V_4$-$V_6$ can be sequentially applied to the piezoelectric element 72 while the windows 28a-28c are next sequentially rotated into the optical path.

The rotation cycles of the turret 22 and rotational disk 23 and the driving voltage of the piezoelectric element 72 are controlled in a synchronous manner per frame. Control is executed by, for example, a filter control circuit 51 shown in FIG. 1. According to the timing chart in FIG. 23, color images and fluorescent information of the living tissue can be concurrently displayed on the monitor 6 after the processor 5 processes the images.

FIG. 25 shows a timing chart for use in explaining the operation of the endoscope when the objective lens 33 shown in FIG. 21(b) is used as the objective optical system provided in the endoscope tip. The tunable filter 35 has the transmittance properties as shown in FIGS. 19(b)-19(d). The differences from the timing chart in FIG. 23 will now be described.

Two air gaps $d_1$ and $d_2$ of the tunable filter 35 are independently controlled. During the first frame, different driving voltages are applied to the piezoelectric elements 72 and 73 so that $d_1$ does not equal $d_2$. Then, during the next frame, three different driving voltages $V_1$, $V_2$ and $V_3$ are sequentially applied to the piezoelectric elements 72 and 73 when the rotational disk has a window in the light path such that, at any instant during the following frame, the air gaps $d_1$ and $d_2$ are identical. For example, $d_1(V_1)=d_2(V_1)$ where $d_1=d_2$ so as to transmit $F_{IR(V1)}$ while the window 28a is in the optical path, and $d_1(V_2)=d_2(V_2)$ where $d_1=d_2$ so as to transmit $F_{IR(V2)}$ while the window 28b is in the optical path.

The method for creating images will now be described with reference to FIG. 1. A processor 5 includes a filter control circuit 51, a pre-processor circuit 52, an A/D converter 53, an image signal processing circuit 54, and a D/A converter 55. The filter control circuit 51 controls the turret 22 in the light source optical system 2 for positioning the band pass filters 27a and 27b in the optical path. It also controls the rotational disk 23 for positioning the outer and inner windows in the optical path.

The filter control circuit 51 further controls the voltage applied to the piezoelectric elements provided in the tunable filter 35 so as to control the air gap d of the tunable filter 35 and thus, shifts the transmission wavelength range as described with reference to FIG. 13. The filter control circuit supplies the pre-processor circuit 52 with control signals. The pre-processor circuit 52 adjusts the image signals supplied from the detector 36 by adjusting the gain of an amplifier that receives the detected image signals and by adjusting the white balance of color images using a white balance correction circuit.

Image signals from the pre-processor circuit 52 are supplied to the A/D converter 53 where analog signals are converted to digital signals. The digital signals converted by the A/D converter 53 are supplied to the image signal processor circuit 54 and stored in an image memory.

Subsequently, they are subject to image processing, such as image enhancing and noise elimination, and display controls for concurrent display of a fluorescent image, a color image, and a character image. The image signal processing circuit 54 further executes the process for displaying a fluorescent image overlapped with a color light image or for normalizing the fluorescent intensity by calculation between color and fluorescent images. This provides a fluorescent image that is easy to identify along with a color image. The digital signals from the image signal processing circuit 54 are supplied to the D/A converter 55 where they are converted to analog signals. The analog signals are supplied to the monitor 6 which displays individual images.

The filter control circuit 51 controls the transmission wavelength range of fluorescence so that the fluorescent peak wavelengths are calculated or counted and the displayed image (monitor 6) is provided in pseudo-colors according to the count or counted fluorescence and the associated fluorescent labels.

Table 3 below lists an example of the display of five different fluorescent labels detected at a point Pi (Xi, Yi) in a lesion.

TABLE 3

| Fluorescent Label No: | 1 | 2 | 3 | 4 | 5 |
|---|---|---|---|---|---|
| $P_1 (X_1, Y_1)$: | | ○ | ○ | ○ | ○ |
| $P_2 (X_2, Y_2)$: | | ○ | ○ | | |
| $P_3 (X_3, Y_3)$: | ○ | | | | |

Figure 26:
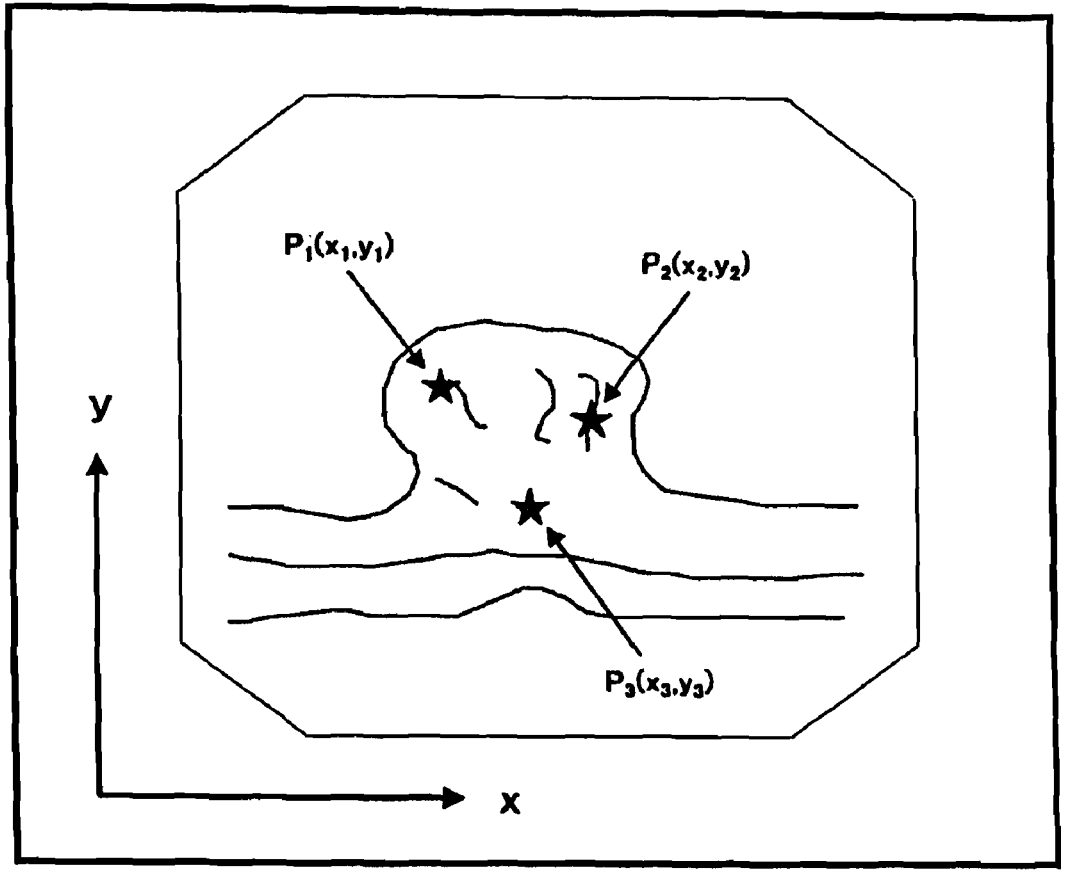
FIG. 26 shows a display image on a monitor.

The coordinate $X_1$, $Y_1$, for example, is a point on the monitor shown in FIG. 26. The fluorescent labels $P_1(X_1, Y_1)$, $P_2(X_2, Y_2)$, and $P_3(X_3, Y_3)$ can be displayed in different colors. For example, $P_1$ can be displayed in yellow, $P_2$ can be displayed in red, and $P_3$ can be displayed in green, depending on the number and type of fluorescent labels obtained, or their combination. These can represent the degree of malignancy of the lesion by color, allowing a highly advanced diagnosis.

FIG. 26 shows concurrent display of a color image overlapped with a fluorescent image on the monitor 6. The color image presents the morphology of the lesion and the fluorescent image presents the functional information (information on the degree of malignancy) of the lesion. As shown in FIG. 26, concurrent display allows for the diagnosis of the location and the malignancy of the lesions.

The image processing described above ensures the observation of a current condition, such as a cancer of a lesion, without error. The processor 5 calculates or counts the fluorescent peak wavelength signals and refers to a table of corresponding proteins to the fluorescent peak wavelengths in a memory of the processor 5 to identify the protein present in the living body and stores the identified protein in the memory as data. Thus, individual in vivo protein data can be read from the memory and compared with the data in the table of corresponding proteins to reference fluorescent peak wavelengths.

Figure 27:
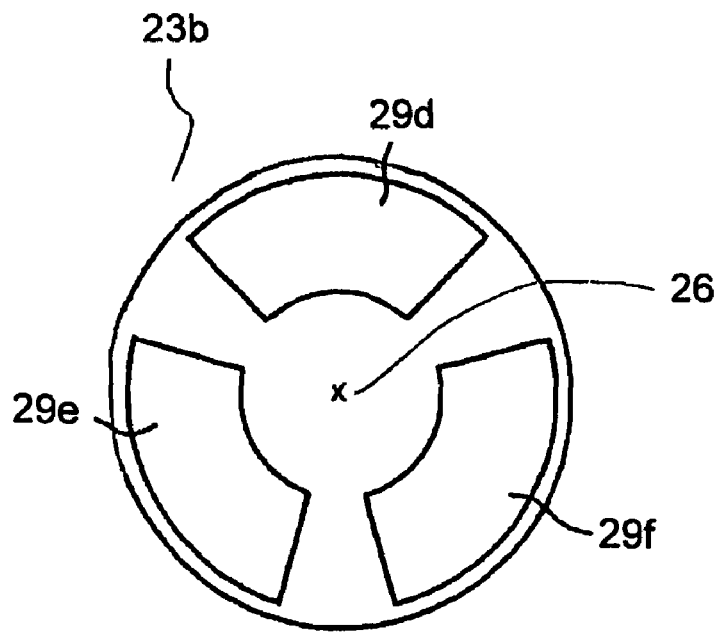
FIGS. 27 and 28 show another embodiment of the rotational disk of the light source optical system and with three different band pass filters attached to the windows 29d, 29e, and 29f, respectively, of the rotational disk, with FIG. 27 showing the structure of a rotational disk 23b and FIG. 28 showing the spectral transmittances of the three different band pass filters B, G, R.
Figure 28:
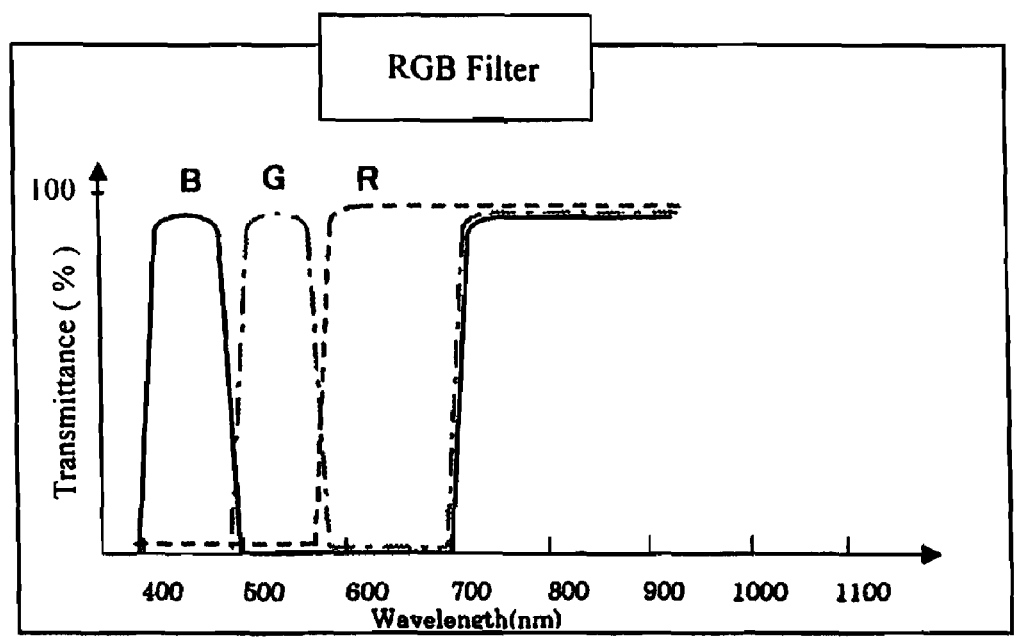

FIGS. 27 and 28 show another embodiment of the rotational disk of the light source optical system and of the band pass filter attached to the windows 29d, 29e, and 29f of the rotational disk. Only the differences from the rotational disk and band pass filter shown in FIGS. 5 and 6 will now be described.

FIG. 27 shows the structure of a rotational disk 23b and FIG. 28 shows the spectral transmittance of the band pass filter. As shown in FIG. 27, the rotational disk 23b has three windows 29d, 29e, and 29f, in which are mounted a blue (B) filter (not shown), a green (G) filter (not shown), and a red (R) filter (not shown), respectively. As shown in FIG. 28, the B, G, and R filters transmit light in the near-infrared range in addition to transmitting light in the blue, green, and red wavelengths, respectively.

Table 4 below lists the possible combinations of the band pass filter provided on the turret 22 and the windows provided in the rotational disk 23b.

TABLE 4

| | Turret 22 | Rotational Disk 23b | Illumination Light |
|---|---|---|---|
| visible light mode: | 27a | 29d, 29e, 29f | visible light (B, G, R) |
| infrared mode: | 27b | 29d, 29e, 29f | infrared (excitation light) |

Only the B, G, or R light is transmitted and irradiated onto the living tissue while the band pass filter 27a that is provided on the turret 22 is inserted in the optical path. The excitation light in the near-infrared range is irradiated onto the living tissue while the band pass filter 27b is inserted in the optical path. In this way, the rotational filter can be down-sized, thereby enabling the entire light source device to be made smaller. Furthermore, with the filter control mechanism being simplified, the production cost of the light source device can be reduced.

Figure 29A:
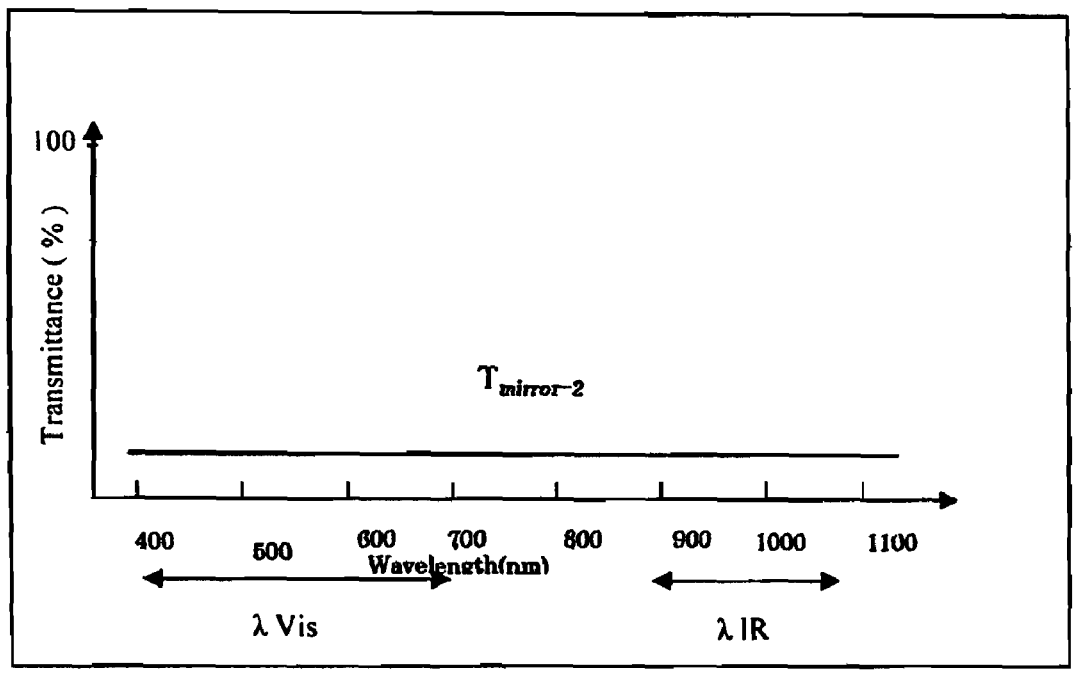
FIGS. 29(a)-29(c) show the spectral transmittances of another embodiment of a tunable filter, with FIG. 29(a) being the spectral transmittance of a semi-transmitting coating that is deposited on the substrates that form an air gap, with FIG. 29(b) being the spectral transmittance of the tunable filter having an air gap, and with FIG. 29(c) being the spectral transmittance of the tunable filter when the air gap distance is changed to a different distance.
Figure 29B:
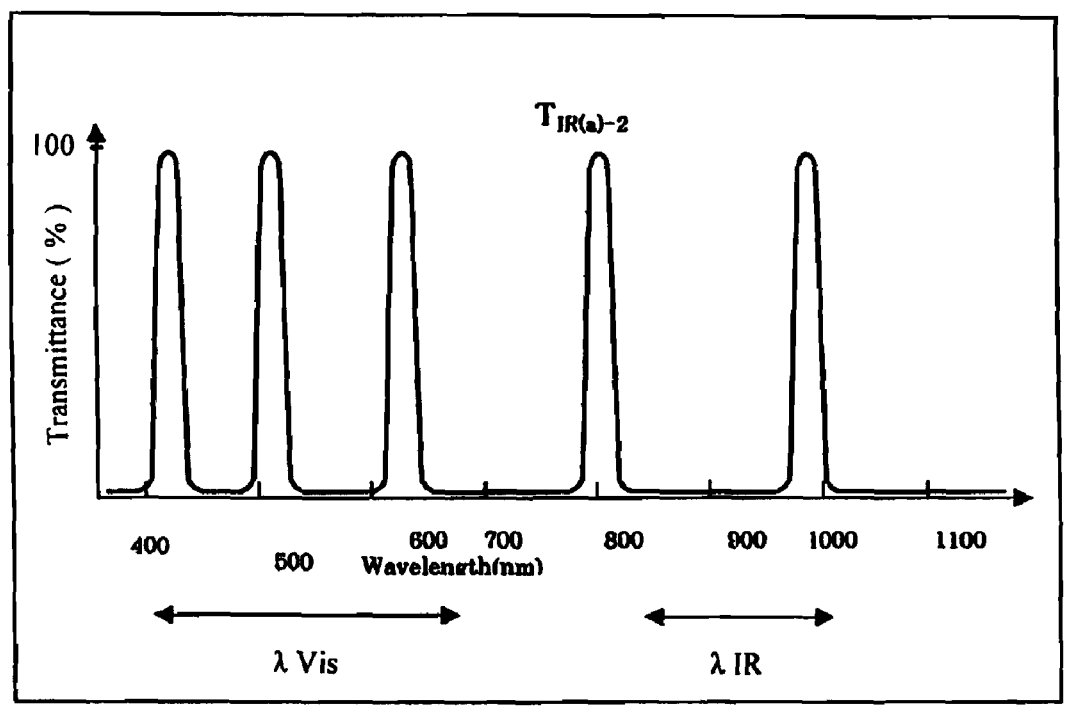
Figure 29C:
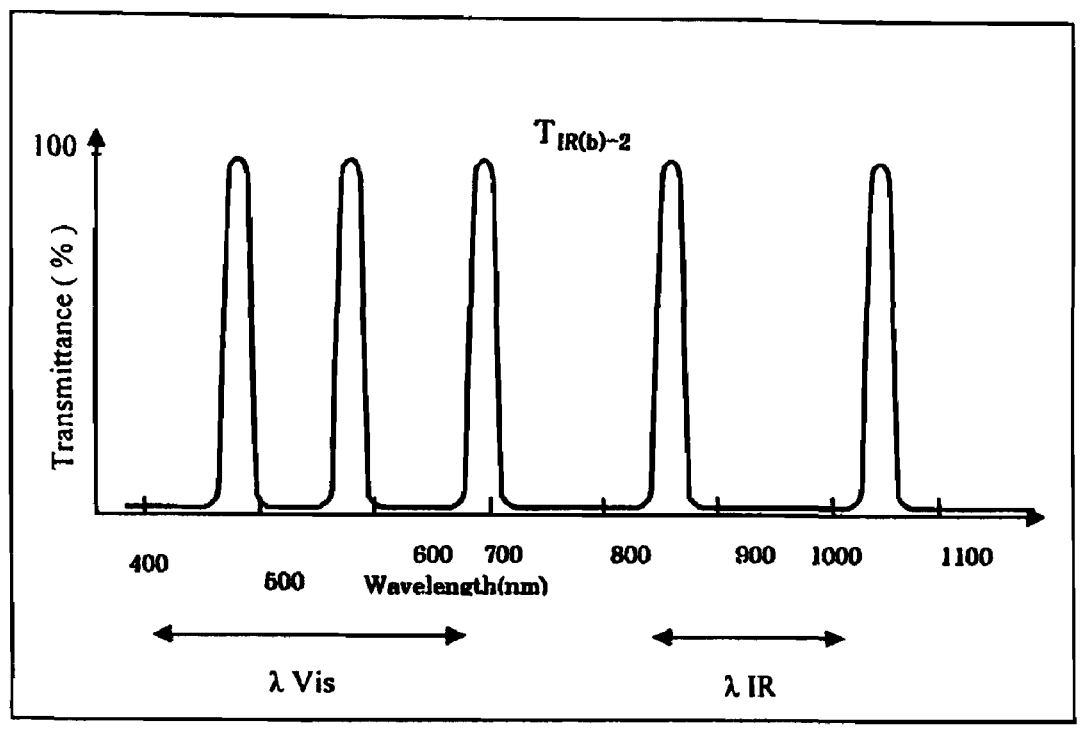
Figure 30A:
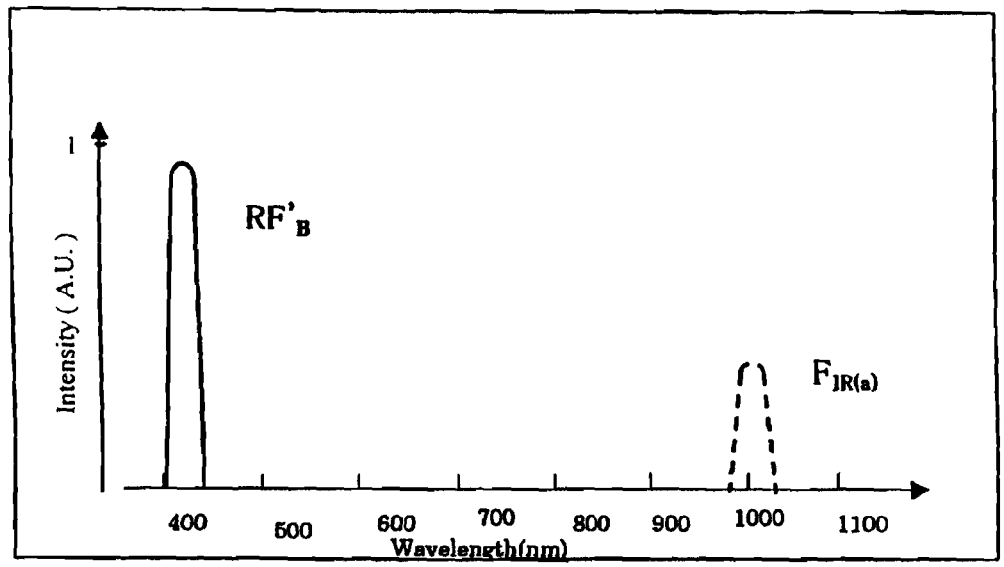
FIGS. 30(a)-30(d) show the spectral intensity of light that is transmitted through the tunable filter 35 and reaches the light receiving surface of the detector 36.
Figure 30B:
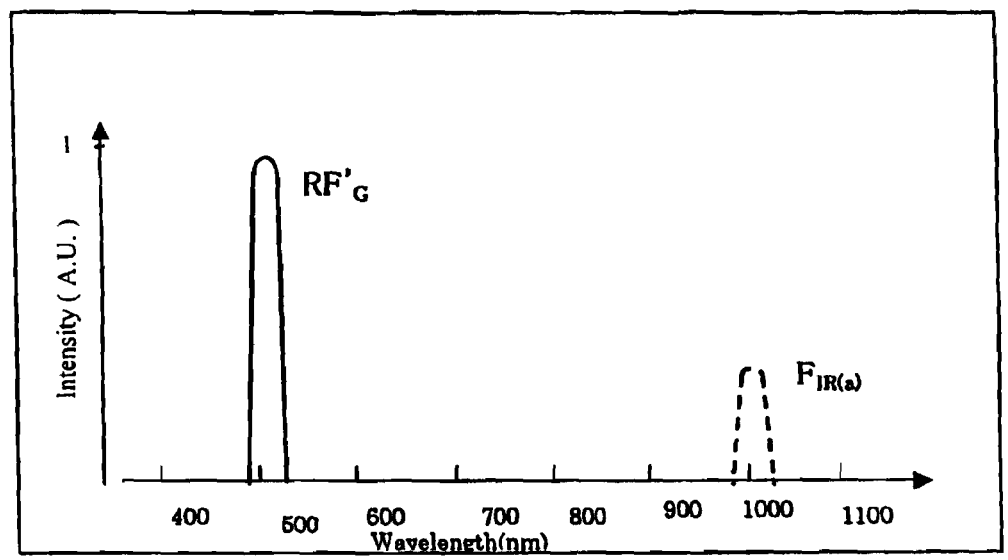
Figure 30C:
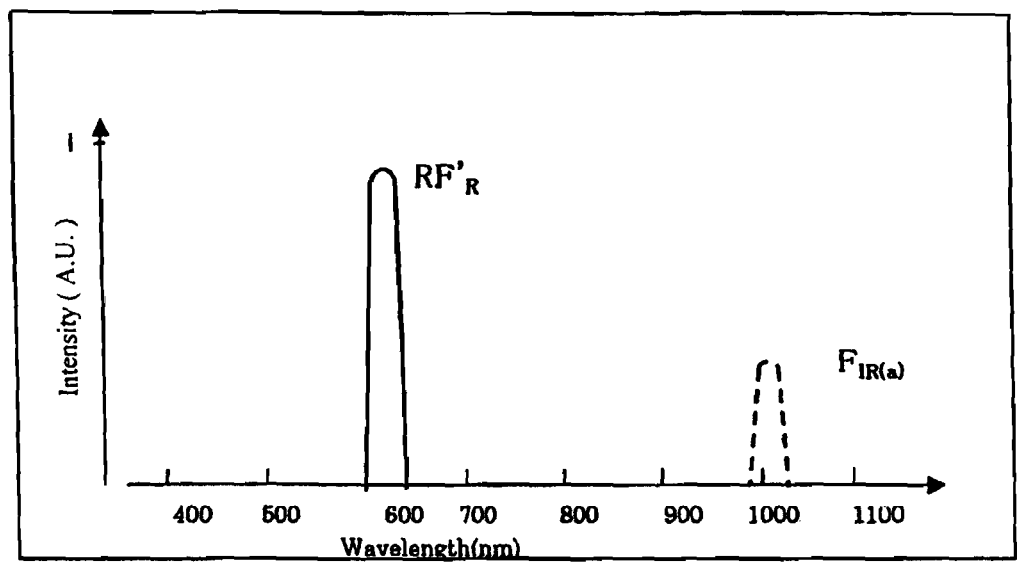
Figure 30D:
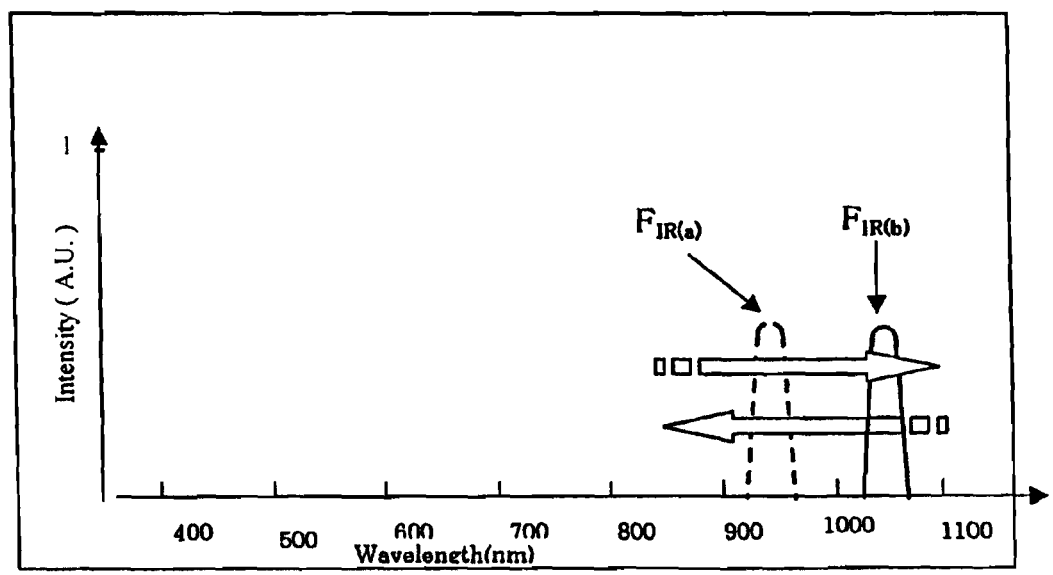

Another embodiment of the structure of the tunable filter is described with reference to FIGS. 29(a)-29(c). In FIGS. 29(a)-29(c), the transmittance is plotted on the ordinate and the wavelength is plotted on the abscissa. Here, it is assumed that the fluorescent wavelengths from the fluorescent labels are in the range 950-1050 nm. FIG. 29(a) shows the spectral transmittance of the semi-transmitting coating deposited on the substrates forming an air gap. In this structure, the spectral transmittance of the semi-transmitting coating is characterized by a constantly low transmittance over the entire range of wavelengths in use.

On the other hand, due to interference effects, the spectral transmittance of the tunable filter periodically has passbands as shown in FIG. 29(b), at least in the wavelength range 400-1100 nm. The transmittance peaks occur at wavelengths λ according to the following equation:

$$2 n_d d \cos \alpha = m\lambda \qquad \text{Equation (1)}$$

where
  $n_d$ is the refractive index of the air gap,
  d is the thickness of the air gap,
  α is the angle of incidence of light onto the tunable filter, as measured from the surface normal,
  m is the interference order, and
  λ is the wavelength of a passband peak transmittance.

FIG. 29(c) shows the spectral transmittance when the air gap distance is changed from a distance A to a distance B, where both the distance A and the distance B are sufficient for the light to be subject to multiple interferences. As shown in FIG. 29(c), the wavelengths of the peak transmittance are shifted, but the peak transmittance amplitudes remain substantially constant. The semi-transmitting coating having the spectral transmittance property as shown in FIG. 29(a) can be made of a metal coating formed of deposited silver and aluminum layers, or the coating can be a dielectric, multi-layered coating.

Light having the spectral intensity properties as shown in FIGS. 11(a)-11(c) enters the objective lens 33 and a portion of this light is transmitted through the tunable filter 35 and reaches the light receiving surface of the detector 36. The light that reaches the receiving surface of the detector 36 has the spectral intensity properties shown FIGS. 30(a)-30(d). In the FIGS. 30(a)-(d), the intensity is plotted in arbitrary units (A.U.) on the ordinate and the wavelength (in nm) is plotted on the abscissa.

As mentioned above, the tunable filter of this exemplary structure has a discrete property in which the transmission wavelengths in the visible range periodically have peaks. This allows partial, narrow ranges of wavelengths among the reflected light from the living tissue to transmit through the tunable filter. The transmission wavelengths of the tunable filter can be scanned so as to subdivide the light into narrow ranges of wavelengths. This allows fine analysis of data concerning the living tissue that is carried by the light that has been reflected from the living tissue. Needless to say, the tunable filter can be operated to detect plural fluorescent wavelengths in the near-infrared range.

Figure 31A:
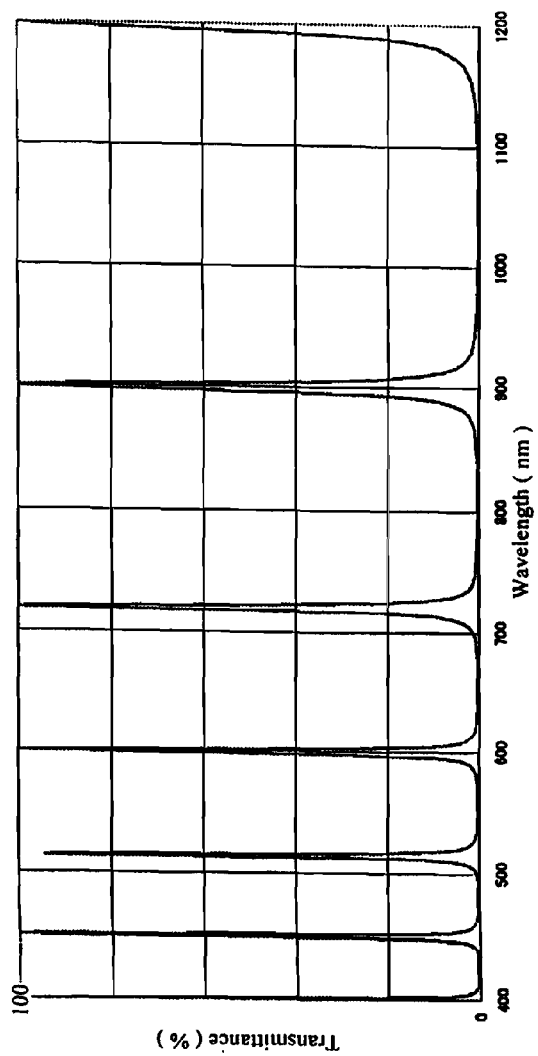
FIGS. 31(a)-31(c) show the spectral transmittances of an exemplary two-layer, tunable filter when the air gap distance d is 1800 nm, 2000 nm, and 2200 nm, respectively.
Figure 31B:
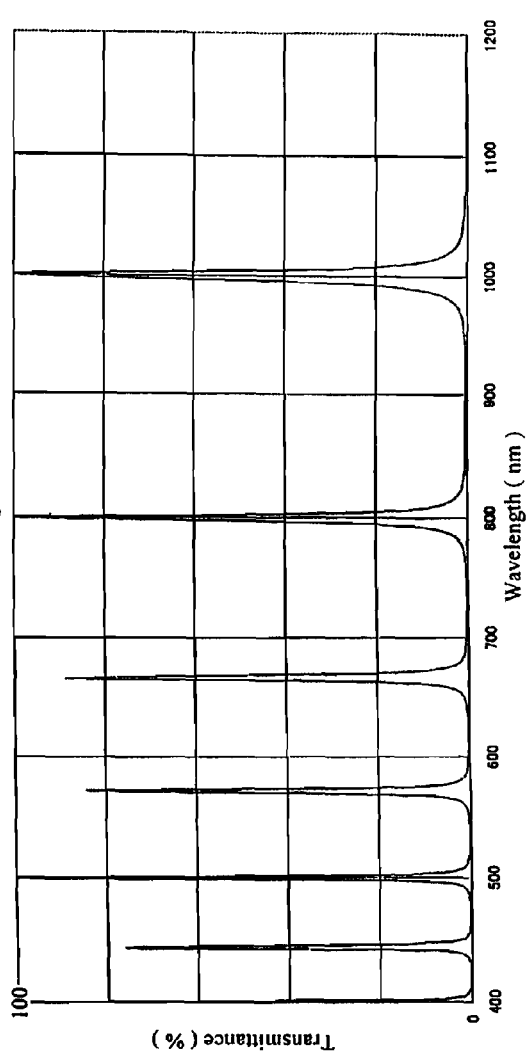
Figure 31C:
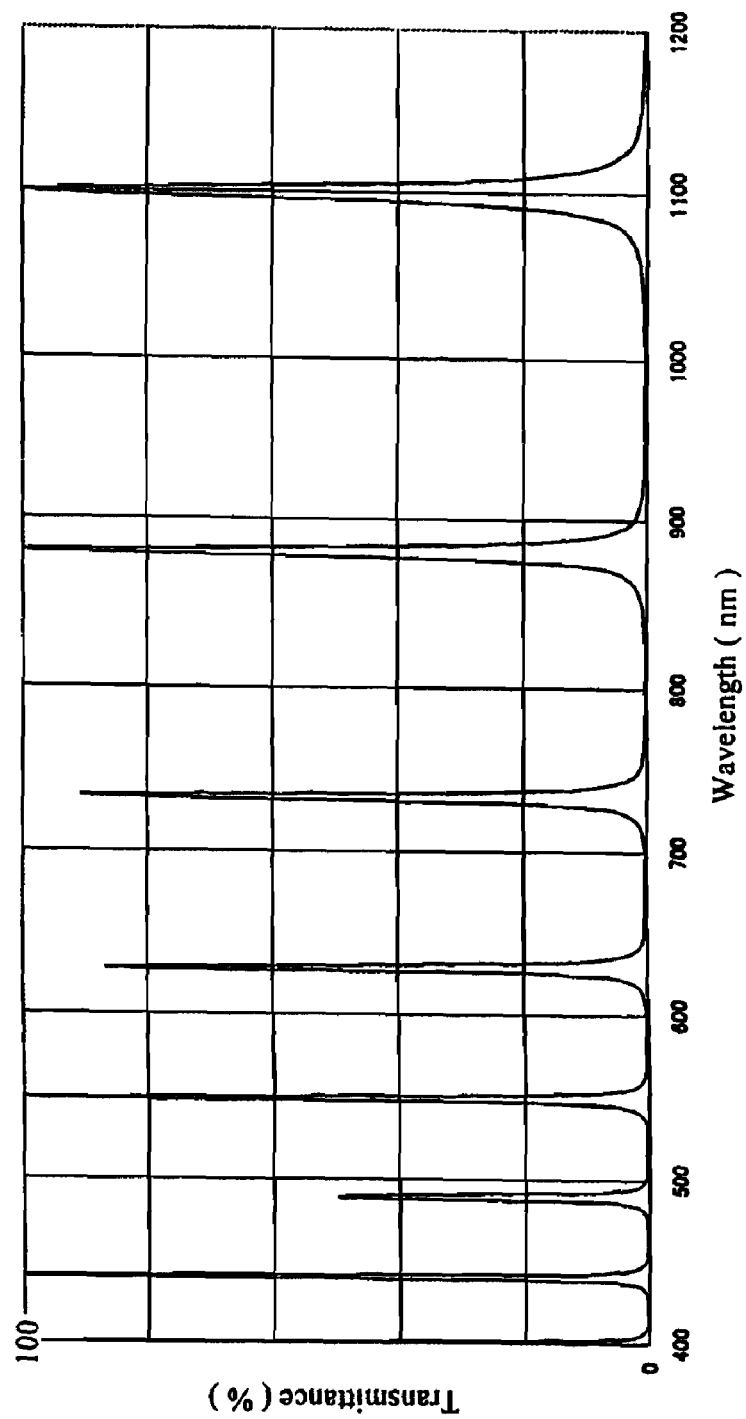

FIGS. 31(a)-31(c) show the spectral transmittance for an exemplary design of a two-layer, tunable Fabry-Perot etalon filter. In this exemplary design, it is assumed that the fluorescence emitted by the fluorescent labels is in the range 950-1050 nm. FIGS. 31(a), 31(b) and 31(c) show the spectral transmittance of the tunable filter when the air gap distance d is 1800, 2000, and 2200 nm, respectively.

The reflectance of the reflective coating deposited on the substrates forming the air gap is 90% or more for the light entering the tunable filter at an incident angle of 0° (as measured from the surface normal). As can be seen in FIGS. 31(a)-31(c), the air gap distance d can be changed so as to scan the narrow band width passband of the tunable filter at least in the wavelength range 900-1100 nm.

Figure 32A:
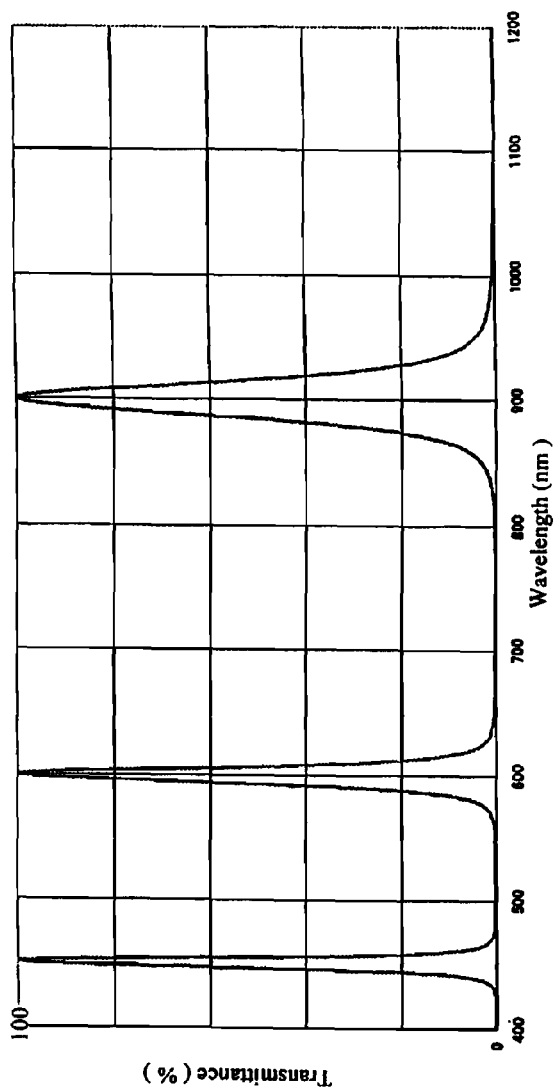
FIGS. 32(a)-32(c) show the spectral transmittances of an exemplary three-layer, tunable filter, with FIG. 32(a) showing the spectral transmittance when $d_1=d_2=900$ nm, with FIG. 32(b) showing the spectral transmittance when $d_1=d_2=1000$ nm, and with FIG. 32(c) showing the spectral transmittance when $d_1=d_2=1100$ nm.
Figure 32B:
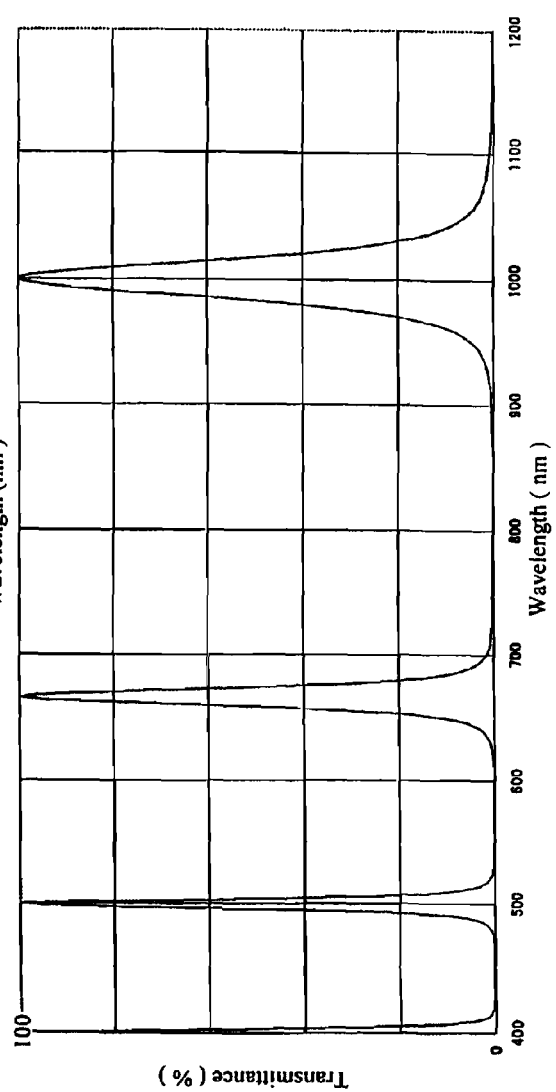
Figure 32C:
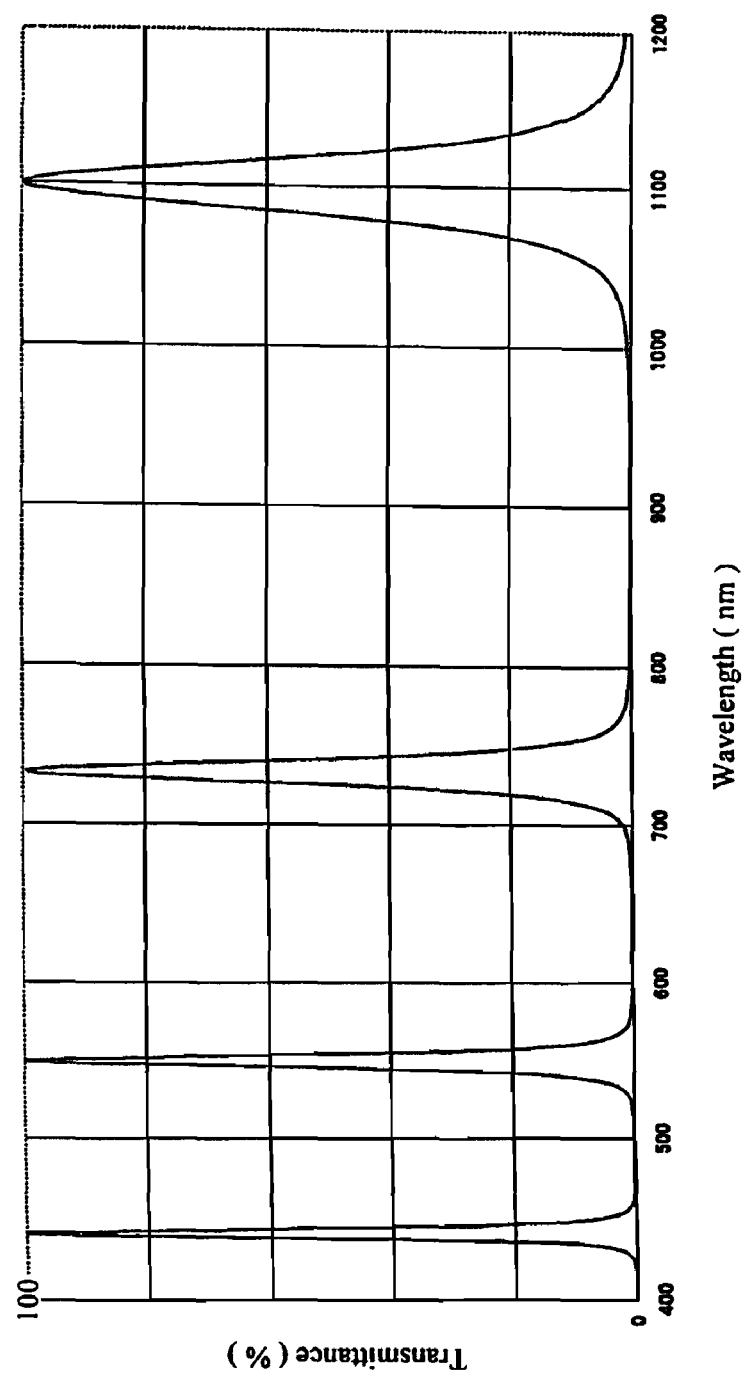

FIGS. 32(a)-32(c) show the spectral transmittance of an exemplary design of a three-layer, tunable Fabry-Perot etalon filter. In this exemplary design, it is assumed that the fluorescence emitted by the fluorescent labels is in the range 950-1050 nm. This exemplary design is intended to increase the bandwidth of the passbands within the infrared range so as to improve the S/N ratio of the fluorescent detection.

Furthermore, the reflective coating can have a lower reflectance so as to facilitate manufacture of the coating, thus improving the production yield in manufacturing the tunable filter. With a three-layer design of the tunable filter, the reflective coating needs to have a reflectance of only 80% or more. The air gap distances $d_1$ and $d_2$ can be maintained identical while being increased or decreased so that the maximum transmissions of the passbands in the wavelength range 900-1100 nm are maintained high and the transmissions in the non-transmission range are lowered.

FIG. 32(a) shows the spectral transmission when $d_1=d_2=900$ nm. Likewise, FIG. 32(b) shows the spectral transmission when both $d_1$ and $d_2$ equal 1000 nm, and FIG. 32(c) shows the spectral transmission when both $d_1$ and $d_2$ equal 1100 nm. Compared with FIGS. 31(a)-31(c), it can be seen that the width of the passbands in the transmission wavelength range 900-1100 nm are increased.

The detector (light receiving part) 36 will now be described. The detector 36 generally consists of a CCD, CMOS, or highly sensitive image pickup element. Highly sensitive image pickup elements can be preferably used in the present invention particularly because very weak light, such as fluorescence, is detected. FIGS. 33-36 show an embodiment in which a charge multiplying solid-state image pickup element is used as a highly sensitive image pickup element.

Figure 33:
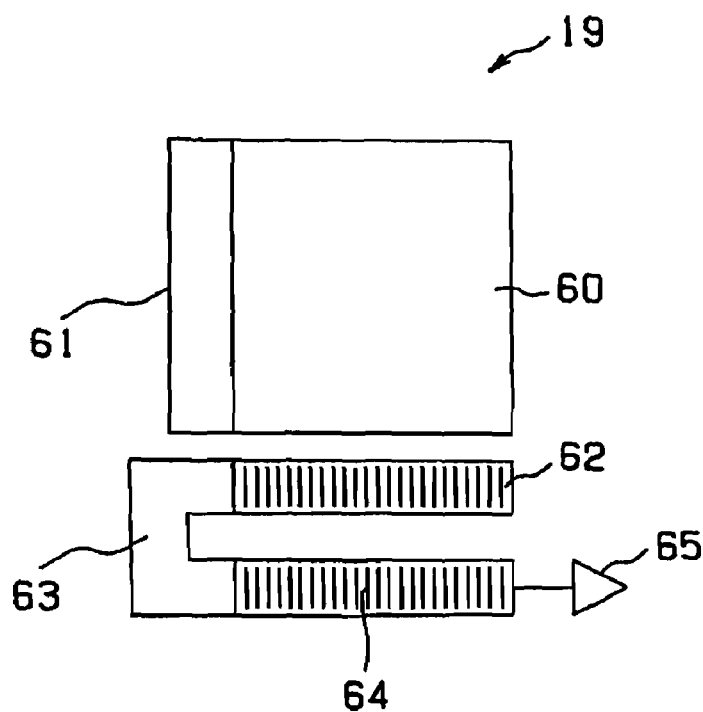
FIG. 33 shows the structure of a charge multiplying, solid-state image pickup element.

FIG. 33 is an illustration of the structure of a charge multiplying solid-state image pickup element.

Figure 34:
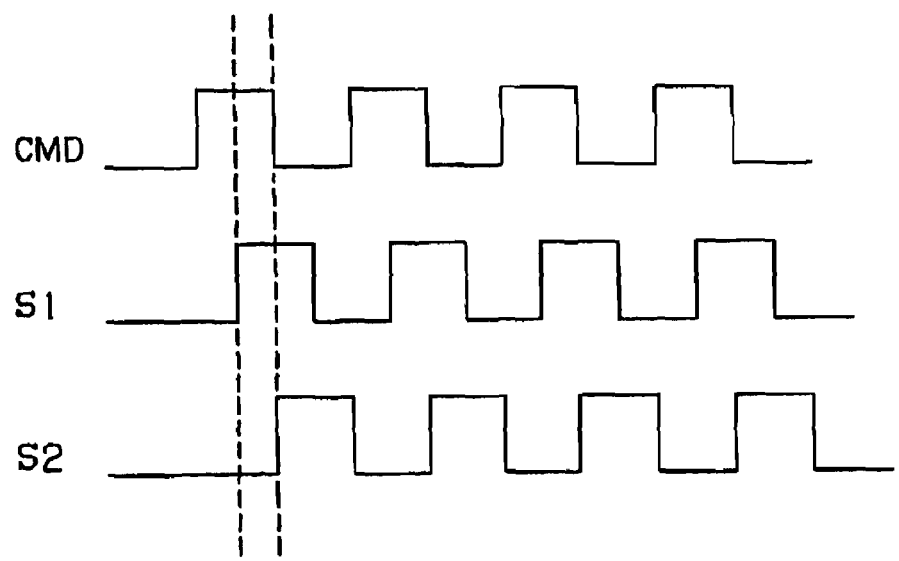
FIG. 34 is a timing chart that illustrates the relative timing of a sensitivity control pulse CMD (Charge Multiplying Detector) and of horizontal transfer pulses S1 and S2 used with the solid-state image pickup element shown in FIG. 33.

FIG. 34 is a timing chart of a sensitivity control pulse CMD (Charge Multiplying Detector) and of the horizontal transfer pulses S1 and S2.

Figure 35:
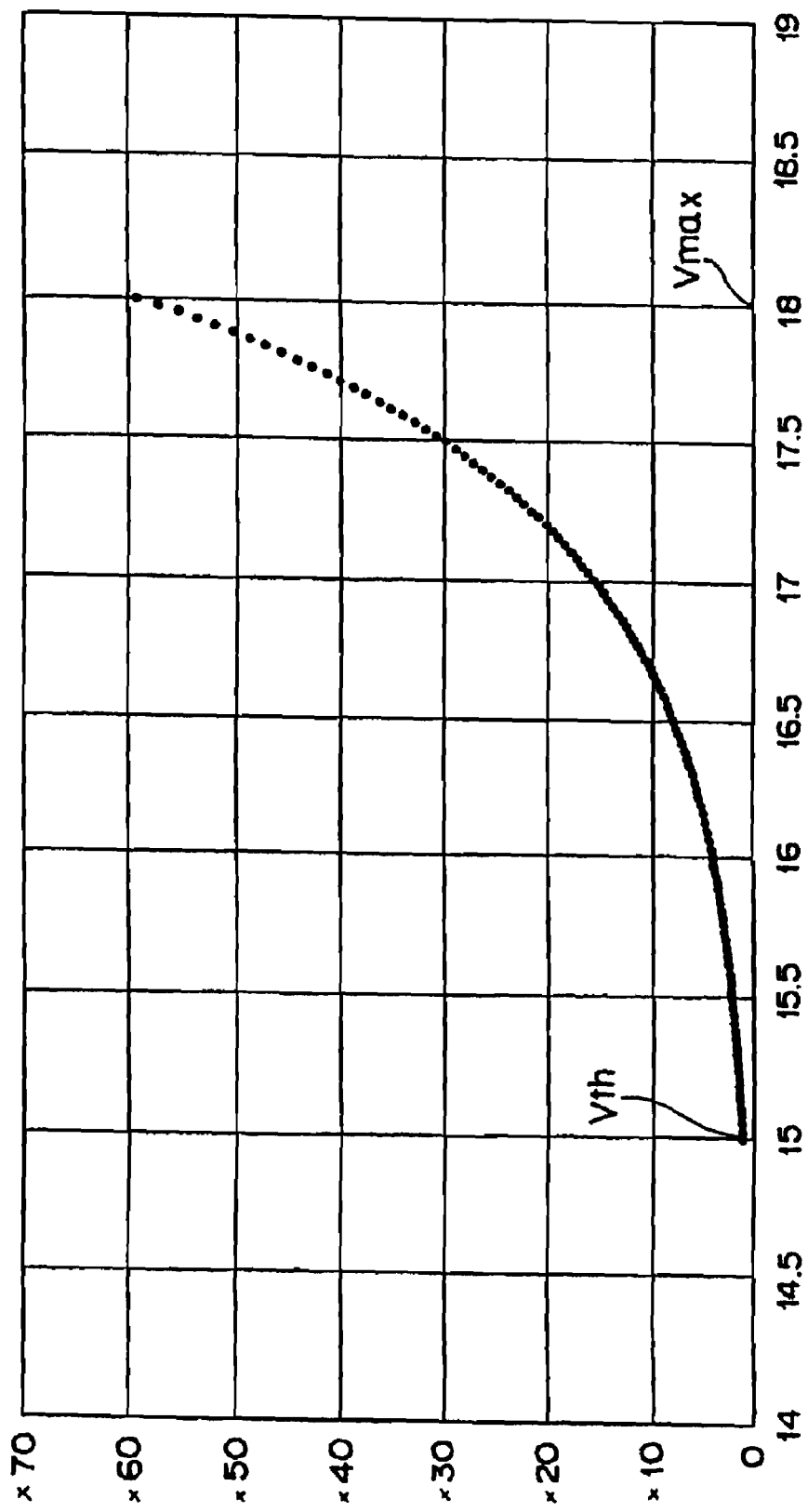
FIG. 35 shows the sensitivity (i.e., the multiplication factor) of the charge multiplying solid-state image pickup element versus the applied voltage to the solid-state image pickup element shown in FIG. 33.

FIG. 35 shows the sensitivity (i.e., the multiplication factor) of the charge multiplying solid-state image pickup element of the CMD versus the applied voltage.

Figure 36:
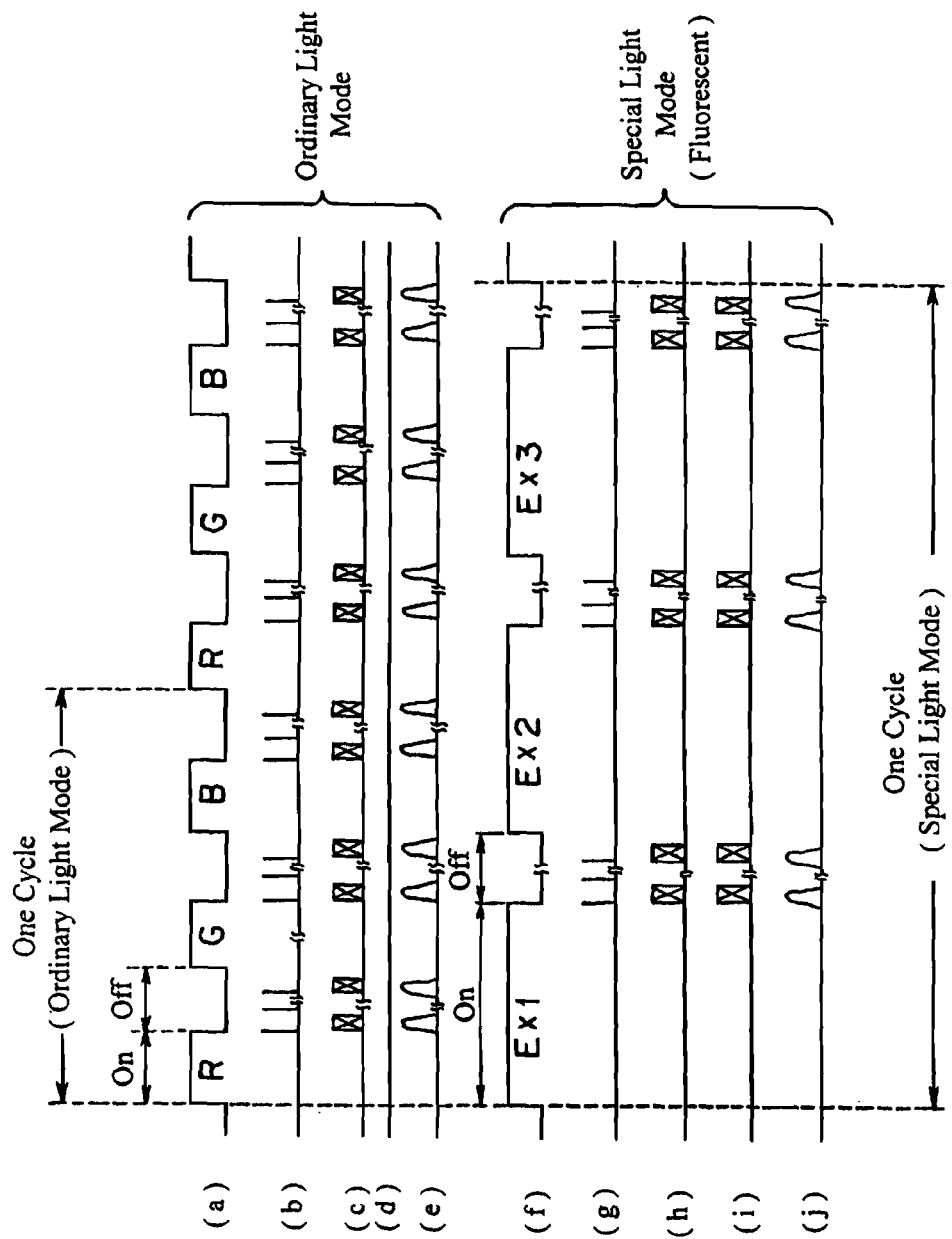
FIG. 36 is a timing chart for driving the charge multiplying, solid-state image pickup element shown in FIG. 33.

FIG. 36 is a timing chart for driving the charge multiplying solid-state image pickup element. The various signals (a)-(j) can be decoded using Table 5 below.

TABLE 5

| Signal | Meaning or Operation |
| --- | --- |
| (a) | action of the rotational filter during the ordinary light observation mode |
| (b) | vertical transfer pulses P1, P2 during the ordinary light observation mode |
| (c) | horizontal transfer pulses S1, S2 during the ordinary light observation mode |
| (d) | sensitivity control signal for the CMD during the ordinary light observation mode |
| (e) | CCD output signal (exposure/cut-off) during the ordinary light observation mode |
| (f) | action of the rotational filter during the special light observation mode |
| (g) | vertical transfer pulses P1, P2 during the special light observation mode |
| (h) | sensitivity control pulses for the CMD during the fluorescent light observation mode |
| (i) | sensitivity control pulses for the CMD during the fluorescent light observation mode |
| (j) | CCD output signal during one cycle of the fluorescent light observation mode |

The solid-state image pickup element (hereinafter referred to as a CCD) is provided with a charge multiplying part between the horizontal transfer path and an output amplifier or at individual pixels in the element. An intensive pulse electric field is applied to the charge multiplying part from the processor so that signal charges acquire energy from the electric field and collide with electrons in the valence band. This causes impact ionization at first and then produces new signal charges (secondary electrons). The charge multiplying part may be implemented using, for example, a charge multiplying solid-state image pickup element as described in U.S. Pat. No. 5,337,340, entitled "Charge Multiplying Detector (CMD) Suitable for Small Pixel CCD Image Sensors", the disclosure of which is hereby incorporated by reference.

For example, the pulses may be applied to produce secondary electrons in a chain reaction avalanche effect. Pulses with relatively low voltage compared to those for an avalanche effect are applied to produce a pair of electron-positive holes in the impact ionization. When the charge multiplying part is provided before the output amplifier in a CCD, the pulse voltage value (amplitude) or pulse number applied can be controlled in a lump so as to multiply the number of signal charges in an arbitrary manner.

On the other hand, when the charge multiplying parts are provided to individual pixels, the pulse voltage value (amplitude) or pulse number applied can be controlled pixel-by-pixel so as to multiply the number of signal charges in an arbitrary manner. The CCD in this embodiment is an FFT (Full Frame Transfer) type monochrome CCD in which the charge multiplying part is mounted between the horizontal transfer path and the output amplifier.

Referring to FIG. 33, the CCD includes an image area 60 of the light receiving part, an OB (Optical Black) part 61, a horizontal transfer path 62, a dummy 63, a charge multiplying part 64, and an output amplifying part 65. The charge multiplying part 64 includes a number of cells, with the number of cells being in the range from approximately equal to the number of horizontal transfer paths 62 to twice the number of horizontal transfer paths 62. The CCD may be an FT (Frame Transfer) type having a charge storage part.

The signal charges produced at individual pixels of the image area 60 are transferred to the horizontal transfer path 62 one horizontal line at a time according to vertical transfer pulses P1 and P2 and are then transferred from the horizontal transfer path 62 to the dummy 63 and to the charge multiplying part 64 according to horizontal transfer pulses S1 and S2. When a sensitivity control pulse CMD is applied to individual cells forming the charge multiplying part 64, the charge is sequentially multiplied in being transferred from one cell to another as far as to the output amplifying part 65. The output amplifying part 65 converts the charge from the charge multiplying part 64 to a voltage so as to produce an output signal.

The sensitivity multiplication rate obtained by the charge multiplying part 64 is modified by changing the voltage value (amplitude) of the sensitivity control pulse CMD to the charge multiplying part 64 from the CCD driving circuit. The charge multiplying part 64 executes charge multiplication at every cell. The sensitivity multiplication rate obtained by the charge multiplying part 64 is characterized in that the charge multiplication starts when the applied voltage exceeds a certain threshold Vth and the sensitivity is exponentially multiplied thereafter, as shown in FIG. 35.

The CCD driving circuit varies the voltage value (amplitude) of the sensitivity control pulse CMD shown in FIG. 36(i) based on the data supplied by the sensitivity control circuit, and outputs the sensitivity control pulse CMD that is synchronized with the horizontal transfer pulses S1 and S2, shown in FIG. 36(h), in phase to the CCD. In this manner the CCD driving circuit changes the voltage value (amplitude) of the sensitivity control pulse CMD signal that is applied to the charge multiplying part 64 so as to achieve a desired sensitivity multiplication rate. Using an image pickup element as described above as the detector 36 enables the detection of the fluorescence, which is significantly weaker than the reflected light, with a high S/N ratio.

Figure 39:
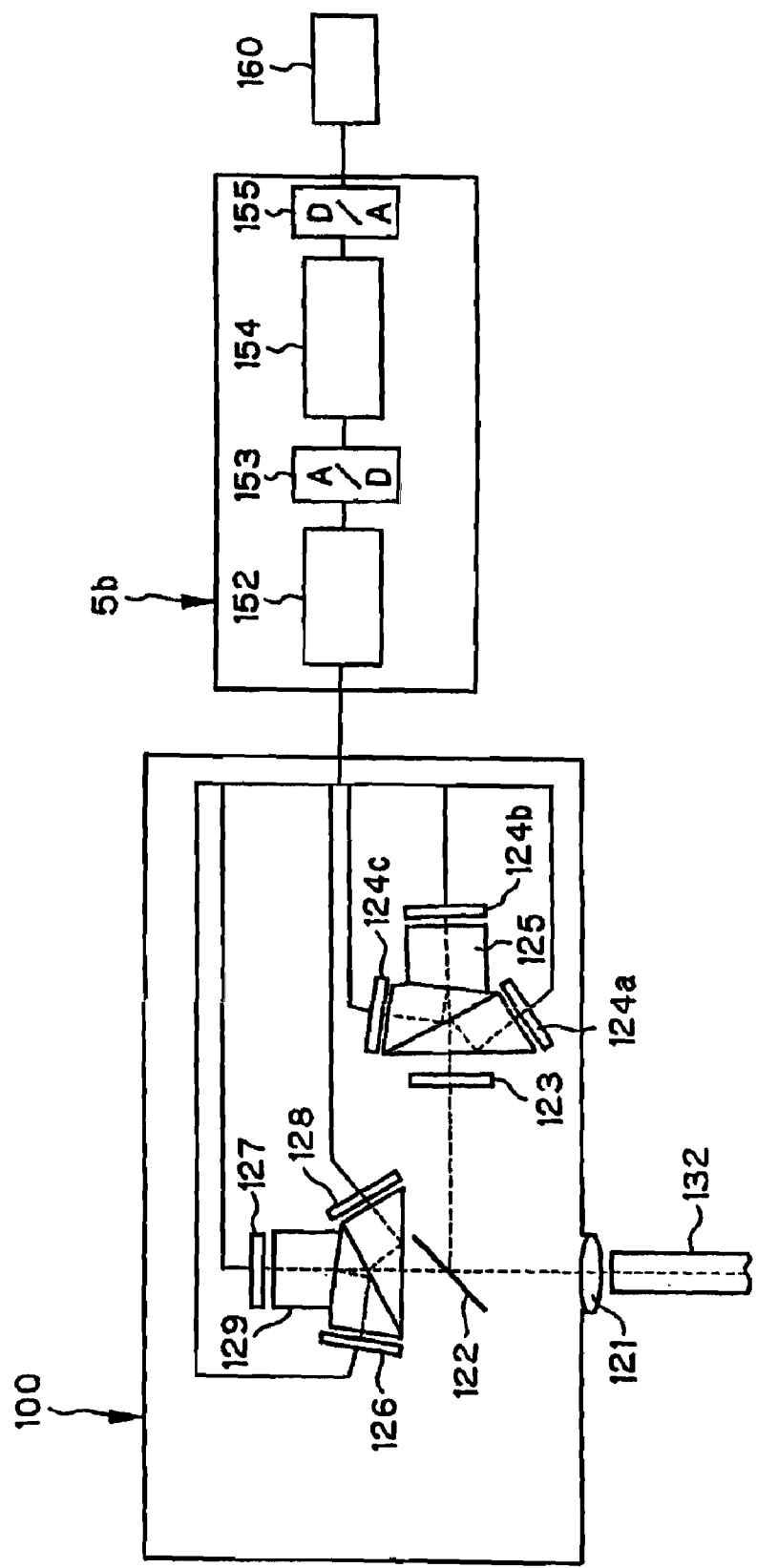
FIG. 39 is a block diagram to show an alternative configuration in part of another embodiment of the present invention.

FIG. 39 is a block diagram to show the configuration of another embodiment of the present invention. In this embodiment, a dichroic prism is used in place of the tunable filter described with reference to FIG. 12 as the wavelength separation element for separating the fluorescent wavelengths produced by the fluorescent labels. In FIG. 39, the near-infrared wavelengths transmitted through the excitation light cut-off filter are separated by the dichroic prism into individual wavelengths, which are individually detected by a CCD. In the embodiment shown in FIG. 39, the reflected light from a subject and the fluorescence are imaged by an eyepiece lens provided at the tip of a light guide fiber 132. The images are transferred to the rear end surface via the light guide fiber 132 and supplied to a camera head 100 attached to the endoscope by an imaging lens 121. Light entering the camera head 100 is separated into infrared and visible light components by a dichroic mirror 122. The infrared component reflected by the dichroic mirror 122 enters a first dichroic prism 125 via an excitation light cut-off filter 123.

The excitation light cut-off filter 123 eliminates the excitation light component and transmits the fluorescent component in the infrared range. The first dichroic prism 125 separates the incident light into three specific fluorescent wavelengths and leads them to CCDs 124a, 124b, and 124c, respectively. The CCDs 124a, 124b, and 124c detect different fluorescent wavelengths. In this way, the image of the fluorescent components produced by the fluorescent labels can be detected by the CCDs 124a, 124b, and 124c.

The lengths and number of components of wavelengths separated by the first dichroic prism 125 can be determined by the optical property of the prism in an arbitrary manner. In FIG. 39, as described above, the excitation light cut-off filter 123 blocks the excitation light wavelengths and transmits the fluorescent wavelengths. The first dichroic prism 125 and CCDs 124a-124c correspond to a detection means including the wavelength separation element for separating fluorescent wavelengths produced by plural fluorescent labels and plural detection elements for detecting individual fluorescent wavelengths separated by the wavelength separation element.

The visible light component transmitted through the dichroic mirror 122 is supplied to a second dichroic prism 129 and a camera that includes three CCDs 126, 127 and 128. The second dichroic prism 129 separates the incident light into red (R), green (G), and blue (B) components and leads them to CCDs 126, 127, and 128, respectively. In this way, ordinary visible image (ordinary optical image) components can be obtained by the CCDs 126, 127, and 128. CCDs 124a-124c and CCDs 126-128 are synchronously driven by a CCD driving circuit (not shown).

Electric signals from the CCDs 124a-124c and CCDs 126-128 are supplied to a pre-process circuit 152 of the processor 5b where adjustments are made for gain by an amplifier and for white balance of visible light images by a white-balance correction circuit, which are not shown. Then, the signals are supplied to an A/D converter 153 where analog signals are converted to digital signals. The digital signals from the A/D converter 153 are supplied to an image signal processing circuit 154 and temporarily stored in an image memory. Subsequently, they are subject to image processing, such as image enhancing and noise elimination, and display controls for concurrent display of a fluorescent image, a color image, and character information.

The image signal processing circuit 154 further executes a process for displaying a fluorescent image overlapped with an ordinary optical image or a process that normalizes the fluorescent image using data of the color and fluorescent images. This provides a fluorescent image that is easy to identify when presented with an ordinary image. The digital signals from the image signal processing circuit 154 are supplied to a D/A converter 155 where they are converted to analog signals. The analog signals are supplied to the monitor 160 for display.

On the monitor, several choices are available: two images, ordinary light and fluorescent, may be displayed concurrently side-by-side in the same size or in different sizes; two images may be overlapped; or processed images of fluorescent and ordinary light images may be displayed. Thus, a fluorescent image and an ordinary observation image can be viewed simultaneously. Therefore, the fluorescent image and ordinary observation image may be obtained with no time lag, enabling the locating of a lesion in a simple and highly accurate manner, which is a significant advantage in facilitating a proper diagnosis.

The excitation light cut-off filter 123, a first dichroic prism 125, three CCDs 124a, 124b, and 124c, and a detection means that includes a wavelength separation element for separating fluorescent wavelengths produced by plural fluorescent labels and plural detection elements for detecting individual fluorescent wavelengths separated by the wavelength separation element are provided at the eyepiece of an endoscope. In other embodiments of the present invention, these members can be provided at the tip of an endoscope.

An excitation light cut-off filter 123 having the transmittance shown in FIG. 10 may be used as a means for eliminating the excitation light component while transmitting the fluorescent components in the infrared range. In the exemplary structure of FIG. 39, the first dichroic prism 125 serves as a wavelength separation element that automatically separates fluorescent wavelengths without any controls, which simplifies the structure of the endoscope.

With the transmittance being separated by wavelengths, the processor 5b calculates or counts the fluorescent peak wavelengths and displays images in pseudo-colors according to the count obtained. With the transmitted light being separated by wavelengths, the fluorescent peak wavelengths are calculated or counted and reference is made to a table of the corresponding proteins which exhibit a similar profile of fluorescent peak wavelengths in a memory (not-shown) of the processor 5b so as to identify the protein present in the living body and to store this information as data in the memory.

In this way, images may be displayed in pseudo-colors, depending on the count, and the current condition of a lesion, such as whether it is cancerous, can be reliably diagnosed. Furthermore, individual in vivo protein data can be read from memory and compared with data in a table of corresponding proteins by referencing the peak transmittance wavelengths in the fluorescence.

The fluorescent wavelengths of quantum dots used as fluorescent labels can be made to have a desired Gaussian distribution by adjusting the materials and outer diameters of the quantum dots, as shown in FIG. 38. For example, for a blue series, Cd Se nano-crystals can be used with diameters of 2.1, 2.4, 3.1, 3.6, or 4.6 nm. For a green series, InP nano-crystals can be used with diameters of 3.0, 3.5, or 4.6 nm. For a red series, InAs nano-crystals can be used having diameters of 2.8, 3.5, 4.6, or 6 nm.

As described above, the present invention allows the use of quantum dots as fluorescent labels (tags) made from CdSe, InP, or InAs and having various diameters depending on the number of living subjects (proteins) to be identified, and with diameters in the range 2.1-6.0 nm. The quantum dots having plural different diameters are synthesized so as to have hydrophilicity, antibody properties, and to be bio-compatible. In addition, the materials and the outer diameters may be selected so as to provide optimized spectral properties regarding infrared excitation light and infrared fluorescence.

The quantum dots are used as fluorescent labels in this embodiment. However, materials that are excited with red or near-infrared light which reaches the deep portion of the living tissue and materials that emit fluorescent light lying in the near-infrared region are also applicable as fluorescent label materials in the diagnostics using the endoscope system according to the present invention. The fluorescent labels (tags), such as the quantum dots, that are excited with red or near-infrared light which reaches the deep portion of the living tissue and that emit fluorescent light lying in the near-infrared region may be introduced into living tissue and then irradiated by excitation light so as to cause fluorescence in the near-infrared wavelength range. This allows the detection of cancer in the earliest stage even deep inside living tissue. In this way, the present invention enables fluorescent labels that have been introduced into living tissue to be used to diagnose cancer in its earliest stage.

Figure 40:
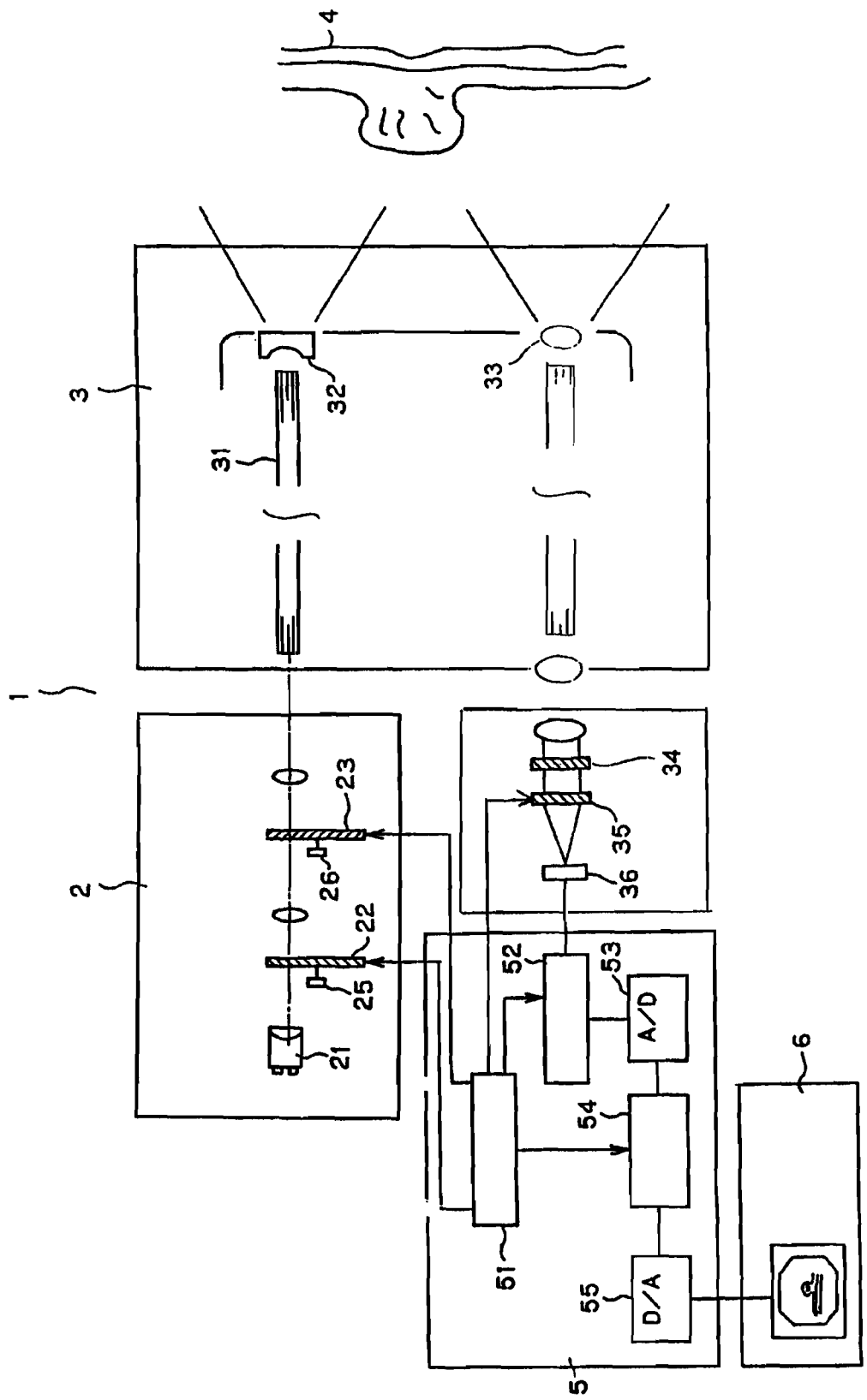
FIG. 40 shows the overall structure of another embodiment of an endoscope system according to the present invention, wherein the optical elements for separating and detecting plural fluorescent light sources are located within a separate housing that receives light from the endoscope tip of an endoscope that uses an optical fiber bundle in its observation optics (such a combination is sometimes termed a 'fiberscope')
Figure 41:
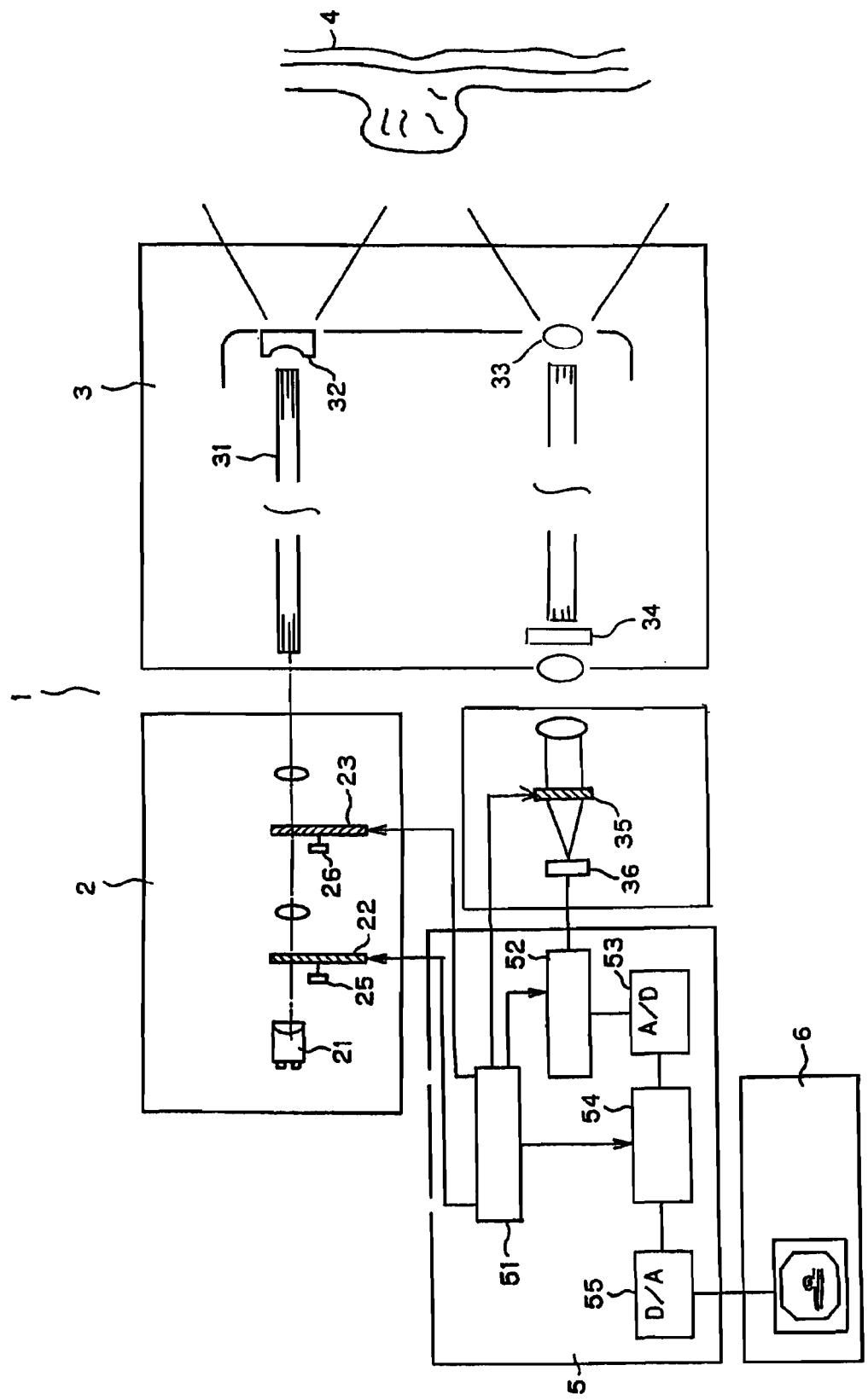
FIG. 41 illustrates a minor change from that illustrated in FIG. 40.
Figure 42:
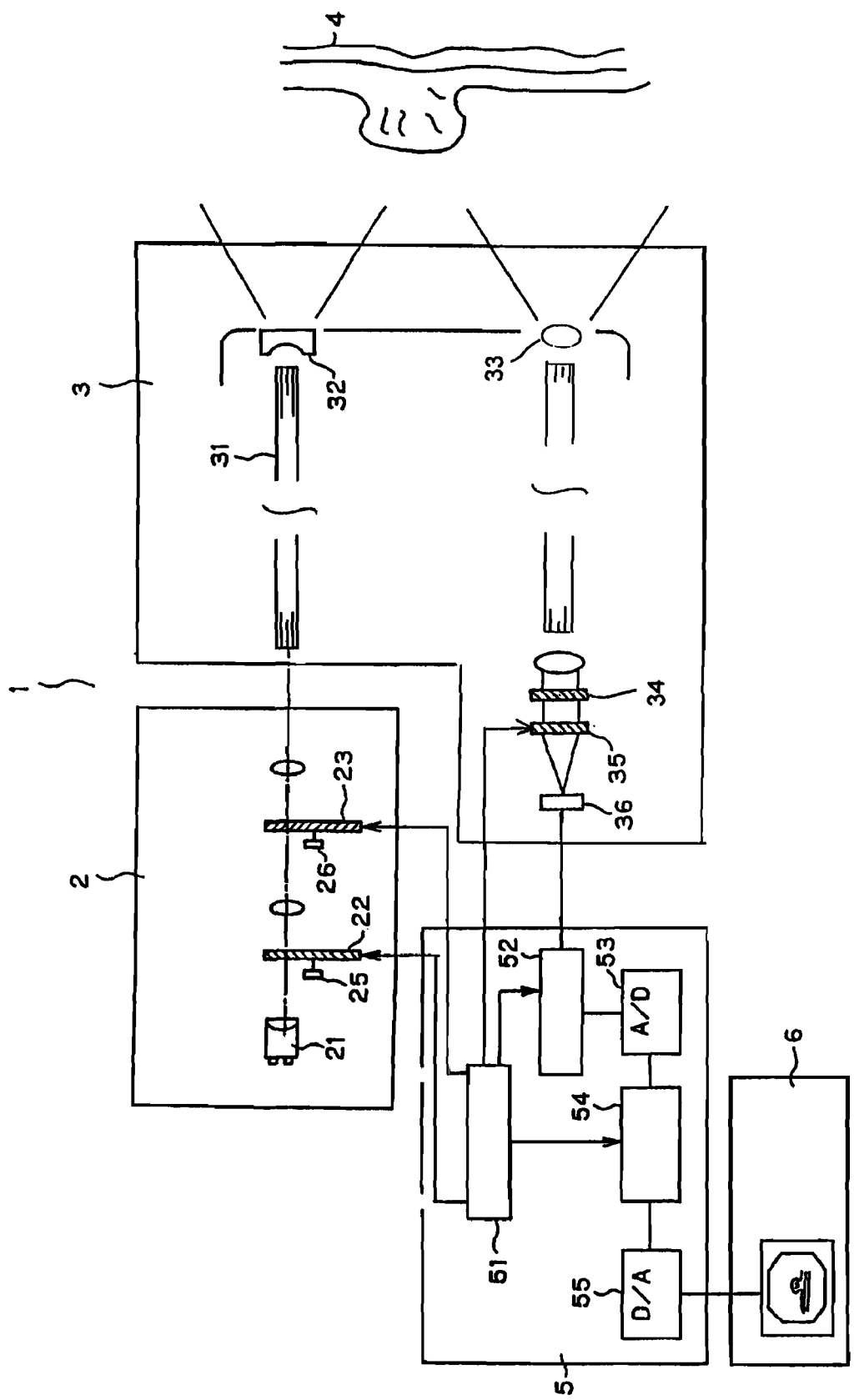
FIG. 42 also illustrates a minor modification from FIG. 40.

FIGS. 40-42 show alternative embodiments of the entire structure of the endoscope system according to the present invention wherein the structure that separates and detects plural fluorescent wavelengths is positioned other than in the endoscope tip. As the individual components are numbered identically with those of FIG. 1, only the differences will be now be described. FIG. 40 shows the overall structure of a second embodiment of an endoscope system according to the present invention, characterized by having the components that separate and detect plural fluorescent wavelengths within the endoscope tip of the type that uses an optical fiber (fiberscope). Whereas in FIG. 1 the optical elements including the excitation light cut-off filter 34 are positioned just after the objective lens 33, in FIG. 40 a fiber bundle (a so-called image guide fiber bundle) is arranged just after the objective lens, and an ocular lens is provided at the exit side of the fiber bundle. The detection optical elements, which have a similar structure to those in FIG. 1, may be arranged in a separate housing from that which houses the insertion section and ocular lens.

Figure 43:
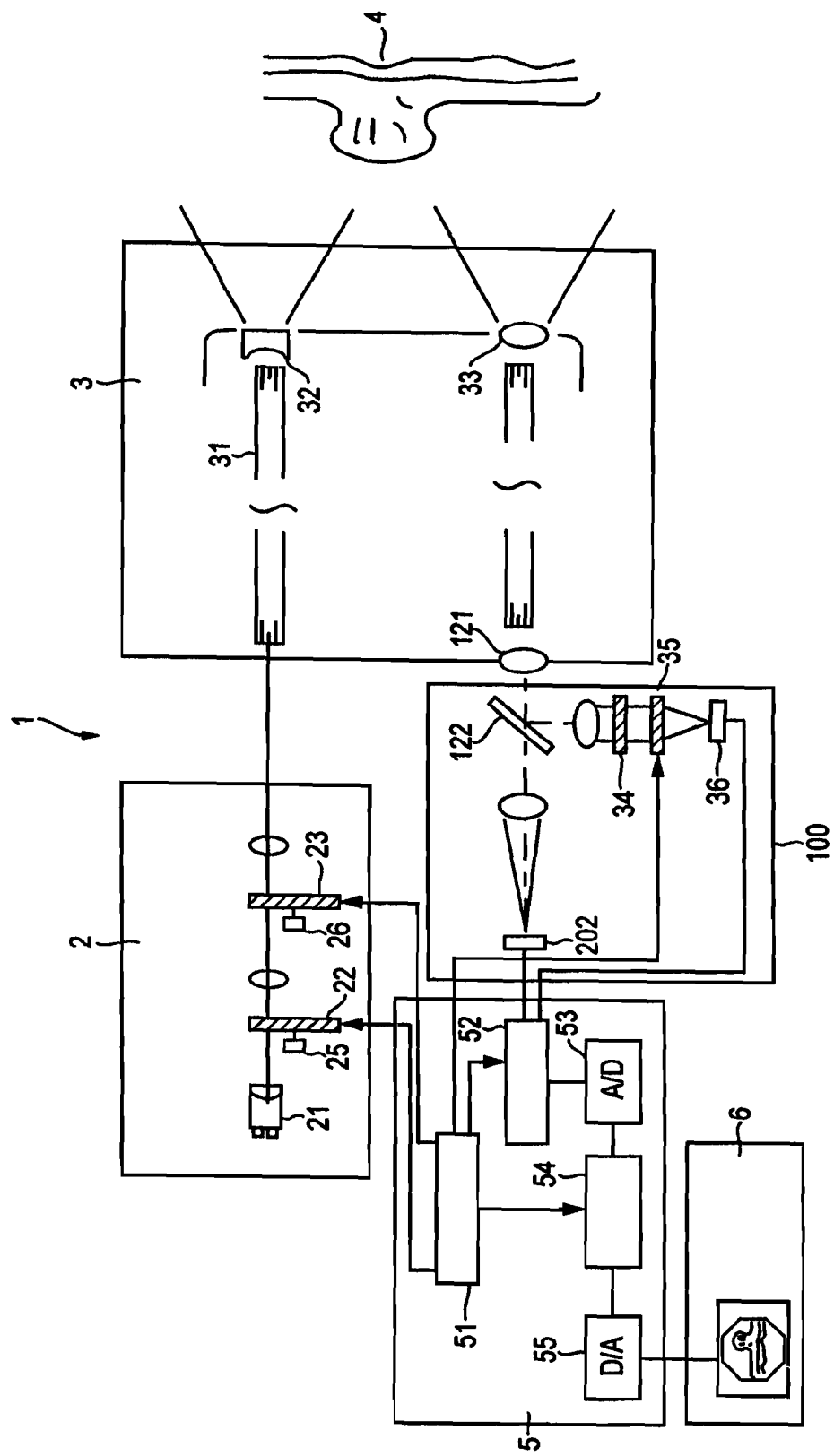
FIG. 43 illustrates another embodiment of the present invention.

FIG. 41 illustrates a minor change from that illustrated in FIG. 40. Whereas in FIG. 40 the excitation light cut-off filter 34 is arranged within the ocular lens, in FIG. 41 it is arranged outside the ocular lens by being positioned within the insertion section between the optical fiber bundle and the ocular;

FIG. 42 also illustrates a minor modification from FIG. 40. In FIG. 40 the optical elements are arranged at the exit side of an ocular lens so as to be outside the insertion section. On the other hand, in FIG. 42, the housing of the optical elements is united with the fiber scope (i.e., all optical elements are arranged within the insertion section). Whereas in FIG. 40 the optical elements for separating and detecting plural fluorescent light sources are arranged at the exit side of the ocular lens, in FIG. 42 these same optical elements are united within the housing of the fiberscope (i.e., all optical elements are arranged in the housing of the insertion portion of the endoscope);

FIG. 43 shows another embodiment of the present invention. Only the differences with regard to FIG. 43 will be described as compared to FIG. 39. In this embodiment, a tunable filter 35 and a detector 36 are used as in FIG. 1 as a wavelength separation element for separating fluorescent wavelengths emitted by the fluorescent labels in lieu of using a dichroic prism 125 and the three CCDs 124a, 124b, and 124c shown in FIG. 39. Furthermore, a color CCD 202 is used in lieu of the second dichroic prism 129 for detecting visible light components and the plural-circuit-board camera that uses the three CCDs 126, 127, and 128. Thus, the number of CCDs used at the camera head can be significantly reduced and this not only makes for a more compact design but also the endoscope has reduced cost. Also with this structure, the same detection ability of visible and fluorescent light as the endoscope system having the structure shown in FIG. 39 can be obtained. The color CCD 202 can be replaced by a monochrome CCD. In such a case, the light source unit 2 emits the light in a sequential manner as in embodiment 1.

Figure 44:
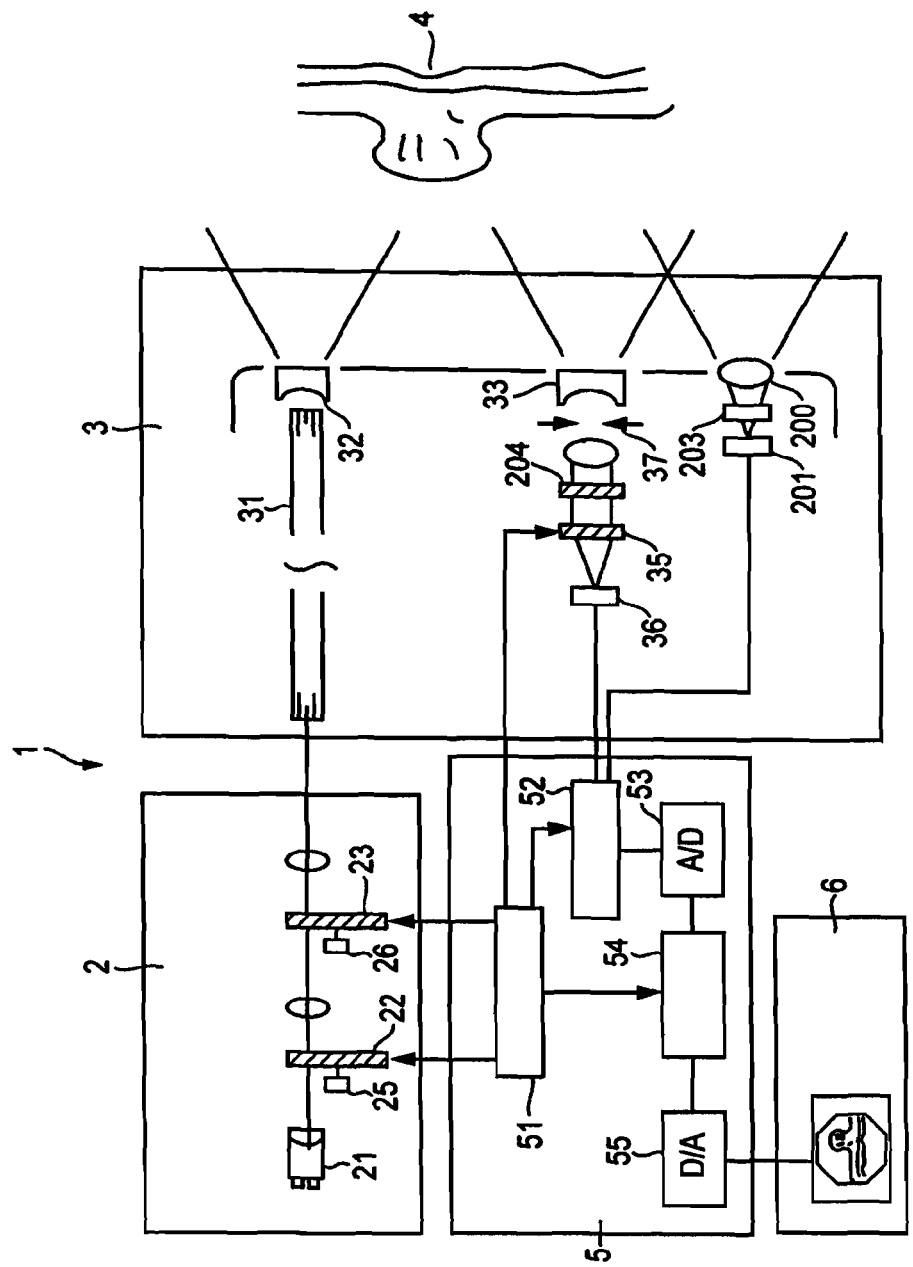
FIG. 44 illustrates an additional embodiment of the present invention.

FIG. 44 shows another embodiment of the present invention. Again, only the differences relative to the structure shown in FIG. 1 will be described. In this embodiment, an endoscope optical system 3 that utilizes two observation optical systems, one observation optical system for detecting only wavelengths of light in a band that corresponds to an emitted fluorescence, and a second observation optical system for detecting only visible light.

The observation optical system for detecting only visible light is formed of an objective lens 200, a visible light transmitting filter 203, and a CCD 201. The visible light transmitting filter 203 is different from the visible light transmitting filter 27a only in terms of its outer diameter.

Figure 45:
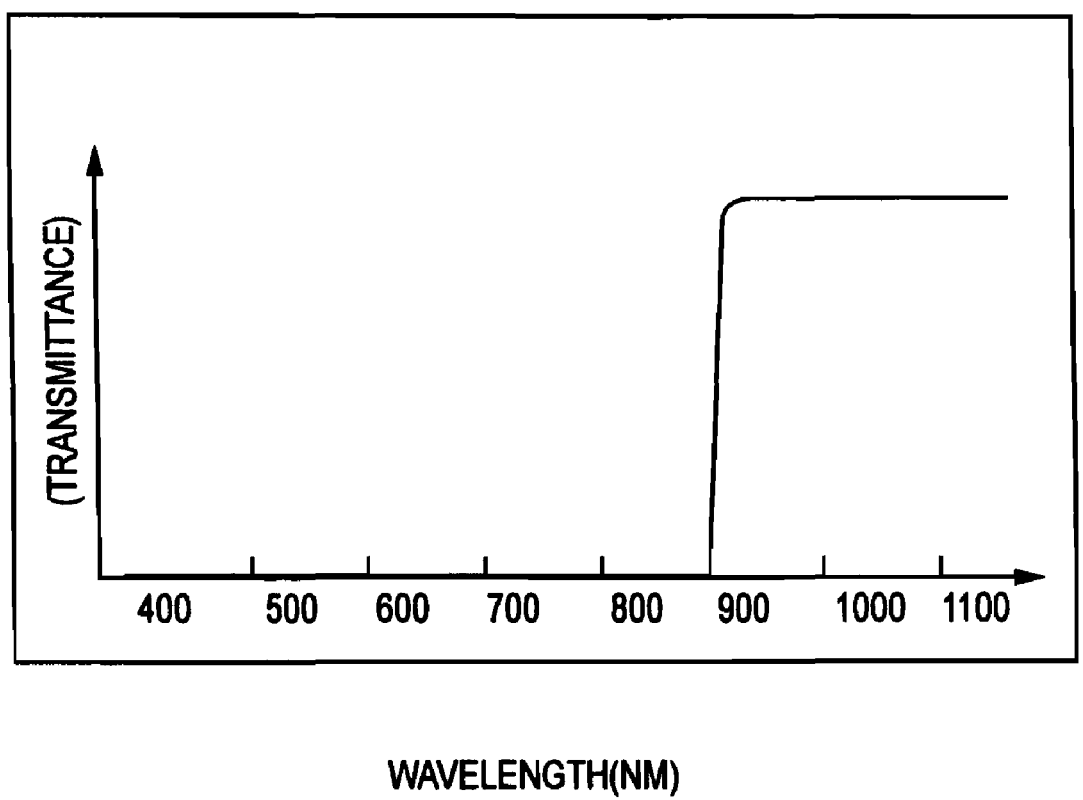
FIG. 45 illustrates the spectral transmittance of an infrared transmitting filter that is used for detecting only fluorescent wavelengths.

The observation optical system for detecting only wavelengths corresponding to those of an emitted fluorescence is different from that of FIG. 1 in that it uses an infrared transmitting filter 204 having a spectral transmittance as shown in FIG. 45 in lieu of using the excitation light cut-off filter 34 shown in FIG. 1. The detector 36 detects only wavelengths corresponding to an emitted fluorescence. Thus, the detector 36 can be a highly sensitive detector that detects only infrared light. The morphology (i.e., structure) of an observation site is obtained by using a CCD 201 that detects visible light components. The detector 36 can be a photo-electric sensor made, for example, of PbS that is highly sensitive to infrared wavelengths instead of visible wavelengths (the latter are normally detected with an image pickup element that uses, for example, a CCD). This allows for improved S/N in the detection of fluorescent components, which are significantly weaker than the light emitted in the visible region. The endoscope system of this embodiment enables one to observe a visible image and a fluorescent image simultaneously by irradiating illumination lights for visible observation and for fluorescent observation at the same time. In this case, the structure of the illumination optical system 2 is simplified.

Figure 46:
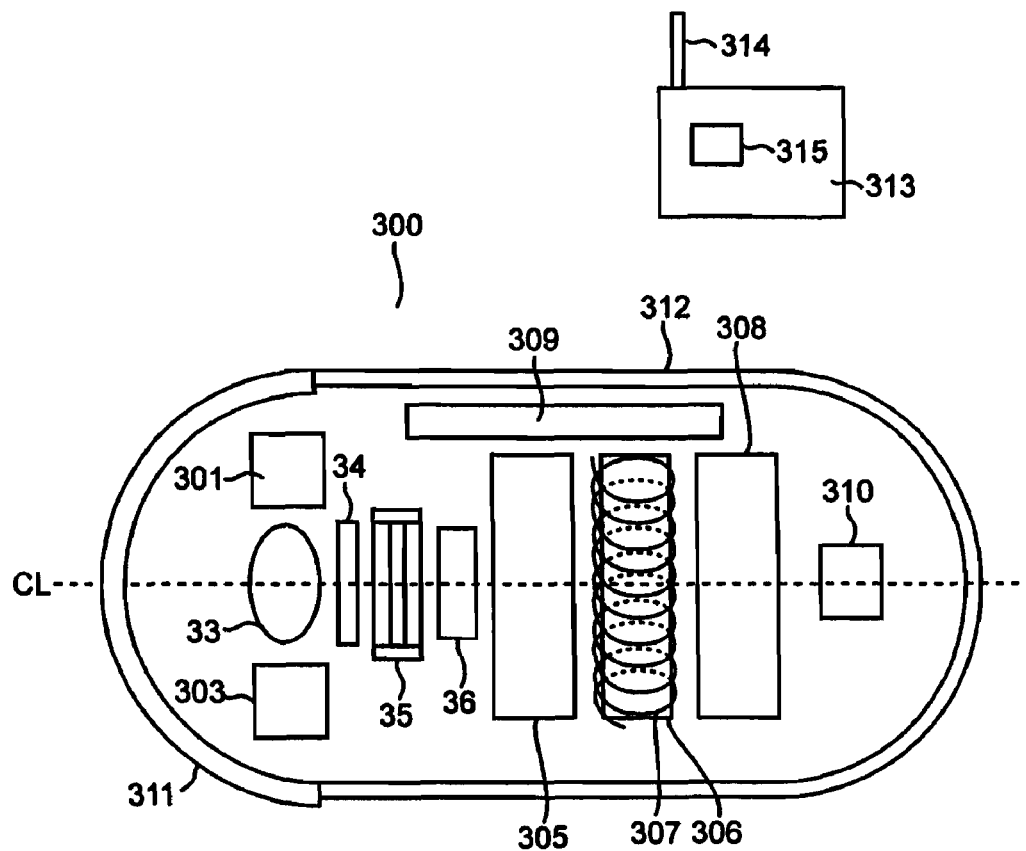
FIGS. 46 and 47 show another embodiment of the present invention that uses a capsule endoscope that functions similarly to the endoscope shown in FIG. 1, but outputs its data wirelessly, with FIG. 46 being a side sectional view and FIG. 47 being a front view.
Figure 47:
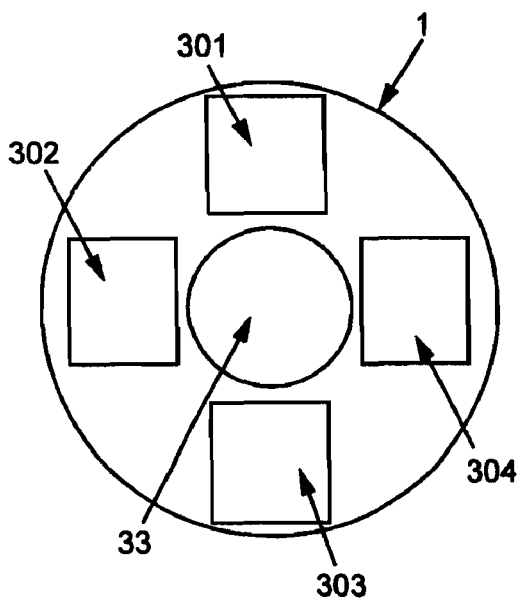

FIGS. 46 and 47 show another embodiment of the present invention. In this embodiment, the function of the endoscope system described with regard to FIG. 1 is realized in a capsule endoscope. In FIG. 46, the same items have been labeled with the same reference numbers and thus only the differences will be discussed.

In FIG. 46, a capsule endoscope apparatus 300 includes light emitting elements 301-304 (such as LED's), a lens 33 for collecting light that has been reflected from a living body (e.g. an examination subject) or fluorescence, an excitation light cut-off filter 34, a tunable filter 35 and a detector 36. The lens 33 has an optical axis CL. The light emitting elements 301 to 304 are asymmetrically provided in relation to the optical axis CL.

The capsule endoscope apparatus 300 also comprises a control circuit 305, a power source 306 such as a capacitor and a battery, a coil 307 that is electrically connected to the power source 306, a magnet 308, and antenna 309, and a transmitter 310. A transparent cover 311 transmits the emitted light from the light emitting elements 301-304 so as to illuminate the living body and introduces the reflected light or fluorescence into the lens 33. A case 312 is also shown. When the magnet 308 is magnetized by externally provided magnetic field lines, the coil 307 generates electric current due to magnetic induction so as to charge the capacitor or battery of the power source 306. The magnet 308 serves as an energy source to move the capsule endoscope apparatus 300 using externally provided electromagnetic waves. The antenna 309 transmits detection signals of the detector 36 to an external unit. The transmitter 310 transmits information on the current position of the capsule endoscope apparatus 300 to an external unit that, together with the endoscope apparatus 300, forms a capsule endoscope system.

The external unit 313 has a transmission/reception antenna 314 and a monitor 315. It also has a control circuit, not shown. The transmission/reception antenna 314 receives signals transmitted from the antenna 309 and transmitter 310 of the capsule endoscope apparatus 300. It also transmits electromagnetic waves or magnetic energy to the magnet 308. The monitor 315 displays images that are formed based on the detection signals of the detector 36 transmitted from the antenna 309.

FIG. 47 is an end view of the front end of the capsule endoscope apparatus as viewed from a position on the optical axis. The light emitting elements 301, 302, and 303 emit blue, green, and red light, respectively. The light emitting element 304 emits infrared light having wavelengths including part of the wavelength range from 600 to 2000 nm that comprises the excitation light wavelength of the fluorescent labels. A different detection system from that used in the endoscope system shown in FIG. 1 is used for detecting the wavelengths of reflected visible light versus fluorescence from a living body.

The endoscope apparatus shown in FIG. 1 uses band pass filters having different properties and that are provided in the light source optical system 2 for selecting the wavelengths of the illumination light that illuminates the living body tissue. In this embodiment, as shown in FIG. 47, multiple light emitting elements having different wavelengths, such as LED's, are used in lieu of using the light source optical system 2. The control circuit 305 is used to intermittently energize multiple LEDs 301 to 304 that emit different wavelengths sequentially so as to utilize the same illumination system as the light source optical system 2. In this manner, the capsule endoscope system of the present invention can separately detect visible light that is reflected by the living tissue versus fluorescence that is emitted by the fluorescent labels. In addition, by using a capsule endoscope that employs wireless technology in lieu of, for example, using an insertion-type endoscope as shown in FIG. 1 (i.e., one that is hardwired) the pain experienced by a patient during an endoscopic examination can be reduced.

The present invention enables the user to provide advanced (i.e., early) diagnosis including diagnosis of the malignancy of lesions using an endoscope system than previously available in prior art endoscope systems. Using quantum dots for fluorescent markers in conjunction with the endoscope system of the present invention allows for more than one hour of endoscopic observation, as the fluorescence from quantum dots has a prolonged emission time period and is bright. Moreover, the fluorescence emitted by quantum dots has a narrow wavelength range, Gaussian distribution, and thus is suitable for detection by an tunable filter, such as a Fabry-Perot etalon type, band pass filter.

The invention being thus described, it will be obvious that the same may be varied in many ways. For example, the combinations of the excitation light cut-off filters and tunable filter(s) are not restricted those described above. And, as is apparent from the various embodiments discussed above, many modifications are allowed in the endoscopic system used while practicing the basic concept of the invention. Thus, variations from the specific embodiments discussed above are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:
1. An endoscope for detecting fluorescence emitted by a plurality of fluorescent labeling materials introduced into living tissue, comprising:
   an illumination unit; and
   an observation unit;
   wherein
   the illumination unit generates near-infrared illumination light that includes a wavelength band for excitation of the fluorescent labeling materials;

the observation unit includes an objective optical system, an excitation light blocking filter, a wavelength tunable filter, and a detector;

the combination of the excitation light blocking filter and the wavelength tunable filter passes light in the visible region, and has a passband in the infrared region which allows the fluorescence emitted from the fluorescent labeling material that is under observation to pass through, wherein a peak transmittance wavelength for the passband varies in accordance with the tuning of the wavelength tunable filter; and the spectral transmittance of said combination satisfies the following conditions:

$T3 \geq 60\%$ $T4 \leq 0.01\%$ $T5 \geq 65\%$ $5 \text{ nm} \leq d5 \leq 35 \text{ nm}$ where T3 is the average transmittance within the visible wavelength range of $400 \text{ nm} \leq \lambda \leq 650 \text{ nm}$, T4 is the transmittance for the wavelengths within a range 20 nm above and 20 nm below the wavelength range of the excitation light generated by the illumination unit, T5 is the transmittance at the peak transmittance wavelength for an infrared passband, d5 is the infrared passband's full width as measured at 50% of the peak transmittance, and $\lambda$ is the wavelength of light incident onto the wavelength tunable filter.

2. The endoscope system according to claim 1, wherein the wavelength tunable filter includes at least three semi-transparent base substrates.

* * * * *